US012667497B2

(12) United States Patent
Evans et al.

(10) Patent No.: US 12,667,497 B2
(45) Date of Patent: Jun. 30, 2026

(54) COMPRESSION GARMENT APPARATUS

(71) Applicant: Koya Medical, Inc., Oakland, CA (US)

(72) Inventors: Ryan Evans, San Francisco, CA (US); Jarren Baldwin, Oakland, CA (US); John C. Pamplin, Oakland, CA (US); Connor Meehan, Pleasant Hill, CA (US); Jay Zuerndorfer, Oakland, CA (US); Anand Doraiswamy, Oakland, CA (US)

(73) Assignee: Koya Medical, Inc., Dallas, TX (US)

( * ) Notice: Subject to any disclaimer, the term of this patent is extended or adjusted under 35 U.S.C. 154(b) by 737 days.

(21) Appl. No.: 18/165,527

(22) Filed: Feb. 7, 2023

(65) Prior Publication Data

US 2023/0248579 A1 Aug. 10, 2023

Related U.S. Application Data

(60) Provisional application No. 63/308,667, filed on Feb. 10, 2022.

(51) Int. Cl.
 *A61H 11/00* (2006.01)
 *A61F 13/08* (2006.01)
 (Continued)

(52) U.S. Cl.
 CPC ............ *A61F 13/085* (2013.01); *A61H 11/00* (2013.01); *F03G 7/06143* (2021.08);
 (Continued)

(58) Field of Classification Search
 CPC .. A61H 11/00; A61H 11/02; A61H 2011/005;
 A61H 2209/00; A61H 23/02; A61H 2201/0207; A61H 2201/1207; A61H 1/008; A61F 13/085; A41C 1/12; A41C 1/16; A43C 11/00; A61B 17/132; A61B 17/1325; F03G 7/06143
 See application file for complete search history.

(56) References Cited

U.S. PATENT DOCUMENTS 4,018,064 A 4/1977 Doslik
4,527,402 A 7/1985 Swallow et al.
(Continued)

FOREIGN PATENT DOCUMENTS

CN 101098670 B 7/2011
CN 103941909 A 7/2014
(Continued)

*Primary Examiner* — Brandy S Lee
*Assistant Examiner* — Sara K Toich
(74) *Attorney, Agent, or Firm* — Knobbe, Martens, Olson & Bear, LLP

(57) ABSTRACT

This disclosure relates to compression garments, specifically to compression garments to promote lymphatic circulation and/or circulation of other bodily fluids. The garments can include compression actuator units that can apply a pull force on a strap of the compression garment to apply compression to an anatomical feature of the user. The compression actuator units can be actuated via contraction of a wire made of shape memory material. The compression actuator units can include a plurality of levers to amplify the effect of the contraction of the wire to provide a wide range of compressive forces to the user.

20 Claims, 51 Drawing Sheets

(51) Int. Cl.
  *F03G 7/06*          (2006.01)
  *A61F 13/00*         (2024.01)

(52) U.S. Cl.
  CPC .............. *A61F 2013/00127* (2013.01); *A61H*
        *2011/005* (2013.01); *A61H 2209/00* (2013.01)

(56)                 References Cited

U.S. PATENT DOCUMENTS

| | | |
|---|---|---|
| 5,787,732 A | 8/1998 | Perron et al. |
| 5,996,205 A | 12/1999 | Mashiko et al. |
| 5,997,465 A | 12/1999 | Savage et al. |
| 6,123,681 A | 9/2000 | Brown, III |
| 6,190,344 B1 | 2/2001 | Bobroff |
| 6,509,094 B1 | 1/2003 | Shah et al. |
| 7,857,777 B2 | 12/2010 | Larson et al. |
| 7,868,221 B2 | 1/2011 | Munch-Fals et al. |
| 7,896,825 B2 | 3/2011 | Atkinson et al. |
| 8,517,963 B2 | 8/2013 | Larson et al. |
| 8,523,794 B2 | 9/2013 | Iker et al. |
| 8,764,689 B2 | 7/2014 | Toth |
| 8,801,643 B2 | 8/2014 | Deshpande et al. |
| 9,027,408 B2 | 5/2015 | Toth |
| 9,161,878 B1 | 10/2015 | Pamplin et al. |
| 9,248,074 B2 | 2/2016 | Toth |
| 9,271,676 B2 | 3/2016 | Alanen et al. |
| 9,271,890 B1 | 3/2016 | Pamplin et al. |
| 9,326,911 B2 | 5/2016 | Wyatt et al. |
| 9,421,142 B2 | 8/2016 | Malhi et al. |
| 9,463,821 B1 | 10/2016 | Critchley et al. |
| 9,516,923 B2 | 12/2016 | Capra et al. |
| 9,555,935 B2 | 1/2017 | Fiedler |
| 9,572,410 B2 | 2/2017 | Fiedler |
| 9,677,581 B2 | 6/2017 | Tucholke et al. |
| 9,700,102 B2 | 7/2017 | McCleary et al. |
| 9,907,367 B2 | 3/2018 | Paik et al. |
| 9,936,772 B2 | 4/2018 | Paik |
| 10,071,012 B2 | 9/2018 | Larson et al. |
| 10,085,521 B2 | 10/2018 | Chen et al. |
| 10,098,422 B2 | 10/2018 | Fiedler et al. |
| 10,111,500 B2 | 10/2018 | Lambert |
| 10,143,270 B2 | 12/2018 | Fiedler et al. |
| 10,188,152 B2 | 1/2019 | Stasey et al. |
| 10,206,461 B1 | 2/2019 | Swetish |
| 10,285,902 B2 | 5/2019 | Pamplin et al. |
| 10,307,074 B2 | 6/2019 | Ward |
| 10,426,202 B2 | 10/2019 | Wyatt et al. |
| 10,441,491 B2 | 10/2019 | Wyatt et al. |
| 10,617,593 B2 | 4/2020 | Wyatt et al. |
| 10,668,305 B2 | 6/2020 | Cheatham, III et al. |
| 10,688,007 B2 | 6/2020 | Wyatt et al. |
| 10,743,621 B2 | 8/2020 | Wyatt et al. |
| 10,791,992 B1 | 10/2020 | Desai et al. |
| 10,893,968 B2 | 1/2021 | Wetzel et al. |
| 11,406,561 B2 | 8/2022 | Pamplin et al. |
| 11,471,368 B2 | 10/2022 | Doraiswamy et al. |
| 11,583,038 B2 | 2/2023 | Doraiswamy et al. |
| 2002/0156401 A1 | 10/2002 | Sherman et al. |
| 2003/0005558 A1 | 1/2003 | Wong |
| 2003/0187366 A1 | 10/2003 | Hashimshony |
| 2005/0043657 A1 | 2/2005 | Couvillon, Jr. |
| 2008/0057526 A1 | 3/2008 | Caduff et al. |
| 2008/0319359 A1 | 12/2008 | Moomiaie-Qajar et al. |
| 2010/0234779 A1 | 9/2010 | Asvadi et al. |
| 2010/0262135 A1 | 10/2010 | Berube |
| 2010/0312160 A1 | 12/2010 | Creighton et al. |

| | | |
|---|---|---|
| 2011/0139835 A1 | 6/2011 | Fikes |
| 2011/0189444 A1 | 8/2011 | Beers |
| 2012/0016210 A1 | 1/2012 | Kim et al. |
| 2012/0065561 A1 | 3/2012 | Ballas et al. |
| 2012/0101417 A1 | 4/2012 | Joseph |
| 2012/0232447 A1 | 9/2012 | Gordon et al. |
| 2013/0030335 A1 | 1/2013 | Norton |
| 2013/0072837 A1* | 3/2013 | Rousso .................. A61H 11/02 |
| | | 601/152 |
| 2013/0267995 A1 | 10/2013 | Voss et al. |
| 2013/0303957 A1 | 11/2013 | Bauerfeind |
| 2013/0345612 A1* | 12/2013 | Bannister .................. A61F 5/02 |
| | | 602/19 |
| 2014/0081187 A1 | 3/2014 | Wyatt et al. |
| 2014/0257156 A1* | 9/2014 | Capra ...................... A43B 3/34 |
| | | 602/5 |
| 2015/0025426 A1 | 1/2015 | Larson et al. |
| 2015/0065930 A1 | 3/2015 | Wyatt et al. |
| 2015/0073318 A1 | 3/2015 | Holschuh et al. |
| 2015/0073319 A1 | 3/2015 | Holschuh et al. |
| 2016/0022528 A1 | 1/2016 | Wyatt et al. |
| 2016/0074234 A1 | 3/2016 | Abichandani et al. |
| 2016/0120733 A1 | 5/2016 | Ishikawa et al. |
| 2016/0193100 A1 | 7/2016 | Toth |
| 2016/0220808 A1 | 8/2016 | Hyde et al. |
| 2016/0331620 A1* | 11/2016 | Kazanchyan ...... A61N 1/36003 |
| 2016/0374886 A1 | 12/2016 | Wyatt et al. |
| 2017/0196347 A1 | 7/2017 | Sawhney et al. |
| 2017/0246073 A1 | 8/2017 | Van-De-Velde |
| 2017/0252252 A1 | 9/2017 | Wyatt et al. |
| 2017/0304136 A1 | 10/2017 | Holschuh et al. |
| 2017/0304139 A1 | 10/2017 | Ross |
| 2017/0312161 A1 | 11/2017 | Johnson et al. |
| 2017/0312165 A1* | 11/2017 | Johnson .............. A61B 5/4842 |
| 2018/0055009 A1 | 3/2018 | Wyatt et al. |
| 2018/0125173 A1 | 5/2018 | Lambert |
| 2018/0177677 A1 | 6/2018 | Pamplin et al. |
| 2018/0192745 A1 | 7/2018 | McDaniel |
| 2018/0214616 A1 | 8/2018 | Muschalek et al. |
| 2018/0242655 A1 | 8/2018 | Holschuh et al. |
| 2019/0274372 A1 | 9/2019 | Rizzo et al. |
| 2020/0000677 A1 | 1/2020 | Pamplin et al. |
| 2020/0154804 A1 | 5/2020 | Huang |
| 2021/0386614 A1* | 12/2021 | Doraiswamy ........ A61H 9/0092 |
| 2022/0022606 A1 | 1/2022 | Doraiswamy et al. |
| 2022/0409123 A1 | 12/2022 | Baldwin et al. |
| 2022/0409437 A1 | 12/2022 | Pamplin et al. |

FOREIGN PATENT DOCUMENTS

| | | |
|---|---|---|
| CN | 105082129 A | 11/2015 |
| CN | 105804960 | 7/2016 |
| KR | 10-1569850 | 11/2015 |
| WO | WO 2013/025481 | 2/2013 |
| WO | WO 2013/149985 | 10/2013 |
| WO | WO 2014/172248 | 10/2014 |
| WO | WO 2016/048827 | 3/2016 |
| WO | WO 2016/077150 | 5/2016 |
| WO | WO 2017/027145 | 2/2017 |
| WO | WO 2018/013188 | 1/2018 |
| WO | WO 2018/150372 | 8/2018 |
| WO | WO 2020/144437 | 7/2020 |
| WO | WO 2021/252770 | 12/2021 |
| WO | WO 2022/002370 | 1/2022 |
| WO | WO 2022/272285 | 12/2022 |
| WO | WO 2022/272287 | 12/2022 |

* cited by examiner

432

432

COMPRESSION GARMENT APPARATUS

CROSS REFERENCE TO RELATED APPLICATIONS

This application claims priority to U.S. Provisional Patent Application No. 63/308,667, filed Feb. 10, 2022, which is incorporated herein by reference in its entirety. Any and all applications, if any, for which a foreign or domestic priority claim is identified in the Application Data Sheet of the present application are hereby incorporated by reference under 37 CFR 1.57.

FIELD

This disclosure relates to compression garments, specifically to compression garments to promote lymphatic circulation.

BACKGROUND

Lymphedema is a medical condition in which excess fluid, such as lymph fluid, collects in the body. In some instances, this excess fluid may collect in a specific area of the body, such as a limb, and cause swelling (i.e., edema). Left untreated, numerous additional symptoms may occur such as infections, fatigue, restricted range of motion, hardening of the skin/tissue, etc.

SUMMARY

Lymphedema may be treated by promoting the drainage of fluid (e.g., lymph) from a region of the body. Disclosed herein are garments and related components (e.g., compression actuator units) that can promote the movement of fluid from an area of the body. The garments and related components can increase lymphatic flow, venous circulation, and/or bodily fluids (arterial, etc.). The garments and related components can be used for muscle recovery (e.g., minimize muscle soreness, reduce post-exercise edema, etc.) For example, a garment, such as a sleeve, may be worn on a limb (e.g., arm, leg, hand, foot, etc.) or any other portion of the body (e.g., torso, head, neck, etc.) of a user. The garment can include one or more compression actuator units, which can also be referred to as actuators, constrictors, etc. The one or more compression actuator units can be actuated to tighten or compress the compression garment around a portion of the body to promote the movement of fluid within the body. The one or more compression actuator units can be actuated simultaneously or in sequence. In some variants, the compression actuator units can be programed to perform a treatment of compression. In some variants, the compression actuator units can be controlled by a wearer or individual assisting with treatment. In some variants, the compression actuator units and/or garment can include a bioimpedance sensing device to sense characteristics, such as volume, of the portion of the body wearing by the garment and/or other sensor(s). In some variants, the bioimpedance sensing device and/or other sensor(s) can provide feedback to the compression actuator units and/or other device in communication with the compression actuator units, which can be used to modify a treatment.

The compression actuator units can facilitate applying compression to an anatomical feature of a user. The compression actuator unit can be actuated to apply compression by the contraction of a wire wrapped around features of the compression actuator unit. In some variants, the compression actuator unit can be actuated by providing a thermal or electrical input to a wire made of a shape memory material. The electrical input from one or more controllers of the compression garment and/or compression actuator units can heat the wire, causing it to contract to actuate the compression actuator unit. The actuation of the compression actuator unit can tighten and/or compress one or more features (e.g., strap(s)) of the compression garment around the user. Alternatively, and/or in combination, compression can be applied via reeling in a wire that is wrapped around the features of the compression actuator unit(s) with a motor, which can actuate the compression actuator unit(s) and/or flex frame assemblies and apply compression to a limb or other anatomical feature of the user. The one or more compression actuator units can incorporate mechanisms, such as levers, to amplify the tightening or compressive forces applied to the user via the contraction of the wire.

In some variants, a garment that can be worn by a user to promote fluid flow within an anatomical feature of the user is disclosed herein. The garment can include a plurality of straps that can be used to secure the garment to an anatomical feature of the user. The garment can include a plurality of compression actuator units. Each of the compression actuator units can include a housing having an interior space. Each of the compression actuator units can include one or more levers mounted within the interior space. The one or more levers can rotate. Each of the compression actuator units can include a slide that can be pulled against the one or more levers to cause the rotation thereof. Each of the compression actuator units can include a sled that can be moved by rotation of the one or more levers. The sled can be coupled to a strap of the plurality of straps of the compression garments. Each of the compression actuator units can include a wire that can be wrapped around portions of the housing and the slide. The wire can be contracted such that the slide is pulled against the one or more levers, causing the one or more levers to rotate to move the sled and pull the strap of the plurality of straps to apply compression to the anatomical feature of the user.

In some variants, the sled can include a D ring that can be coupled with one strap of the plurality of straps.

In some variants, the housing can include a plurality of channels that can receive the wire therein.

In some variants, the housing can include a cover and a base. The exterior surface of the cover can include a channel that can receive the wire therein and an interior surface of the base can include a channel that can receive the wire therein.

In some variants, each of the plurality of compression actuator units can amplify a stroke length from the contraction of the wire by up to one thousand percent.

In some variants, the housing can include a slot disposed in the housing.

The slot can receive the sled therein.

In some variants, the slide can include one or more protrusions that can contact the one or more levers to cause rotation.

In some variants, the slide can include channels that can receive the wire therein.

In some variants, the slide can include a slot that can receive the sled therethrough.

In some variants, the one or more levers can include a first lever with a lowered portion and a second lever with a raised portion. The raised portion of the second lever can pass over the lowered portion of the first lever to avoid interference between the first lever and second lever during rotation.

In some variants, the housing can include a base and a cover. The base can include two inclined surfaces angled about an inflection point. The sled can slide on at least one of the two inclined surfaces.

In some variants, the sled can include an engagement portion that can contact the one or more levers.

In some variants, the garment can include a controller that can apply an electrical input to the wire, raising an internal temperature of the wire such that the wire contracts.

In some variants, the plurality of actuator units can compress an anatomical feature of the user simultaneously or in sequence.

In some variants, a garment that can be worn by a user to promote fluid flow within a body of the user via compressive force is disclosed herein. The garment can include a strap that can be disposed around an anatomical feature of the user. The garment can include an actuator unit. The actuator unit can include a housing that can include an interior space and a plurality of channels that can receive a wire therein such that the wire wraps around features of the housing. The actuator unit can include a first lever disposed within the interior space. The first lever can rotate. The actuator unit can include a slide that can be pulled against the first lever by a contraction of the wire to cause the rotation of the first lever. The actuator unit can include a sled disposed at least partially within the interior space of the housing and coupled to the strap of the compression garment. The sled can be moved by rotation of the first lever to pull the strap to apply compression to the anatomical feature of the user.

In some variants, the housing can include a cover and a base. The plurality of channels can be disposed in an exterior surface of the cover and an interior surface of the base.

In some variants, the compression actuator unit can amplify a stroke length from the contraction of the wire by up to one thousand percent.

In some variants, the housing can include a slot disposed in the housing.

The slot can receive the sled therein.

In some variants, the slide can include one or more protrusions that can contact the first lever to cause rotation.

In some variants, the slide can include channels that can receive the wire therein.

In some variants, the slide can include a slot that can receive the sled therethrough.

In some variants, the actuator unit can include a second lever disposed within the interior space. The slide can be pulled against the second lever by the contraction of the wire to cause the rotation of the second lever. The first lever can include a lowered portion and the second lever can include a raised portion. The raised portion of the second lever can pass over the lowered portion of the first lever to avoid interference between the first lever and second lever during rotation.

In some variants, the housing can include a base and a cover. The base can include two inclined surfaces angled about an inflection point. The sled can slide on at least one of the two inclined surfaces.

In some variants, the sled can include an engagement portion that can contact the first lever and second lever.

In some variants, the actuator unit can include a controller that can apply an electrical input to the wire, raising an internal temperature of the wire such that the wire contracts.

In some variants, an actuator unit is disclosed herein. The actuator unit can include a housing having an interior space and a plurality of channels that can receive a wire therein such that the wire wraps around features of the housing. The actuator unit can include one or more levers disposed within the interior space. The one or more levers can rotate. The actuator unit can include a slide that can be pulled against the one or more levers by a contraction of the wire to cause the rotation of the one or more levers. The actuator unit can include a sled disposed at least partially within the interior space of the housing. The sled can be moved by rotation of the one or more levers. The one or more levers can amplify a pull force generated by the contraction of the wire. The actuator unit can be incorporated into a compression garment that can be worn by a user.

In some variants, a garment can be worn on an anatomical feature of a user to promote fluid flow within the anatomical feature. The garment can include a strap that can be wrapped around the anatomical feature of the user. The garment can include a compression actuator unit. The compression actuator unit can include a housing having an internal cavity. The compression actuator unit can include a sled disposed within the internal cavity. The sled can be coupled to the strap. The compression actuator unit can include one or more levers rotatably coupled to the housing and disposed within the internal cavity. The compression actuator unit can include a slide disposed at least partially outside the internal cavity. The compression actuator unit can include a wire wrapped around portions of the housing and the slide. The wire can be contracted to pull the slide inward toward the housing to push against the one or more levers to cause the one or more levers to rotate to push against and translate the sled within the internal cavity, pulling the strap to apply compression to the anatomical feature of the user.

In some variants, the housing can include a plurality of channels disposed in external surfaces to hold the wire.

In some variants, the slide can include a plurality of channels disposed in a portion of the slide disposed outside of the internal cavity. The plurality of channels can hold the wire.

In some variants, the portion of the slide disposed outside of the internal cavity can include a curved surface.

In some variants, the rotation of the one or more levers can displace the sled a greater distance than the slide.

In some variants, the sled can move a distance ten times greater than the slide.

In some variants, the one or more levers can include a first lever and a second lever.

In some variants, the first and second levers can be disposed in an overlapping arrangement.

In some variants, the first and second levers can be rotated into an X arrangement.

In some variants, the one or more levers can include a free end having rounded features.

In some variants, the compression actuator unit can include a first rod disposed in a slot of the sled. The strap can loop around the first rod to couple the strap to the sled.

In some variants, the compression actuator unit can include a second rod.

The strap can loop around the second rod before exiting the housing.

In some variants, the second rod can be biased by one or more springs in a direction that is opposite a direction of the translation of the sled within the internal cavity upon contraction of the wire.

In some variants, the compression actuator unit can include a controller that can apply an electrical current to the wire.

In some variants, the garment can include a plurality of straps and a plurality of compression actuator units.

In some variants, an actuator unit is disclosed herein. The actuator unit can include a housing having an internal cavity. The actuator unit can include a sled disposed within the internal cavity. The sled can be coupled to a strap wrapped around an anatomical feature of a user. The actuator unit can include one or more levers rotatably coupled to the housing and disposed within the internal cavity. The actuator unit can include a slide disposed at least partially outside the internal cavity. The actuator unit can include a wire wrapped around portions of the housing and the slide. The wire can be contracted to pull the slide inward toward the housing to push against the one or more levers to cause the one or more levers to rotate to push against and translate the sled within the internal cavity, pulling the strap to apply compression to the anatomical feature of the user. The wire can be contracted via reeling in the wire with a motor. The wire can be contracted via the application of an electrical current.

In some variants, the housing can include a plurality of channels disposed in external surfaces to hold the wire.

In some variants, the slide can include a plurality of channels disposed in a portion of the slide disposed outside of the internal cavity. The plurality of channels can hold the wire.

In some variants, the portion of the slide disposed outside of the internal cavity can include a curved surface.

In some variants, the rotation of the one or more levers can displace the sled a greater distance than the slide.

In some variants, the sled can move a distance ten times greater than the slide.

In some variants, the one or more levers can include a first lever and a second lever.

In some variants, the first and second levers can be disposed in an overlapping arrangement.

In some variants, the first and second levers can be rotated into an X arrangement.

In some variants, the first and second levers can be arranged in a scissor arrangement.

In some variants, the one or more levers can include free ends having rounded features.

In some variants, the compression actuator unit can include a first rod disposed in a slot of the sled. The strap can loop around the first rod to couple the strap to the sled.

In some variants, the compression actuator unit can include a second rod.

The strap can loop around the second rod before exiting the housing.

In some variants, the second rod can be biased by one or more springs in a direction that is opposite a direction of the translation of the sled within the internal cavity upon contraction of the wire.

In some variants, the compression actuator unit can include a controller that can apply an electrical current to the wire.

In some variants, an actuator unit is disclosed herein. The actuator unit can include a housing that can include a spiral channel that can receive a wire therein. The actuator unit can include a D ring that can be coupled with a strap wrapped around an anatomical feature of a user. The D ring can be coupled to the wire. Upon contraction of the wire, the D ring can be translated toward the housing to tension the strap to apply compression to the anatomical feature of the user. In some variants, the D ring can be biased away from the housing via one or more springs.

In some variants, the actuator unit can include a controller configured to apply an electrical current to the wire to contract the wire.

In some variants, the wire can be contracted via application of an electrical current to the wire.

In some variants, the wire can be made of a shape memory material.

In some variants, an actuator unit is disclosed herein. The actuator unit can include a housing having an internal cavity. The actuator unit can include a spool that can hold a strip of material thereon. The spool can be disposed in the housing and the strip of material can be wrapped around an anatomical feature of a user. The actuator unit can include a motor that can rotate the spool to reel in the strip of material to apply compression to the anatomical feature of the user.

In some variants, the spool can be coupled with a gear and the motor can rotate a motor gear interfaced with the gear to reel in the strip of material.

In some variants, the actuator unit can include a second motor and a second spool disposed in the housing that can hold the strip of material thereon. The second motor can rotate the second spool to reel in the strip of material to apply compression to the anatomical feature of the user.

In some variants, a second motor and a second spool can be disposed in the housing that can hold a second strip of material thereon. The second motor can rotate the second spool to reel in the second strip of material to apply compression to the anatomical feature of the user.

In some variants, the second spool can be coupled with a second gear and the second motor can rotate a second motor gear interfaced with the second gear to rotate the second spool.

In some variants, the garment and/or actuator unit can increase venous circulation, increase circulation of bodily fluids, assist in muscle recover, reduce muscle soreness, and/or reduce post-exercise edema.

In some variants, a flex frame assembly is disclosed herein. The flex frame can include a base. The flex frame can include one or more springs. The flex frame can include a plurality of guide structures. Multiple guide structures of the plurality of guide structures can be disposed on the base and one guide structure of the plurality of guide structures can be connected to the one or more springs such that the one or more springs is disposed between the one guide structure and the base. The flex frame can include a wire wrapped around the plurality of guide structures. The wire can contract, pulling the one guide structure toward the base to deflect the one or more springs and shorten the flex frame assembly.

In some variants, the flex frame assembly can be incorporated into a compression garment that can be worn on an anatomical feature of the user. The shortening of the flex frame assembly can apply a compressive force to the anatomical feature of the user.

In some variants, the one or more springs can include four springs arranged in series between the base and the one guide structure.

In some variants, the wire can be contracted via application of an electrical current to the wire.

In some variants, the wire can be made of a shape memory material.

In some variants, the flex frame assembly, upon contraction of the wire, can apply compression to an anatomical feature of the user to increase venous circulation, increase circulation of bodily fluids, assist in muscle recover, reduce muscle soreness, and/or reduce post-exercise edema.

Neither the preceding summary nor the following detailed description purports to limit or define the scope of protection. The scope of protection is defined by the claims. Furthermore, reference is made herein to treating lymphedema. However, one of skill in the art will understand, after reviewing the entirety of this disclosure, that the devices (e.g., garments, compression actuator unit(s), etc.), methods, systems, components, etc. described herein may be used for other purposes besides treating lymphedema. For example, the garments described herein can be worn by athletes to promote circulation to foster recovery after physical activity. Additionally, one of ordinary skill in the art will understand, after reviewing the entirety of this disclosure, that the devices (e.g., garments, compression actuator unit(s), etc.), methods, systems, components, etc. described herein can be used by both humans and animals.

BRIEF DESCRIPTION OF THE DRAWINGS

The abovementioned and other features of the embodiments disclosed herein are described below with reference to the drawings of the embodiments. The illustrated embodiments are intended to illustrate, but not to limit, the scope of protection. Various features of the different disclosed embodiments can be combined to form further embodiments, which are part of this disclosure.

FIGS. 21A and 20B illustrate various views of a compression actuator unit.

DETAILED DESCRIPTION

Although certain embodiments and examples are described below, this disclosure extends beyond the specifically disclosed embodiments and/or uses and obvious modifications and equivalents thereof. Thus, it is intended that the scope of this disclosure should not be limited by any particular embodiments described below. Furthermore, this disclosure describes many embodiments in reference to treating lymphedema, but as described herein, any embodiment and modifications or equivalents thereof should not be limited to treating lymphedema.

The compression garments systems, apparatuses, and methods disclosed herein can be used and/or modified for use with systems and methods described in U.S. Pub. No. 2020/0000677 to Pamplin et al., filed Aug. 15, 2019, which is hereby incorporated by reference in its entirety. Compression garment systems can include one or more compression actuator units, which can also be referred to as actuators, constrictors, etc. The one or more compression actuator units can be actuated to tighten or compress the compression garment around a portion of the body to promote the movement of fluid within the body. The compression actuator units can apply compression via a wire wrapped around features thereof. In some variants, the compression can be applied via providing a thermal or electrical input to a wire made of a shape memory material. The wire can be made of shape memory materials such as alloys, nickel-titanium (Nitinol) alloy (preferred), and/or copper-aluminum-nickel alloy or any other alloy (e.g., Fe—Mn—Si, Cu—Zn—Al, Cu—Al—Ni, etc.) or shape memory polymers and composites, configured to morphologically change in response to a stimulus (e.g., temperature change). The electrical input from one or more controllers of the compression garment and/or compression actuator units can heat the wire, causing it to contract to actuate the compression actuator unit. The actuation of the compression actuator unit can tighten and/or compress one or more features (e.g., strap(s)) of the compression garment around the user. Alternatively, and/or in combination, compression can be applied via reeling in a wire that is wrapped around the features of the compression actuator unit(s) with a motor, which can actuate the compression actuator unit(s) and apply compression to a limb or other anatomical feature of the user. The one or more compression actuator units can incorporate mechanisms, such as levers, to amplify the contraction of the wire.

Figure 1:
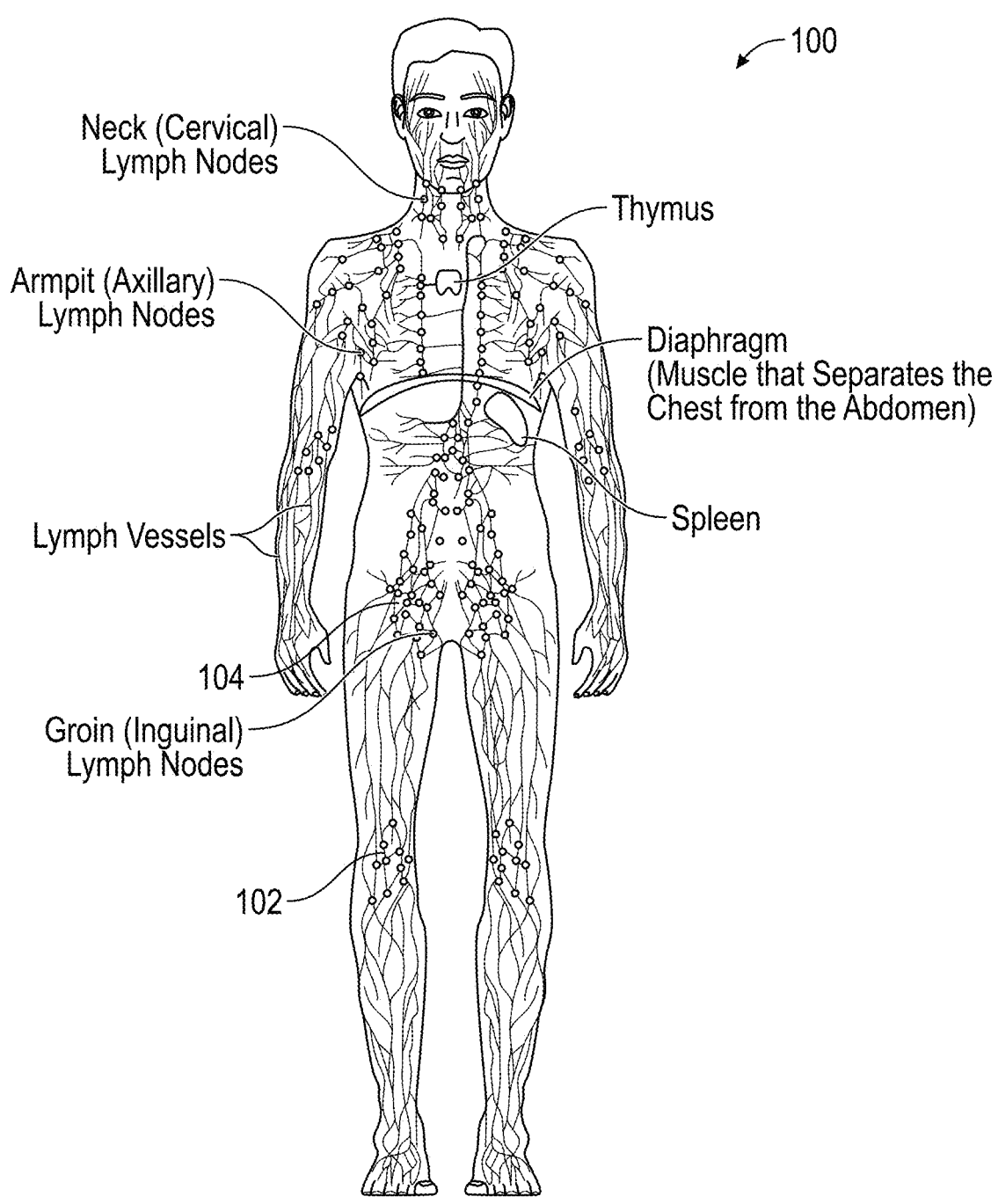
FIG. 1 illustrates a lymphatic system of a body.

FIG. 1 illustrates a lymphatic system of a body 100 of a user. The lymphatic system is an organ system that is part of both the circulatory and immune systems. The lymphatic system includes a network of lymphatic vessels or channels 102 and nodes 104, among other features, that help to recirculate blood and/or lymph through the human body. As described herein, lymphedema is a medical condition in which excess fluid, such as lymph fluid, collects in an area of the body, such as a limb, and causes swelling (i.e., edema). Left untreated, numerous additional detrimental symptoms may develop.

Figure 2A:
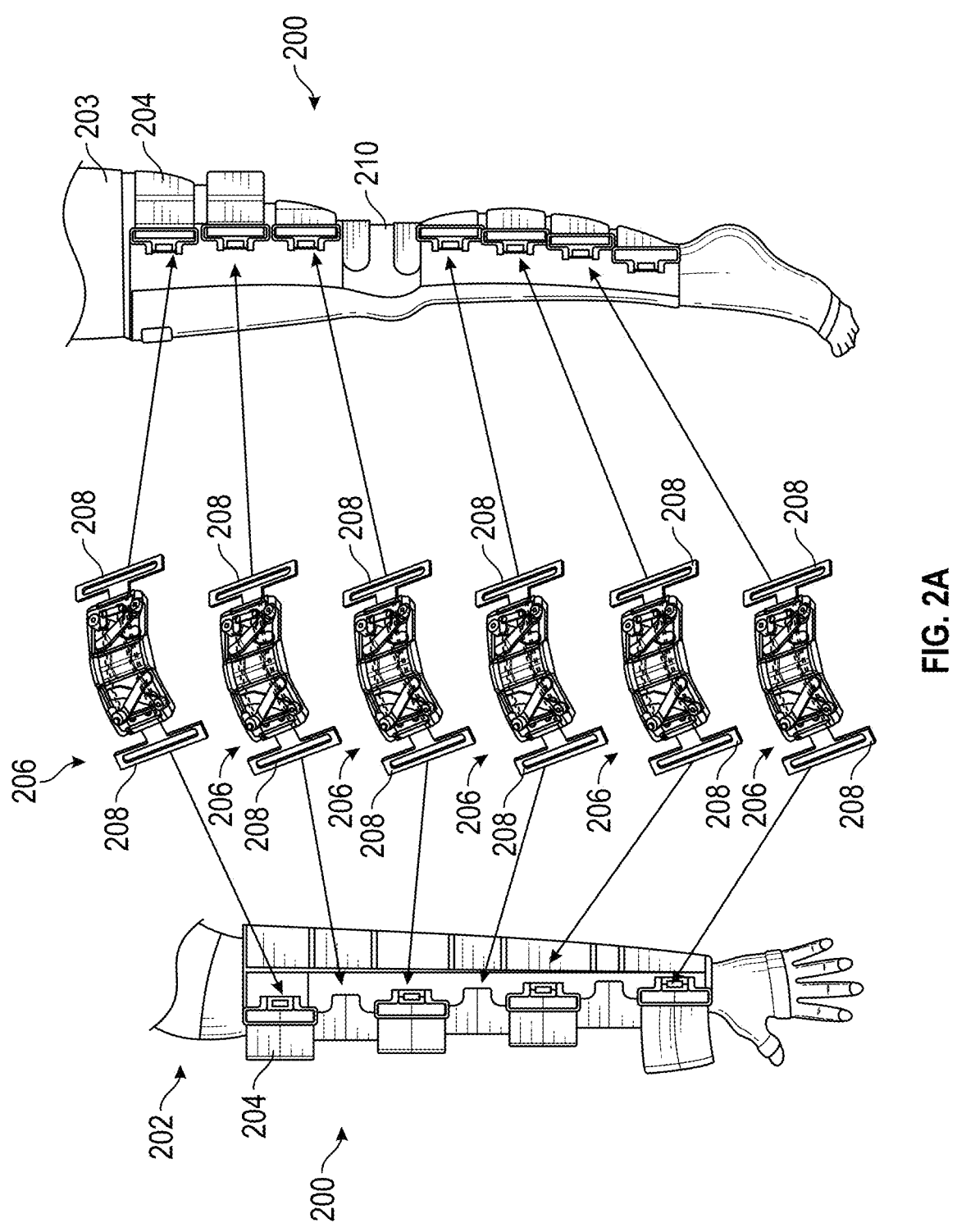
FIG. 2A illustrates a compression garment with a plurality of compression actuator units.

FIG. 2A illustrates a compression garment 200 that can be used to move fluid within the body, which can include treating lymphedema. The compression garment 200, as shown, is disposed on a limb, e.g., arm 202 and leg 203. The compression garment 200, however, can be worn on any anatomical feature of the user. The compression garment 200 can include one or more straps 204 to attach the compression garment 200 to the user. The one or more straps 204 and/or other feature of the compression garment 200 can be coupled to the compression actuator units 206 and/or compression actuator unit 406 and wrapped around an anatomical feature of the user. For example, the compression actuator unit 206 can include one or more D rings 208, e.g., two. A strap 204 can be coupled to (e.g., threaded through) the D rings 208. The actuation of the compression actuator unit 206 can move the D rings 208 toward each other, causing the strap 204 to be tensioned to apply compression to the limb or other anatomical feature of the user.

The compression garment 200 can include one or more compression actuator units 206. The one or more compression actuator units 206 can be distributed along a length of the compression garment 200 such that, when worn, the compression actuator units 206 are distributed along the length of the limb and/or other anatomical feature of the user. The compression actuator units 206 can apply a compressive force simultaneously, in sequence, and/or in another configuration. For example, in some instances, fluid may collect in distal portions of a user's limb. In some variants, the compression actuator units 206 can apply a compressive force to the limb in sequence by beginning with a distally positioned compression actuator unit 206 and then sequentially actuating proximal compression actuator units 206, which can effectively move fluid toward the trunk of the user. In some variants, the compression garment 200 can include flexible region(s) 210, which can be devoid of compression actuator units 206. The flexible regions 210 can be configured to be positioned around a joint (e.g., ankle, wrist, knee, elbow, etc.) of the user to facilitate increased movement. In some variants, the flexible regions 210 can be made of a flexible material.

Figure 2B:
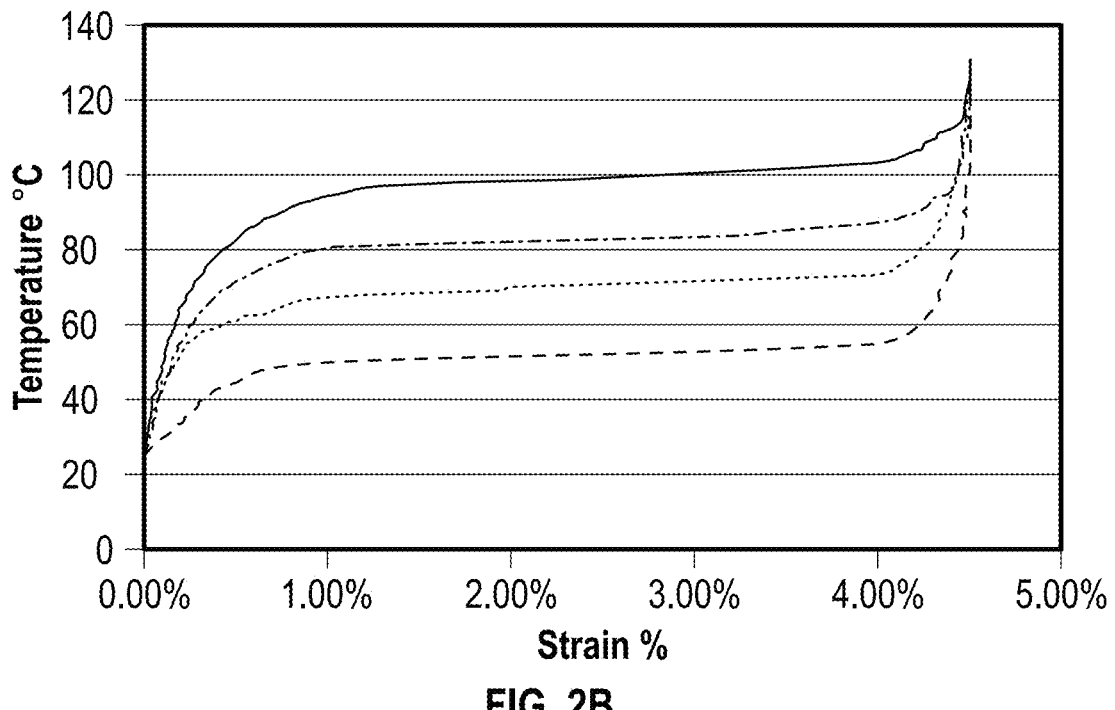
FIG. 2B illustrates a graph illustrating an internal temperature in Celsius of a Nitinol alloy wire and corresponding strain percentage.

As described herein, the compression actuator unit 206 can be actuated via a variety of techniques. In some variants, the compression actuator units 206 can be actuated by applying heat and/or an electrical input to wires or the like made of a shape memory material, such as Nitinol, which can result in the contraction of the wires. The precise controlling of an internal temperature of the wires can allow the compression actuator units 206 to provide a known pull force, e.g., tensioning force, to apply a predetermined graduated pressure to the user. FIG. 2B illustrates a graph illustrating an internal temperature in Celsius of a Nitinol alloy wire and corresponding strain percentage.

Figure 3A:
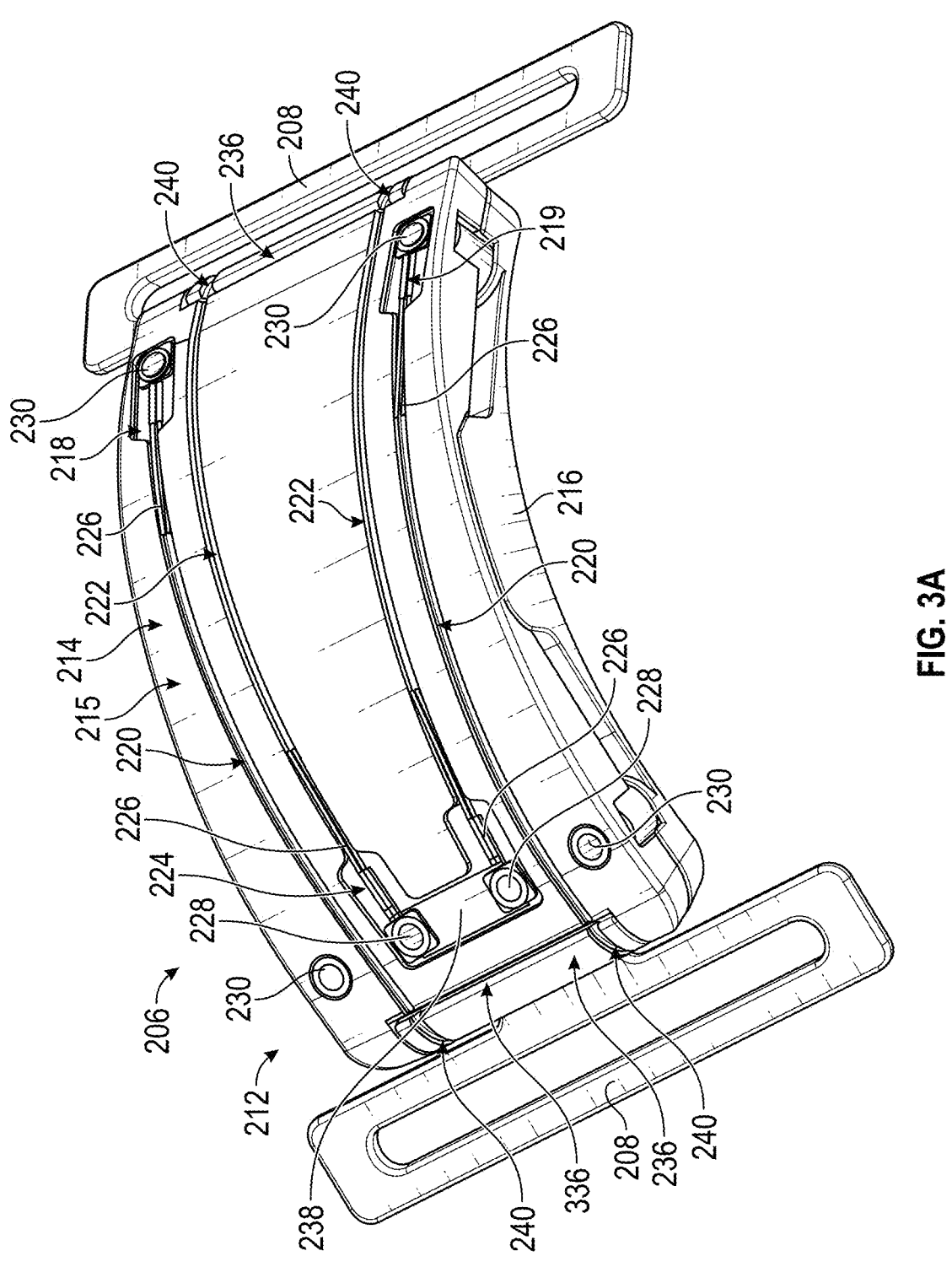
FIGS. 3A and 3B illustrate views of a compression actuator unit.
Figure 3B:
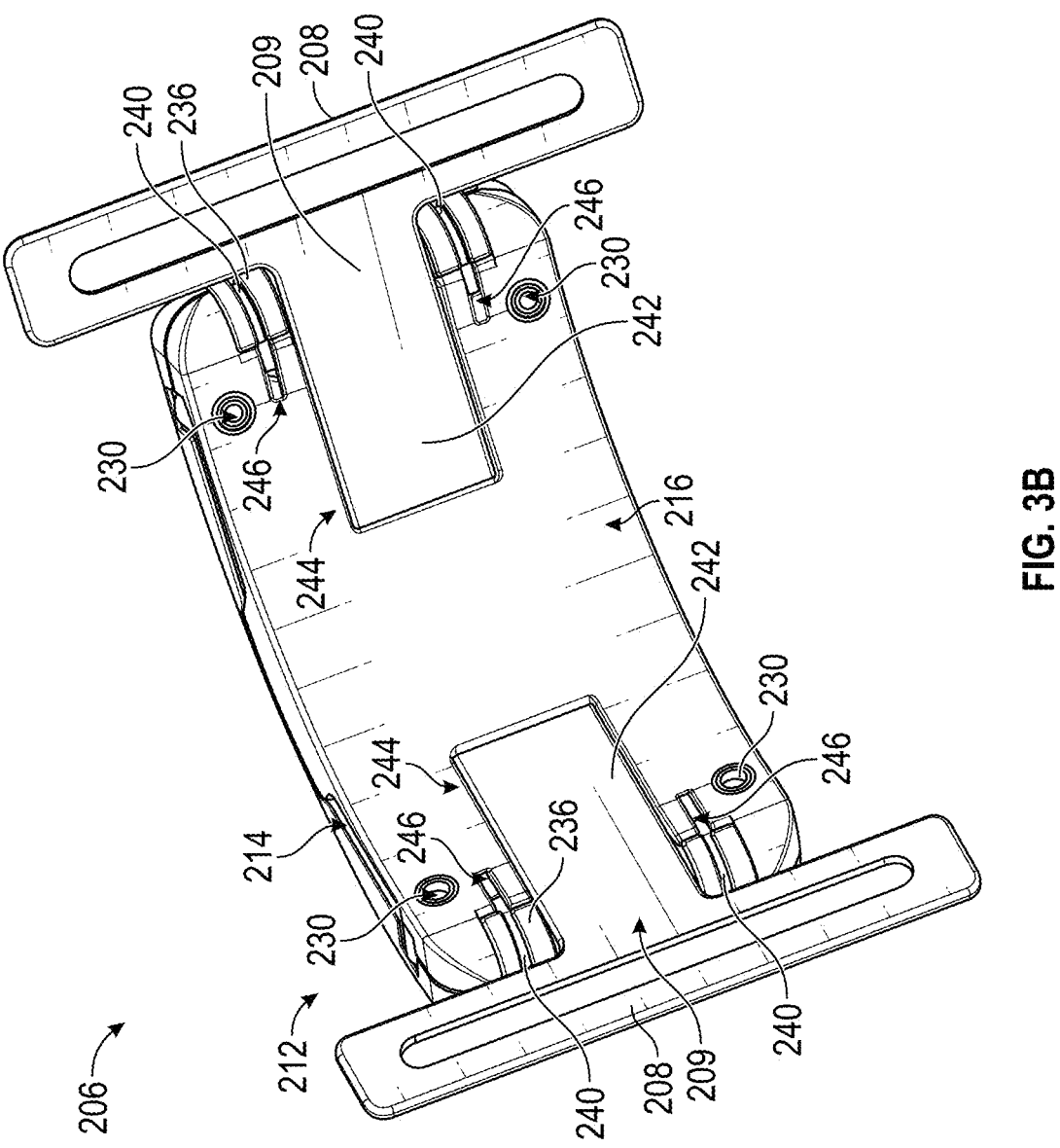

FIGS. 3A and 3B illustrate various views of a compression actuator unit 206, which can also be referred to as an actuator unit, actuator, constrictor, tensioning unit, etc. The compression actuator unit 206 can include a curved periphery and/or profile, which can correspond to the curved surface of a user's limb and/or other anatomical feature. The compression actuator unit 206 can include a housing 212. The housing 212 can include a cover 214 and a base 216, which can be coupled together via a plurality of fasteners 230, e.g., rivets, bolts, screws, or the like, to house one or more items therein.

The cover 214 can include an exterior surface 215, which can include one or more features to house a wire or the like therein. For example, the exterior surface 215 can include a recess 224 therein. The recess 224 can house a bridge 238 upon which one or more leads 226 (e.g., two) are disposed. The leads 226 can be shape memory alloy (SMA) leads. The SMA lead 226 can be the beginning portion of a wire or coupled to a wire or the like, such as a shape memory material and/or alloy wire. The SMA lead 226 can be connected to the bridge 238 via one or more fasteners 228, which can be used to couple the bridge 238 to the cover 214.

The SMA leads 226 can be connected to a controller, e.g., microcontroller, that can apply an electrical input and/or heat thereto, resulting in the heating of the wire or the like. The heating of the wire can contract the wire, as described herein.

The exterior surface 215 can include one or more first channels or grooves 222 therein that extend from the recess 224. The wires or the like can be routed from the SMA leads 226 through the first channels 222 to a first slide 236, which can also be referred to as a slider. The first slide 236 can be disposed between the cover 214 and base 216. The first slide 236 can extend out from inside the housing 212. The wires or the like can be routed around the first slide 236 via channels or grooves 240 therein and through first openings 246 in the base 216, as illustrated in FIG. 3B. The wires or the like can be routed through an interior of the housing 212 via channels or grooves disposed on an interior surface of the base 216 and exit the interior of the housing 212 via second openings 246 disposed opposite the first openings 246. The wire or the like can then be routed around a second slide 236, disposed opposite the first slide 236, via channels or grooves 240 and into second channels 220, as illustrated in FIG. 3A. The wires or the like can then be routed through the second channels 220 and terminate at the SMA lead 226 fastened via the fastener 230 in recesses 218 disposed in the exterior surface 215 of the cover 214. The compression actuator unit 206 can include one or more wires routed in similar manners. As illustrated, the compression actuator unit 206 can be used with at least two wires or the like. One wire is routed from the SMA lead 226 disposed in the recess 224, through the first channel 222, around the first slide 236 via the channel 240, into the interior of the housing 212 via a first opening 246 in the base 216, through a channel disposed on an interior surface of the base 216, out of the interior of the housing 212 via the second opening 246, around the second slide 236 via the channel 240, and through the second channel 220 to the SMA lead 226 disposed in the recess 218. Another wire can be routed similarly, which can be in a mirrored configuration as illustrated.

When electrical input is applied to the wires, the wires can contract, moving the slides 236 towards each other and/or into the housing 212. Gaps 336 can be disposed between the slides 236 and the cover 214, and as the wires contract, the gap 336 can be decreased. In some variants, the slides 236 can move further into the housing 212 as the wires contract. The movement of the slides 236 can cause corresponding movement of the D rings 208 inward, which can tension a strap and/or other feature of the compression garment attached to the D rings 208 to apply a compressive force to the limb or other anatomical feature of the user.

In some variants, the D rings 208 can be incorporated into sleds 209. The sleds 209 can include D rings 208 disposed on one end that extends outside the housing 212 and engagement portions disposed on an opposite end disposed inside the housing 212. The sleds 209 can include tongues 242 that extend from the D rings 208 to the engagement portions via gaps 244 in the base 216, as shown in FIG. 3B.

The compression actuator unit 206 can include a plurality of levers, which can be disposed in the housing 212. The slides 236 can contact, directly or indirectly, and move the plurality of levers. The levers, in turn, can contact, directly or indirectly, and move the engagement portions of the sleds 209 disposed inside of the housing 212, resulting in the movement of the D rings 208 toward each other. The levers can amplify the movement of the slides 236 to move the D rings 208 a greater distance than the slides 236. The total movement of the D rings 208 can be referred to as a stroke length, which can be at least zero to two hundred millimeters. The levers can amplify the stroke length compared to the movement of the slide 236 by up to one thousand percent, which can enable the compression actuator unit 206 to generate up to at least two hundred Newtons of pull force and/or two hundred mmHg of pressure.

Figure 4A:
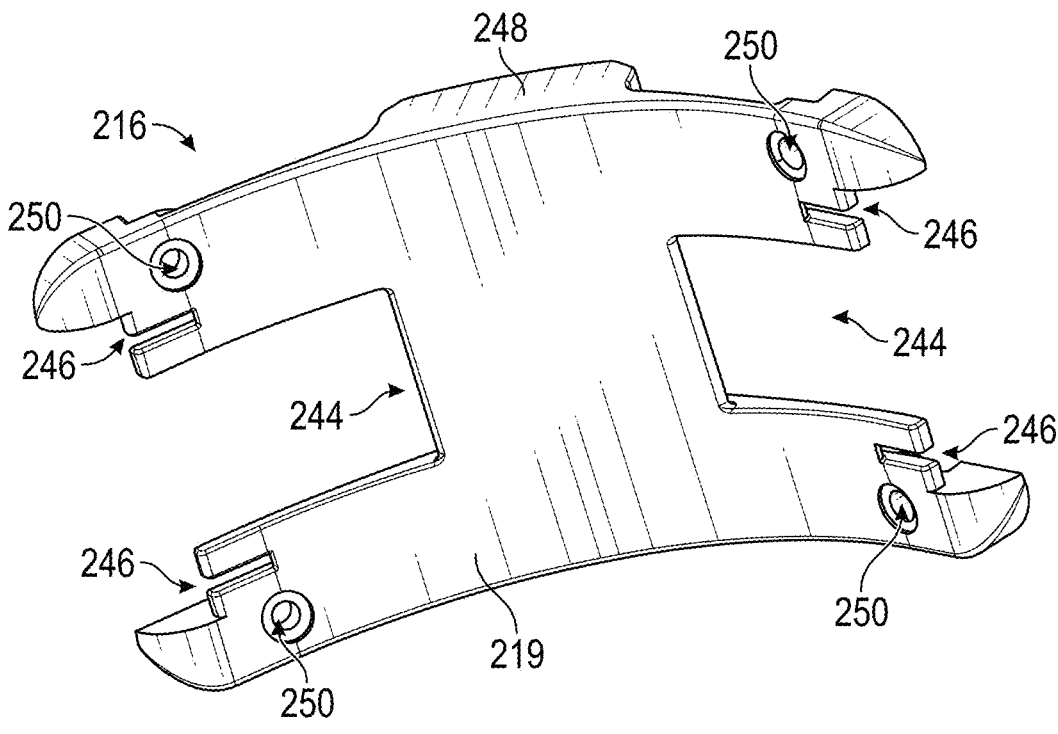
FIGS. 4A and 4B illustrate views of the base of the compression actuator unit.
Figure 4B:
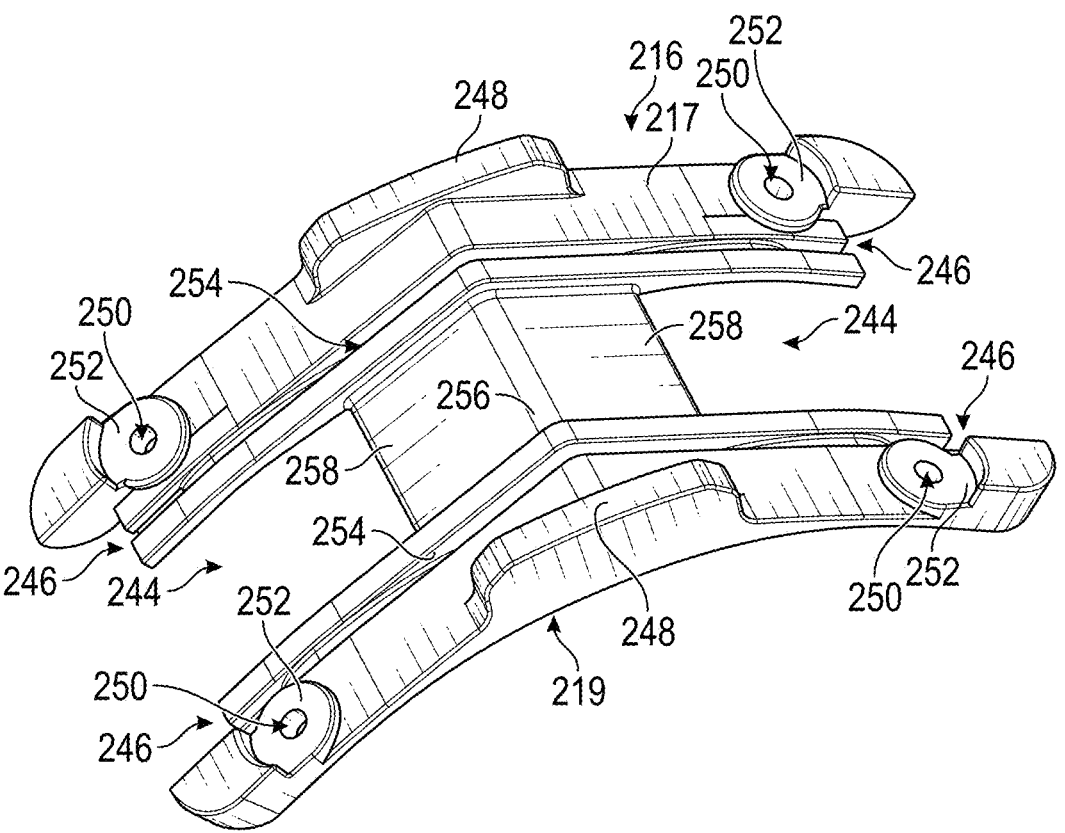

FIGS. 4A and 4B illustrate various views of the base 216. As illustrated in FIG. 4A, the base 216 can have a curved exterior face 219, which can be configured to curve around the anatomy (e.g., limb) of the wearer. As illustrated in FIG. 4B, the base 216 can have an interior face 217. The interior face 217 can include two inclined surfaces that are angled to each other about an inflection point 256. In some variants, the base 216 can be in a mirrored configuration relative to the inflection point 256. The interior face 217 can include one or more (e.g., two) channels 254 therein. The channel 254 can connect openings 246 disposed on opposing sides of the base 216, which can enable a wire or the like to be routed from a first opening 246 through a channel 254 to a second opposite opening 246.

The base 216 can include one or more tabs 248, which can also be referred to as protrusions, side walls, flanges, etc. The tabs 248 can be configured to be inserted into corresponding gaps in the cover 214 to help position the cover 214 relative to the base 216 during assembly and/or prevent movement between the base 216 and cover 214 during use. The tabs 248 can extend from the interior face 217. The tabs 248 can be centered along the inflection point 256 between the two inclined surfaces of the interior face 217.

The base 216 can include a plurality of mounts 252. The plurality of levers can be coupled to the base 216 at the plurality of mounts 252 via the fasteners 230. For example, the mounts 252 can include a plurality of holes 250. The levers can have holes that are coaxially aligned with the holes 250 of the mounts 252. The fasteners 230 can be inserted through the cover 214, through the holes of the levers, and through the holes 250 of the mount 252 to couple the base 216, levers, and cover 214. In some variants, the holes 250 are threaded such that the fasteners 230 can be secured via a threaded connection. In some variants, the fasteners fastener 230 can be rivets that can be secured in place. In some variants, nuts can be used to secure the fasteners 230 in place.

The base 216 can include slots 258. One slot 258 can be disposed on one inclined surface of the interior face 217, while another slot 258 can be disposed on the other inclined surface of the interior face 217. The slots 258 can have a width corresponding to a width of the tongues 242 of the sleds 209 such that the tongues 242 can be received therein. As described herein, the tongues 242 of the sleds 209 can extend through the gaps 244 of the base 216 and into the slots 258 disposed on the inclined surfaces of the interior face 217. During actuation, the tongues 242 of the sleds 209 can slide within the slots 258.

Figure 5A:
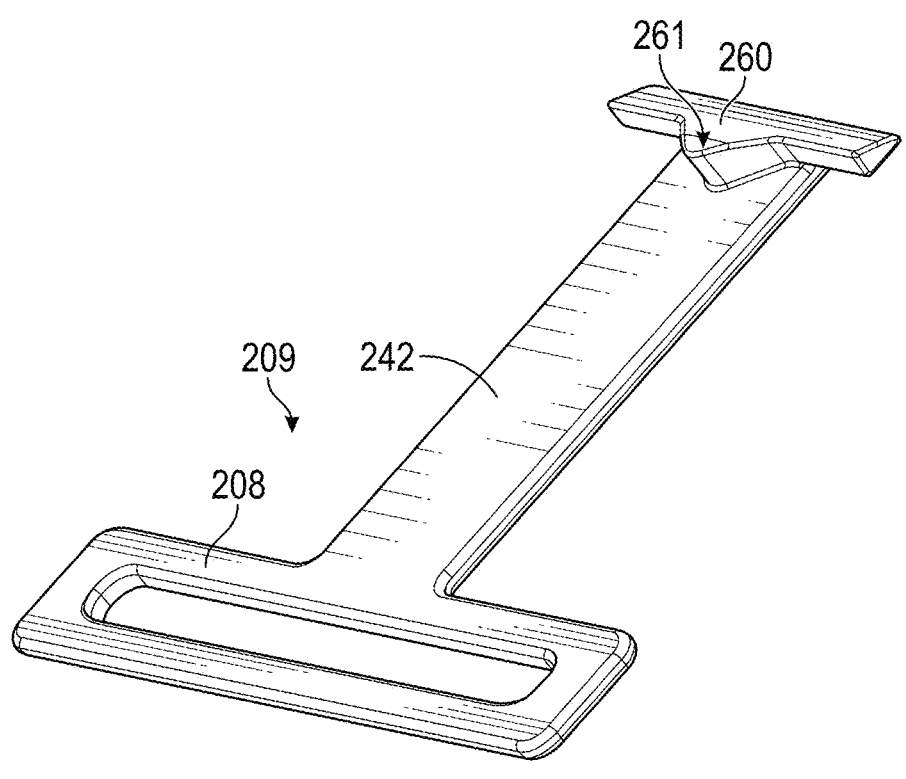
FIGS. 5A and 5B illustrate views of a sled of the compression actuator unit.
Figure 5B:
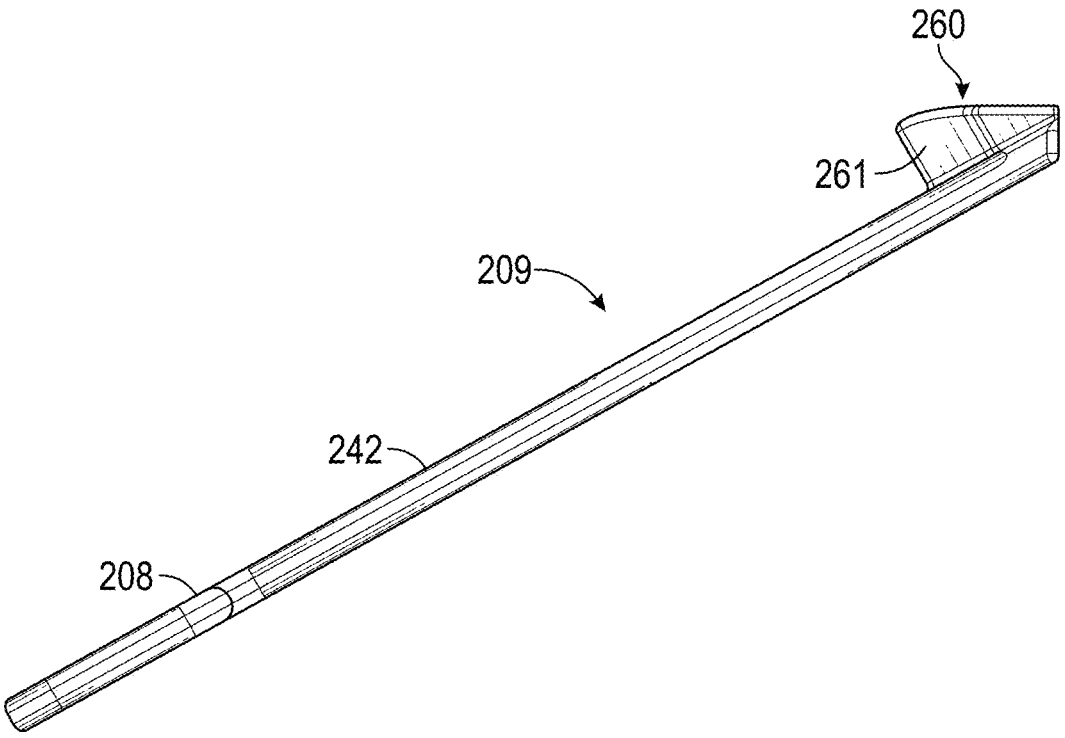

FIGS. 5A and 5B illustrate various views of the sleds 209. As described herein, the sled 209 can have D rings 208, which can also be referred to as rings, couplers, interfaces, etc. The D rings 208 can be coupled to a strap or other feature of the compression garment that is configured to be tensioned or pulled to compress an anatomical feature of the user. In some variants, a strap can be routed through the D rings 208. The sleds 209 can include engagement portions 260, which can also be referred to as anchors, contacts, hooks, catches, etc. The levers, described herein, can contact and move the engagement portions 260 to slide the sled 209 within the slots 258. The engagement portions 260 can include protrusions 261, which can be angled protrusions, that can help to provide a secure contact surface for the levers. A tongue 242 can extend between the engagement portion 260 and the D ring 208.

Figure 6A:
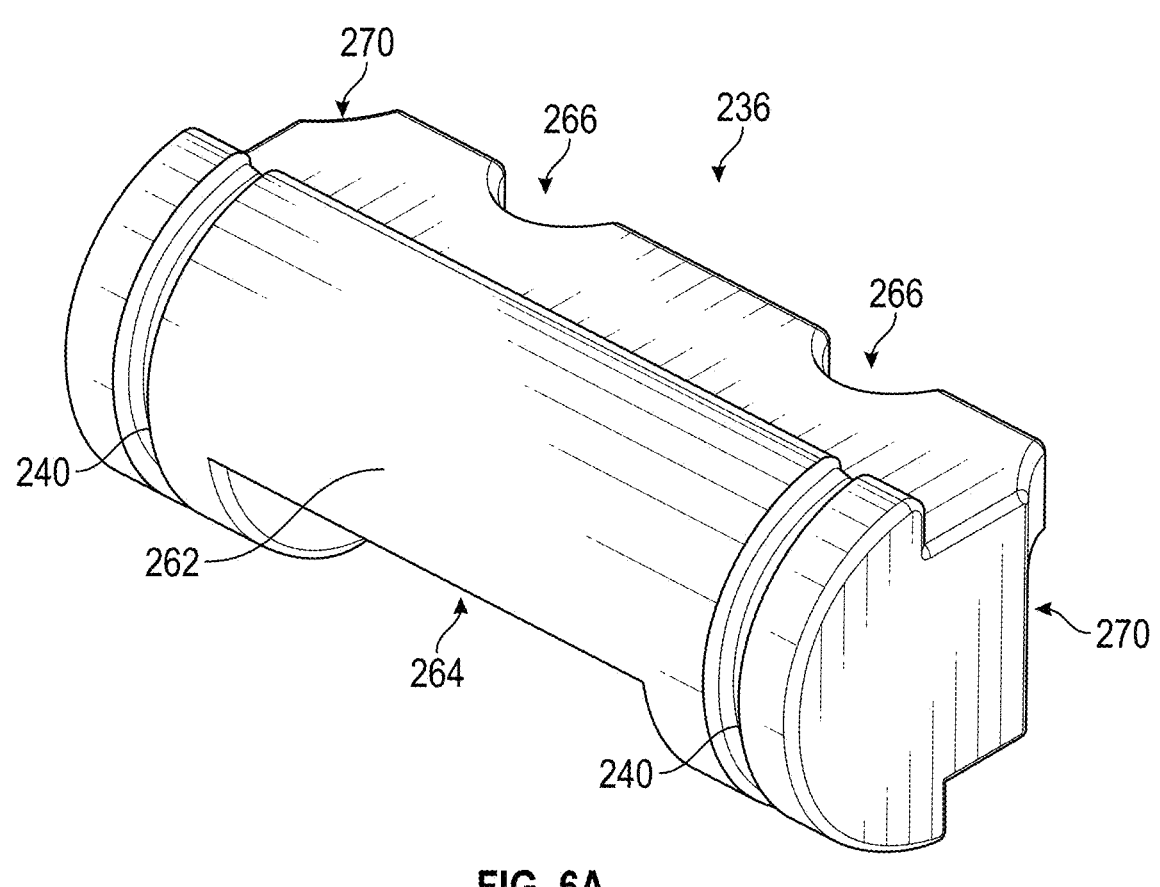
FIGS. 6A and 6B illustrate views of a slide of the compression actuator unit.
Figure 6B:
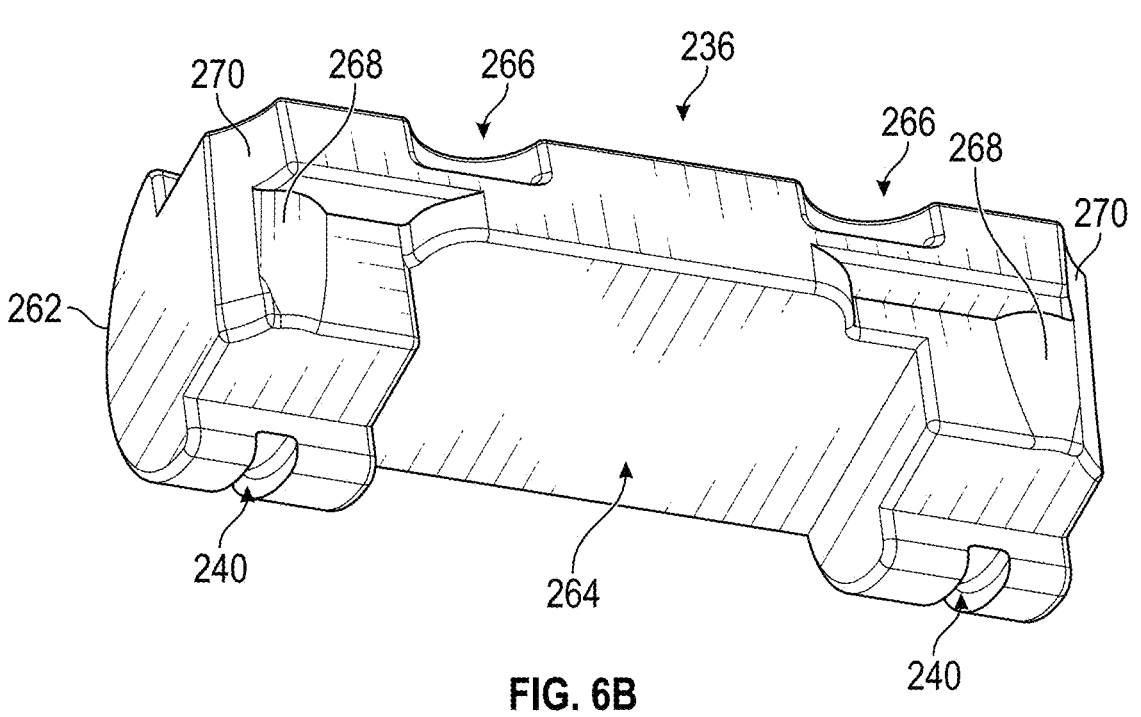

FIGS. 6A and 6B illustrate various views of the slide 236. The slide 236 can include a curved surface 262 that can extend out of the housing 212 when the slide 236 is disposed between the cover 214 and the base 216, as described herein. The channels 240, through which the wires or the like can be routed, can be disposed in the curved surface 262. The slide 236 can include a slot 264 which can be sized to allow the tongue 242 therethrough. The slide 236 can include one or more protrusions 268, which can also be referred to as bumps, raised surfaces, etc., that can contact and push against a portion of the levers during actuation. During actuation, the wires or the like can contract, pulling the slides 236 inward such that the protrusions 268 contact and push the levers. The levers can rotate to push against the engagement portions 260 of the sled 209, pulling the D ring 208 inward to tension the straps and/or other features of the compression garments attached thereto. The slide 236 can include curved recesses 270 to provide clearance for the levers to rotate during actuation. The slide 236 can include gaps or recesses 266 to provide clearance for the fasteners 228.

Figure 7A:
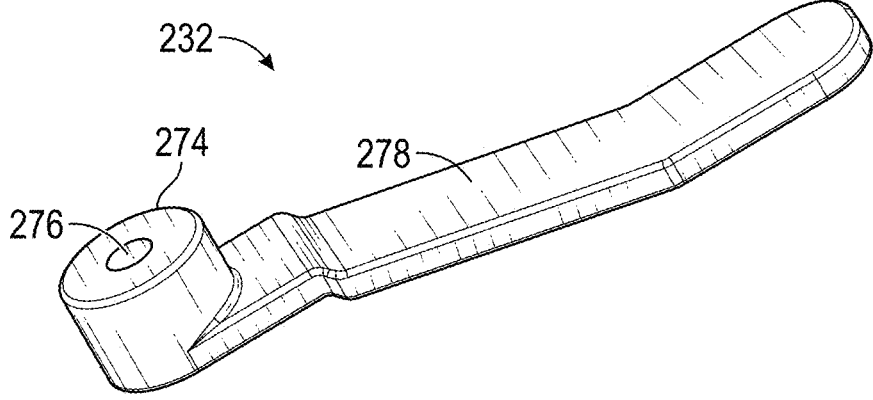
FIGS. 7A and 7B illustrate views of a first lever of the compression actuator unit.
Figure 7B:
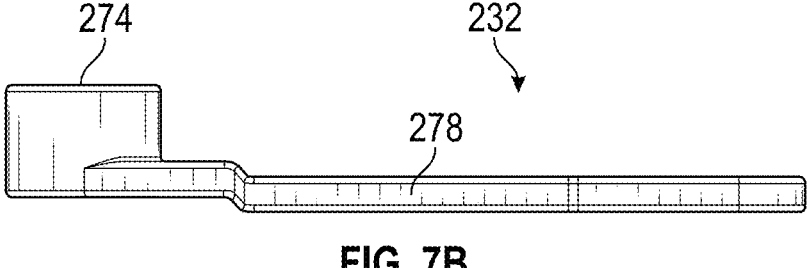

FIGS. 7A and 7B illustrate various views of a first lever 232, which can also be referred to as an arm, limb, member, etc. The first lever 232 can include a joint 274, which can be mounted on the mounts 252 of the base 216. The joint 274 can have a hole 276 therethrough to facilitate coupling to the base 216 and the cover 214 via the fasteners 230. The first lever 232 can include a lowered portion 278, which can enable the first lever 232 and a second lever 234, described herein, cross over each other without interference. The first lever 232 can extend from the joint 274 at an angle.

Figure 8A:
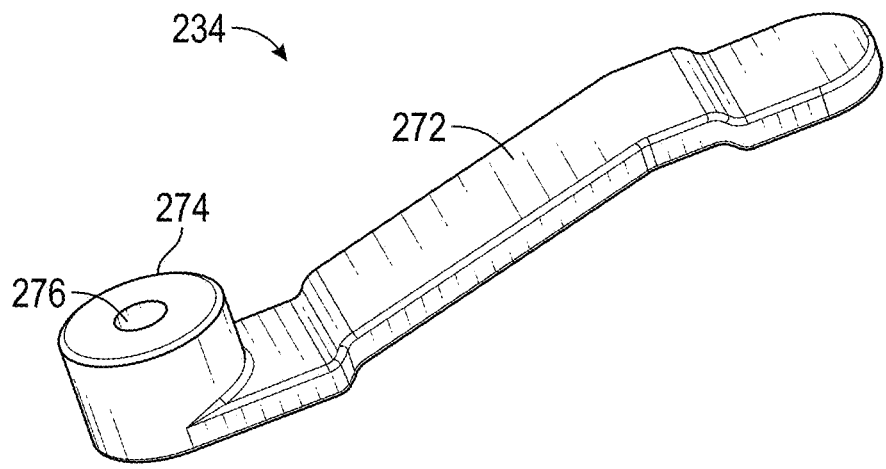
FIGS. 8A and 8B illustrate views of a second lever of the compression actuator unit.
Figure 8B:
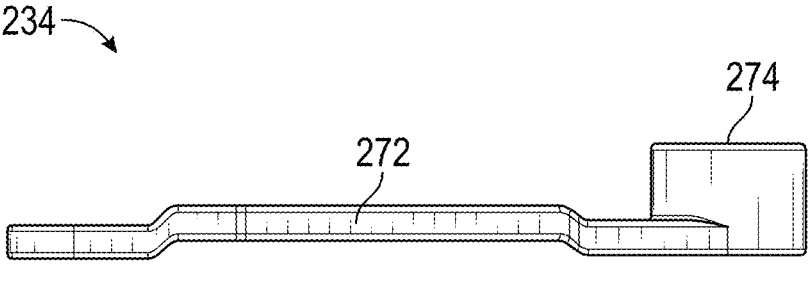

FIGS. 8A and 8B illustrate various views of a second lever 234, which can also be referred to as an arm, limb, member, etc. The second lever 234 can include a joint 274, which can be mounted on the mounts 252 of the base 216. The joint 274 can have a hole 276 therethrough to facilitate coupling to the base 216 and the cover 214 via the fasteners 230. The second lever 234 can include a raised portion 272, which can enable the second lever 234 and the first lever 232 to cross over each other without interference. The second lever 234 can extend from the joint 274 at an angle.

Figure 9A:
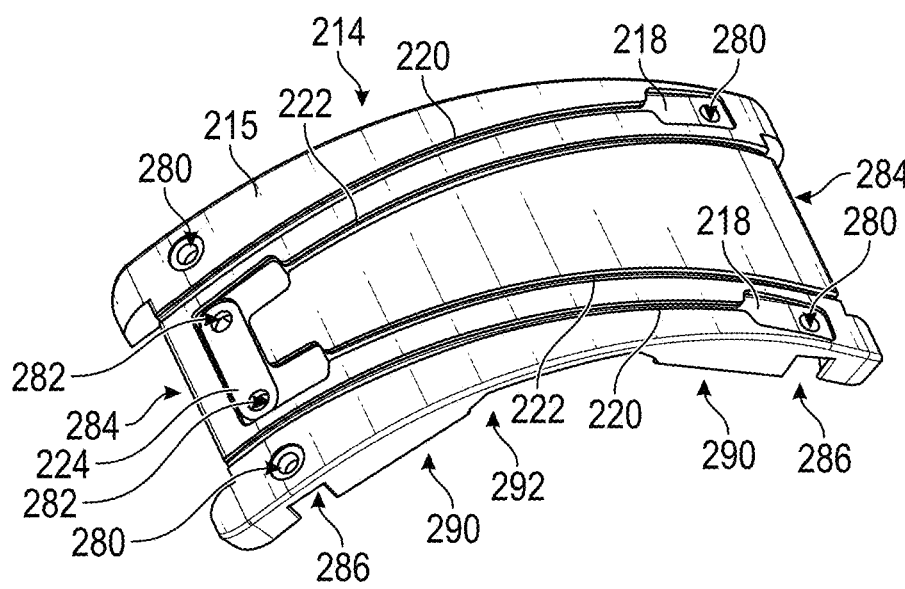
FIGS. 9A and 9B illustrate views of a cover of the compression actuator unit.
Figure 9B:
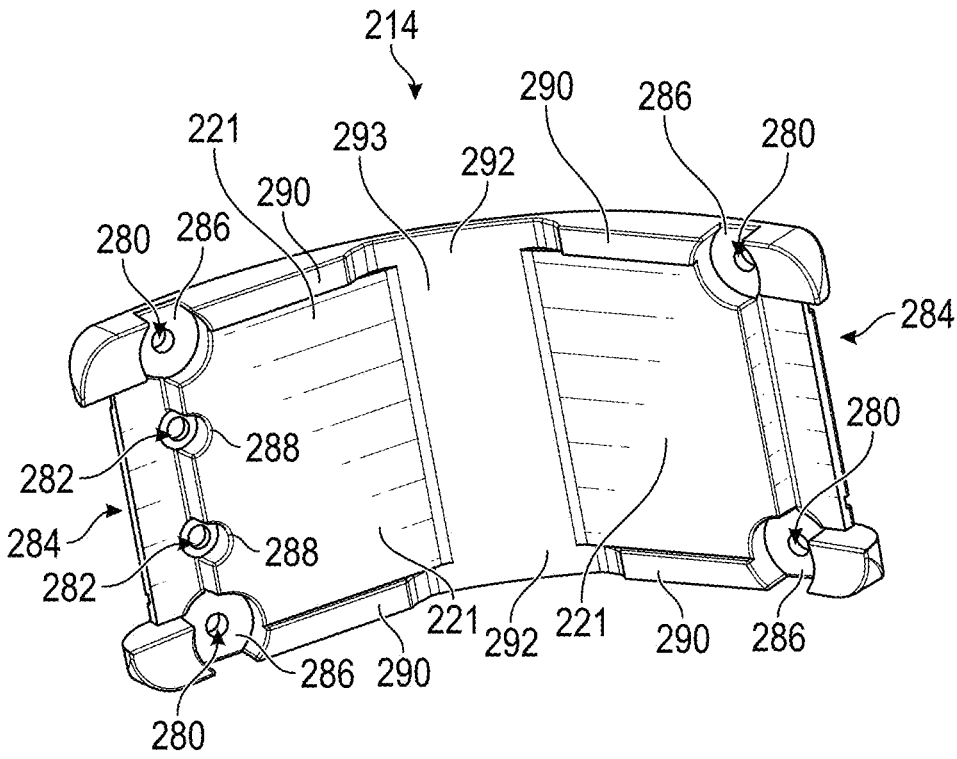

FIGS. 9A and 9B illustrate various views of the cover 214. As shown in FIG. 9A, the cover 214 can include a curved exterior surface 215 configured to be face outward from the skin of the user when the compression garment is worn by the user. The cover 214 can include recesses 218 and recesses 224 disposed in the exterior surface 215 that can house leads 226. The cover 214 can include first channels 222 and second channels 220 through which the wires or the like can be routed across the exterior surface 215. The cover 214 can include recesses 284, which can also be referred to as gaps or receiving regions, to receive the slides 236 therein. The recesses 284 can be disposed on opposing sides of the cover 214. The cover 214 can include a plurality of holes 280 to receive the fasteners 230 to facilitate coupling with the first lever 232, second lever 234, and base 216. The cover 214 can include a plurality of holes 282 to receive the fasteners 228 to facilitate coupling the leads 226 in the recess 224.

As shown in FIG. 9B, the cover 214 can have an interior surface 293. The interior surface 293 can have one or more inclined faces 221 that can be configured to provide clearance for the sled 209 to slide within the housing 212 between the cover 214 and the base 216. The cover 214 can include side walls 290 extending away from the interior surface 293. The side walls 290 can be disposed proximate lateral longitudinal sides of the cover 214. In some variants, the side walls 290 can contact the base 216 when the cover 214 and base 216 are coupled together. A gap 292 can be disposed in the side walls 290. The gap 292 can be sized to receive the tab 248 of the base 216 therein, as described herein. The cover 214 can include a plurality of cavities or recesses 286 that can receive the joints 274 of the first lever 232 and second lever 234 therein. The cover 214 can include holes 280 disposed in the cavities 286 to receive the fasteners 230 therein to facilitate coupling the cover 214, base 216, first lever 232, and second lever 234 together.

Figure 10A:
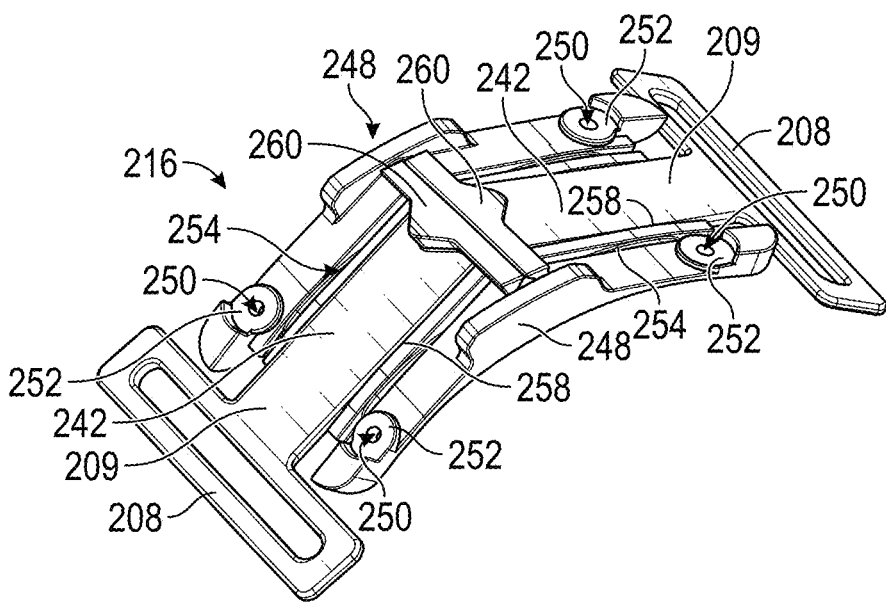
FIGS. 10A and 10B illustrate views of the sleds disposed in slots of the base.
Figure 10B:
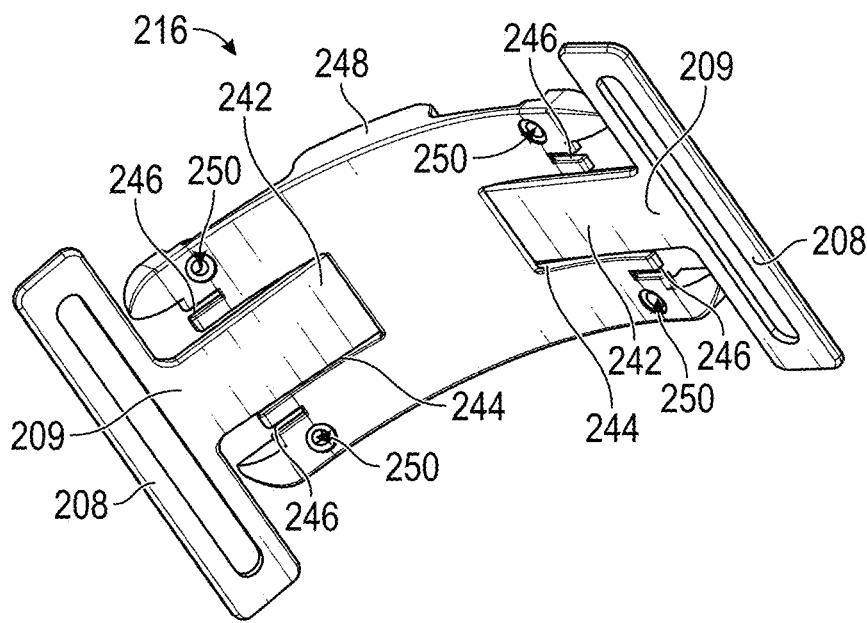

FIGS. 10A and 10B illustrate various views of the sleds 209 disposed in the slots 258 of the base 216. As illustrated, the tongues 242 are disposed in the slots 258 through the gaps 244 in the base 216. The sleds 209 can slide within slots 258 with the tongues 242 disposed therein. As illustrated, the sleds 209 are positioned such that the engagement portions 260 of the respective sleds 209 are contacting each other, which can correspond to a full stroke length of the compression actuator unit 206 to apply compression to an anatomical feature of the user. With the engagement portions 260 contacting each other, the D rings 208 can be at positions that can correspond with providing maximum tensioning force from the compression actuator unit 206.

Figure 10C:
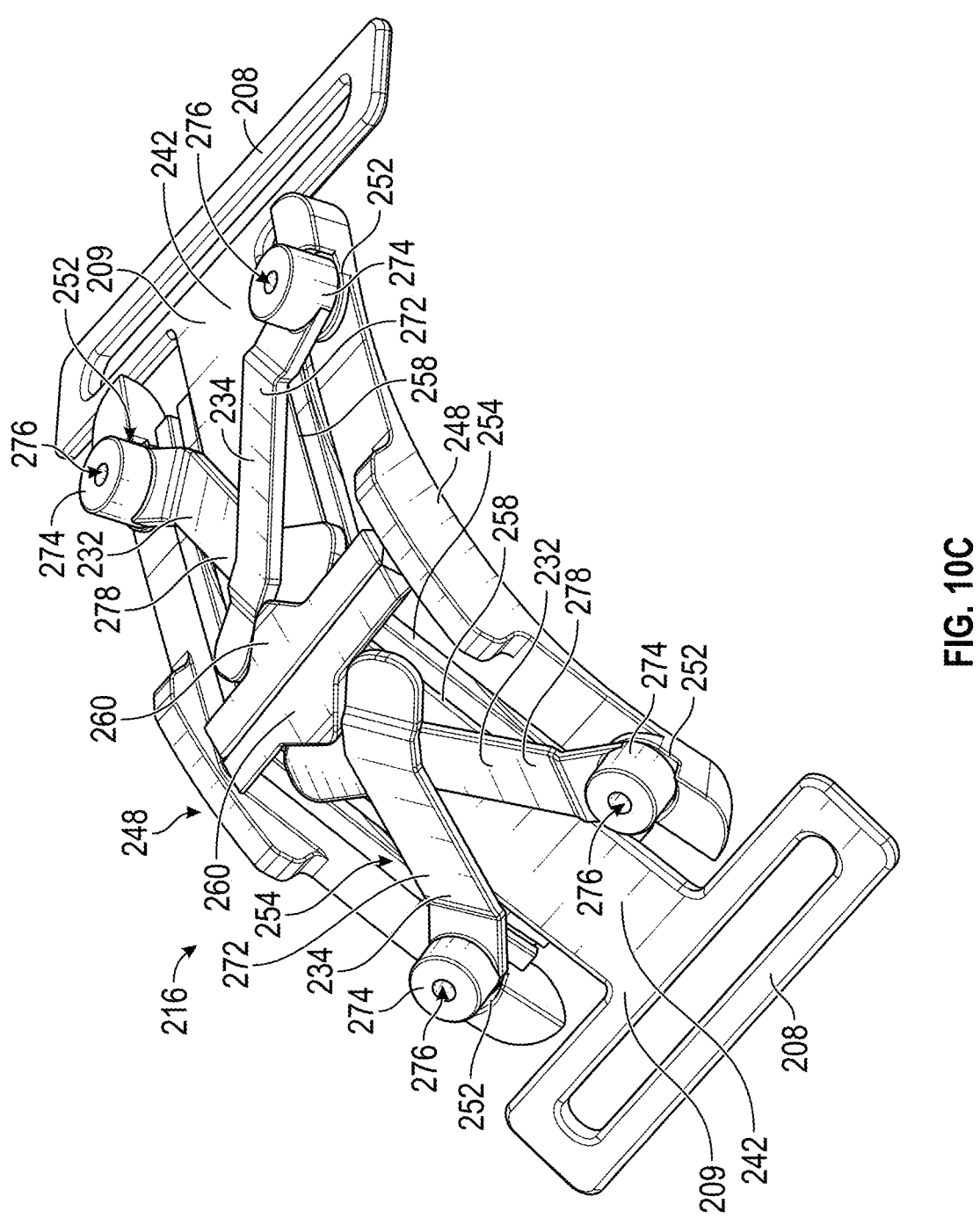
FIG. 10C illustrates the first and second levers mounted on the base.

FIG. 10C illustrates the first levers 232 and second levers 234 disposed on the base 216. The joints 274 of the first levers 232 and second levers 234 are positioned at the mounts 252 of the base 216. With the fasteners 230 coupling the first levers 232 and second levers 234 to the base 216 at the mounts 252, as described herein, the first levers 232 and second levers 234 can pivot about the fasteners 230 during actuation. The raised portions 272 of the second levers 234 can provide clearance for the lowered portion 278 of the first levers 232 as the second levers 234 rotate over the first levers 232. As shown, the first levers 232 and second levers 234 are rotated to positions to place the engagement portions 260 of each of the sleds 209 against each other, which can correspond to a full stroke length of the compression actuator unit 206. The first levers 232 and second levers 234, in some variants, can contact the engagement portions 260 during a full stroke length, i.e., throughout the entire rotation of the first levers 232 and second levers 234 to the illustrated position.

Figure 10D:
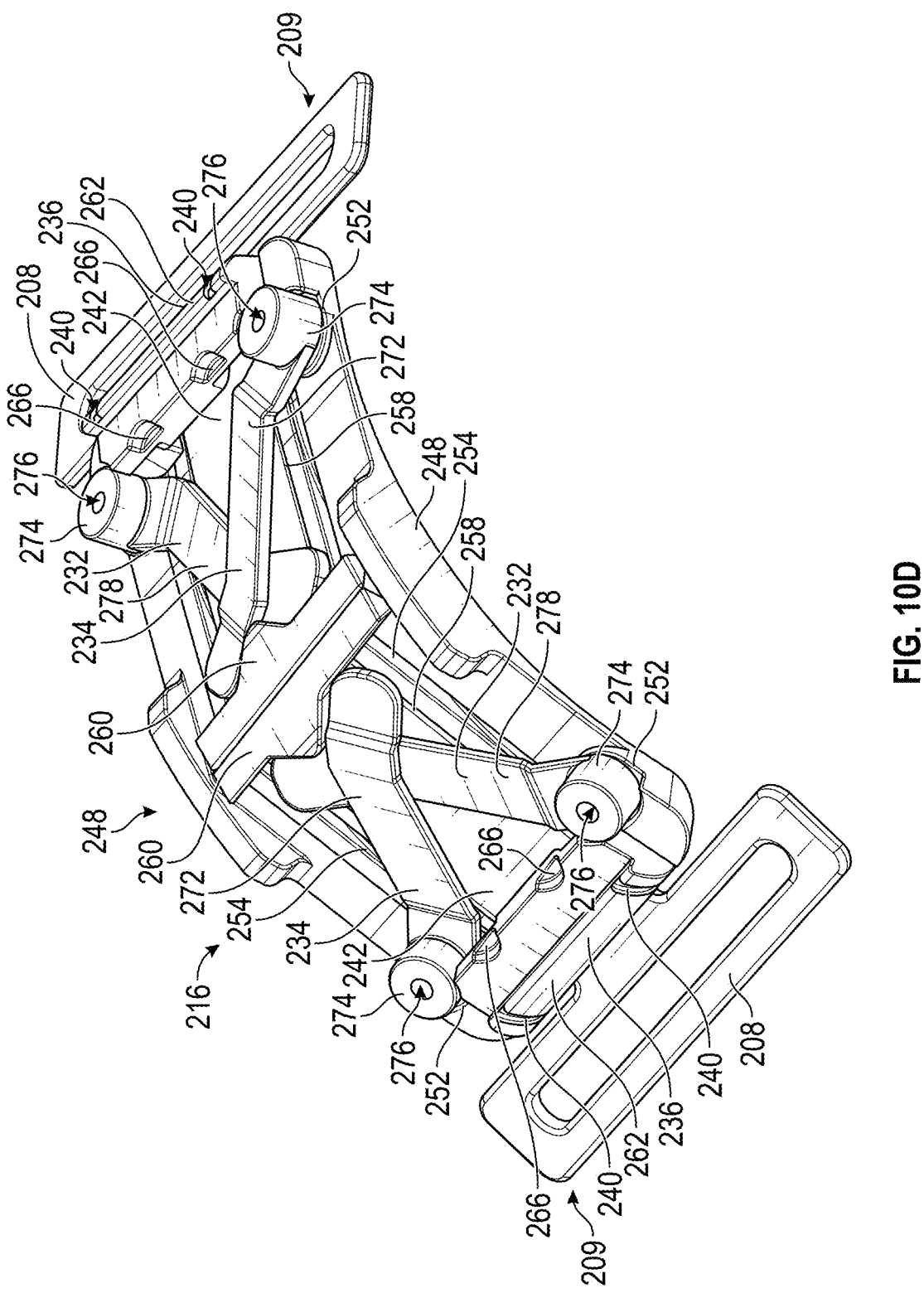
FIG. 10D illustrates the slides disposed at opposing ends of the base.

FIG. 10D illustrates the slides 236 disposed on the base 216. The slides 236 can be positioned on opposing sides of the base 216. As described herein, the contraction of the wires can translate the slides 236 towards each other, pushing the first levers 232 and second levers 234 to cause the rotation thereof. The rotating first levers 232 and second levers 234 can push against the engagement portions 260 of the sleds 209 to slide the sleds 209 within the slots 258 until the engagement portions 260 contact each other. As described herein, a controller can control the amount of electrical input applied to the wires to precisely control the contraction of the wires such that the sleds 209 can be placed along a continuum of positions, which can include predetermined positions. This can enable the compression actuator units 206 to precisely control the pulling force applied by the compression actuator units 206 on the straps and/or other features of the compression garments, which in turn controls the pressure applied to the anatomical feature of the user.

Figure 10E:
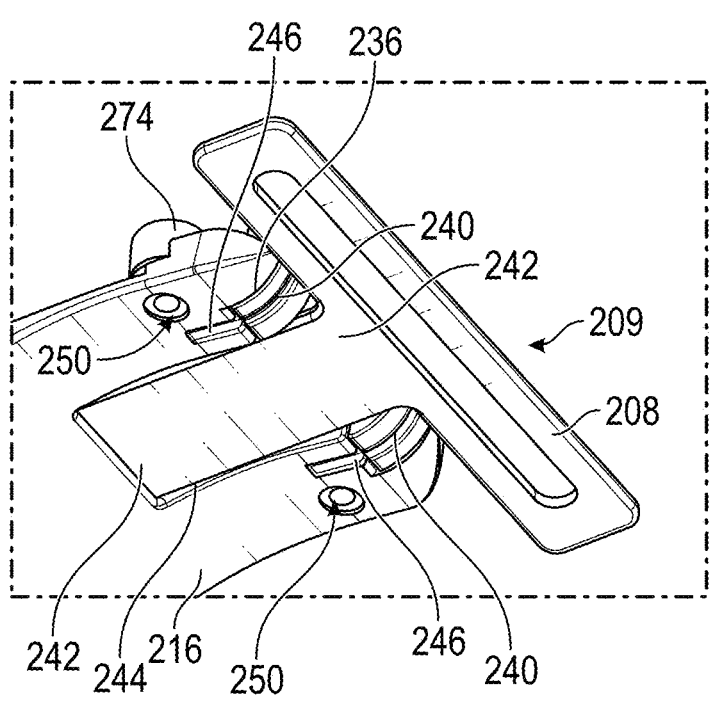
FIGS. 10E, 10F, and 10G illustrate various views of an end of the compression actuator unit 206 with the cover removed.
Figure 10F:
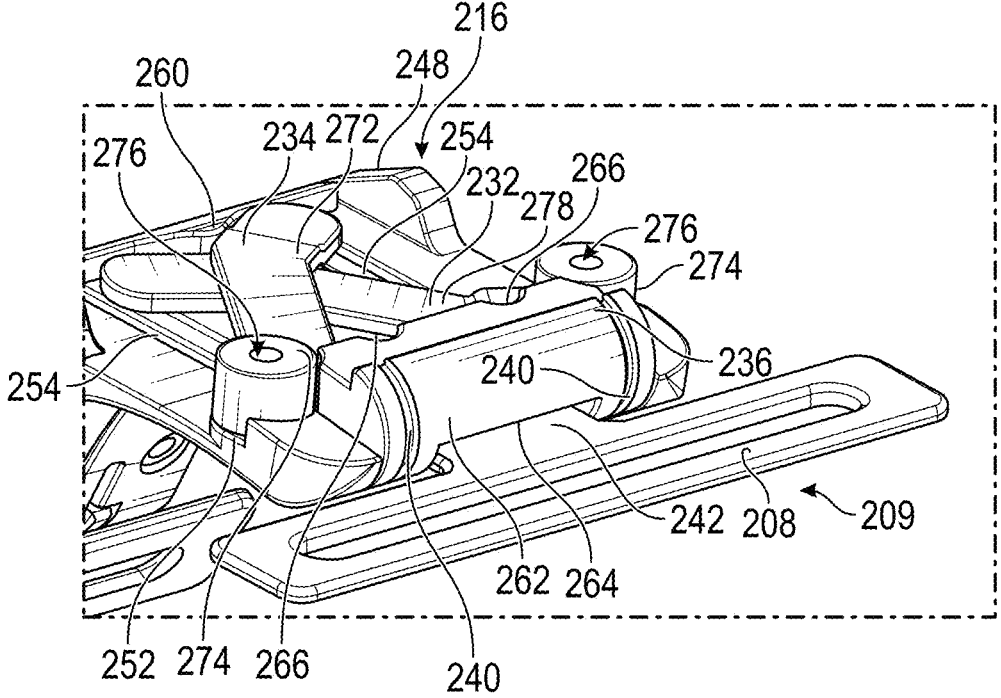
Figure 10G:
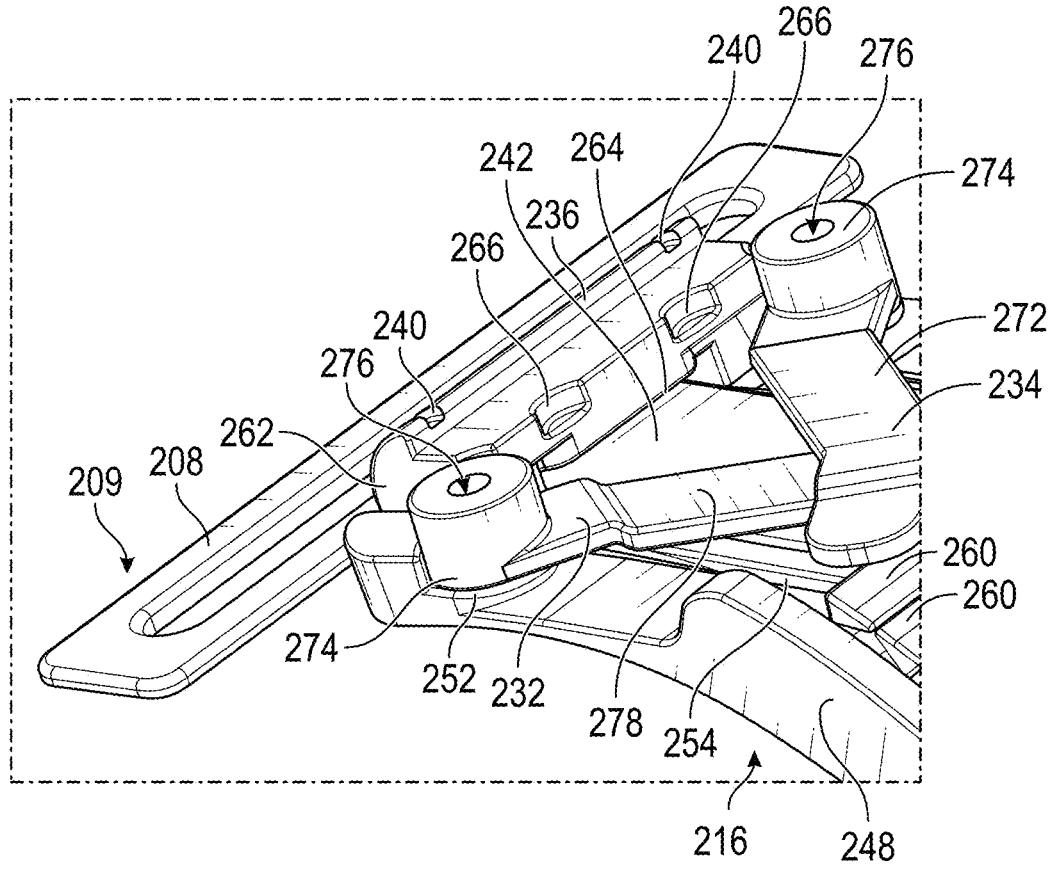
Figure 10H:
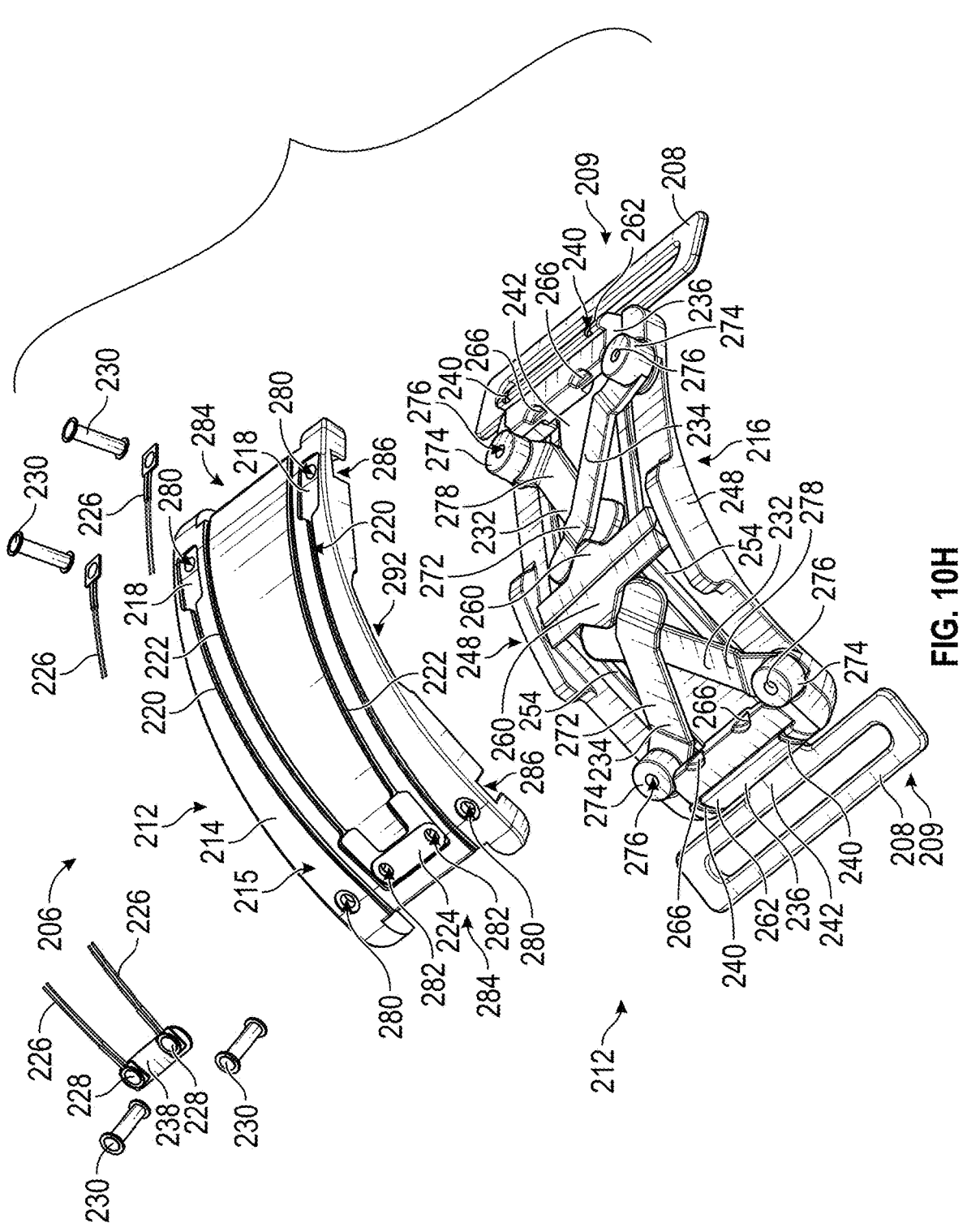
FIG. 10H illustrates the compression actuator unit with the cover removed.

FIGS. 10E, 10F, and 10G illustrate various views of one side of the compression actuator unit 206 with the cover 214 removed. As shown, the tongue 242 of the compression actuator unit 206 extends through the slot 264 of the slide 236, through the gap 244 in the base 216, and into the slot 258 of the base 216. As described herein, the rotation of the first lever 232 and the second lever 234 can push against the engagement portion 260 of the sled 209 to translate the sled 209 within the slot 258 of the base 216 to apply a pull force on the strap and/or other feature of the compression garment to apply compression to an anatomical feature of the user. FIG. 10H illustrates a view of the compression actuator unit 206 with the cover 214 removed. As described herein, the cover 214 can be coupled to the base 216 via the fasteners 230 to enclose the first levers 232, second levers 234, and other features of the compression actuator unit 206 within the housing 212.

Figure 11A:
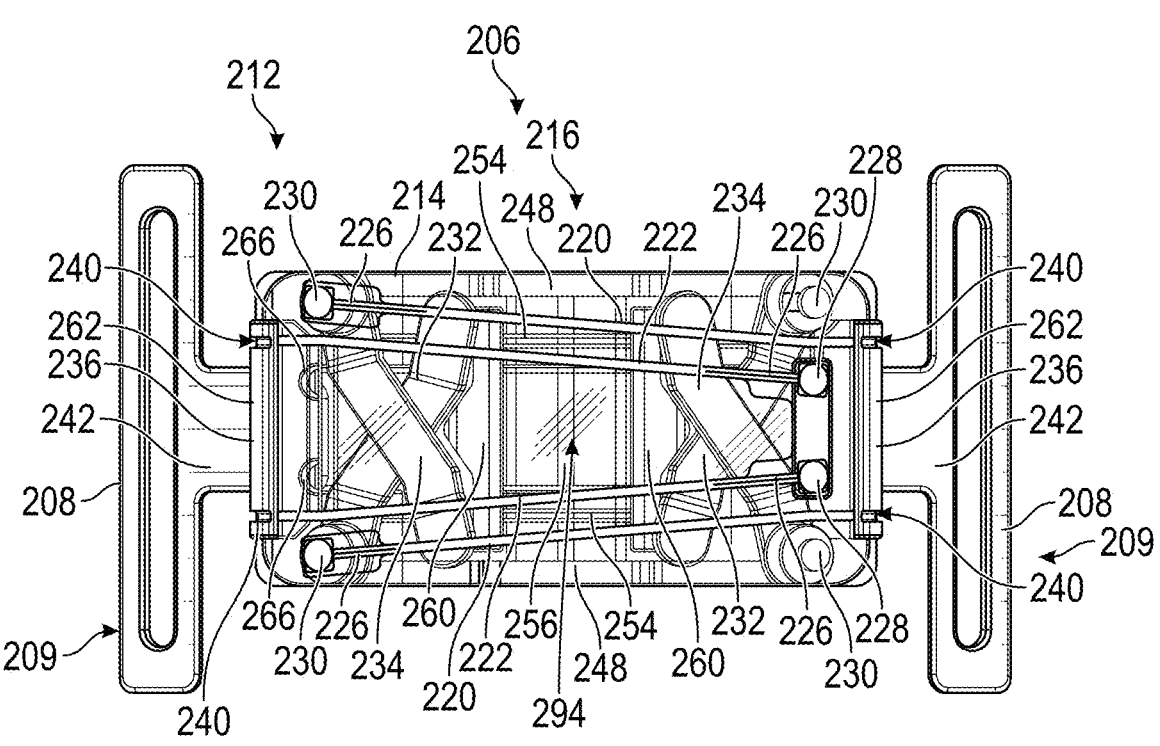
FIG. 11A illustrates the compression actuator unit in an intermediate actuation configuration with the levers partially extended.

FIG. 11A illustrates the compression actuator unit 206 in one of many intermediate actuation configurations between an unactuated configuration, wherein the compression actuator unit 206 is not applying an additional pull force on the straps and/or other feature of the compression garment, and an actuated configuration corresponding to a full stroke length of the compression actuator unit 206. As shown the engagement portions 260 are not touching yet the first levers 232 and second levers 234 are rotated away from the unactuated configuration, positioning the D rings 208 at an intermediate position relative to the housing 212 and the engagement portions 260 at intermediate positions within the slots 258 of the base 216. The first levers 232 and second levers 234 are partially expanded or rotated. The compression actuator unit 206 is also illustrated with a pressure sensor 294. The pressure sensor 294 can measure a characteristic indicative of the pressure applied by the compression actuator unit 206.

Figure 11B:
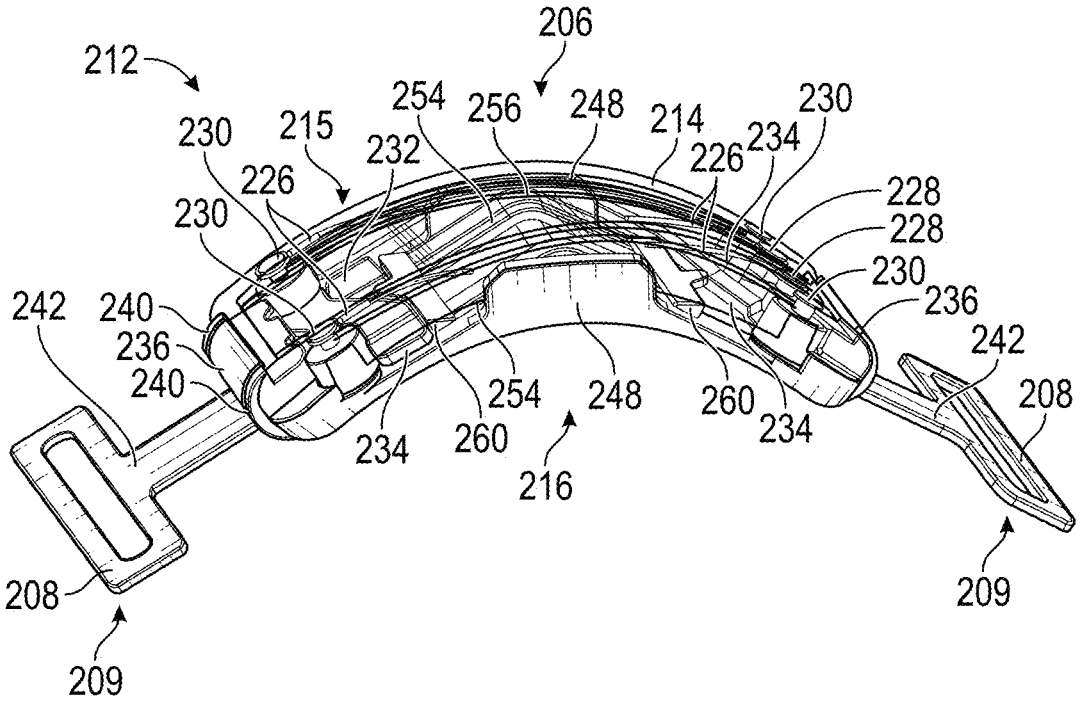
FIGS. 11B and 11C illustrate the compression actuator unit in an unactuated configuration with the levers collapsed.
Figure 11C:
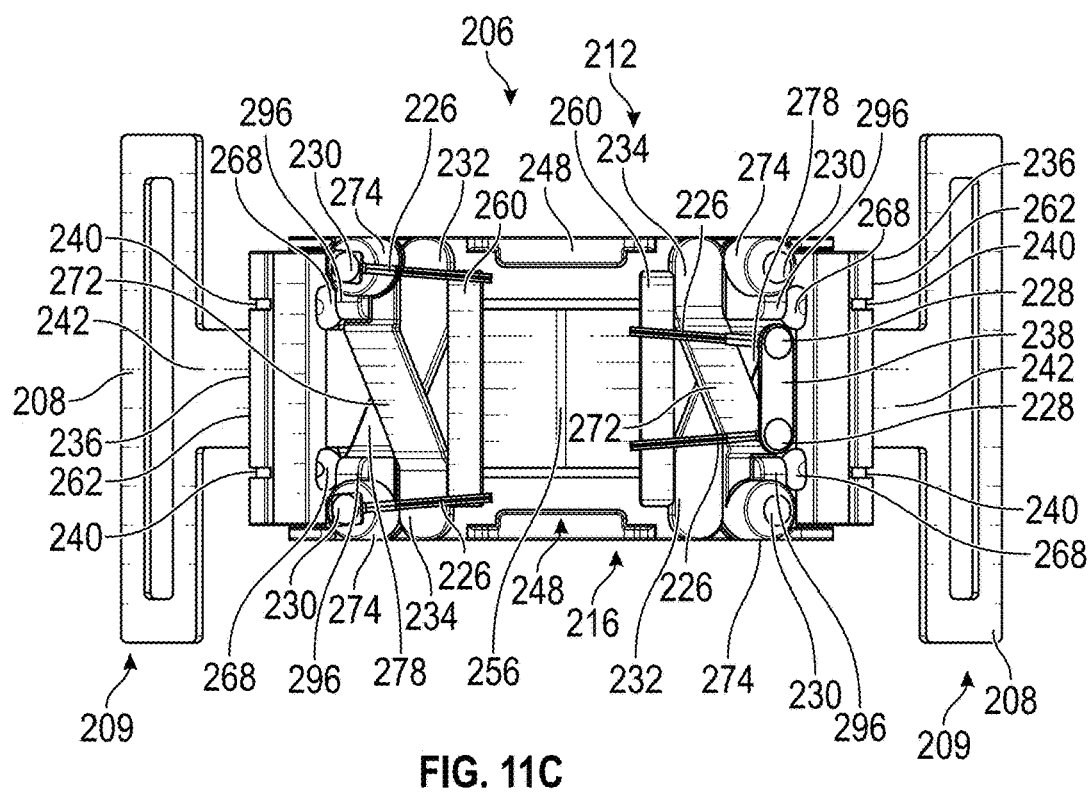

FIGS. 11B and 11C illustrate the compression actuator unit 206 in an unactuated configuration, which may not apply an additional pull force on the straps and/or other feature of the compression garment. As shown, the first levers 232 and second levers 234 are not rotated out into an expanded configuration, but instead, the first levers 232 and second levers 234 are collapsed. As illustrated, the D rings 208 are spaced away from the housing 212 and the engagement portions 260 are spaced away from each other. The protrusions 268 are not pushing the first levers 232 and second levers 234 to cause the rotation thereof. As shown in FIG. 11C, the first levers 232 and second levers 234 can include protrusions 296, which can also be referred to as tabs or flanges, against which the protrusions 268 of the slides 236 can push during actuation.

Figure 11D:
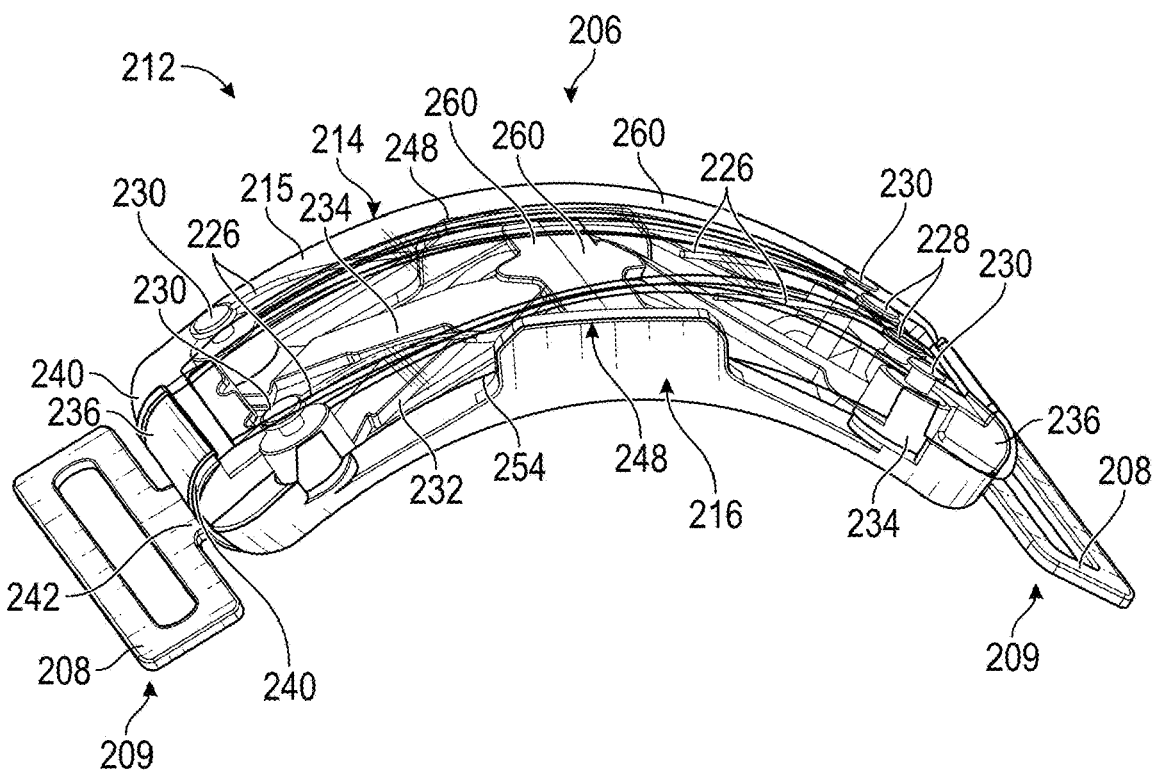
FIGS. 11D and 11E illustrate the compression actuator unit in an actuated configuration corresponding to a full stroke length of the unit with the levers fully expanded.
Figure 11E:
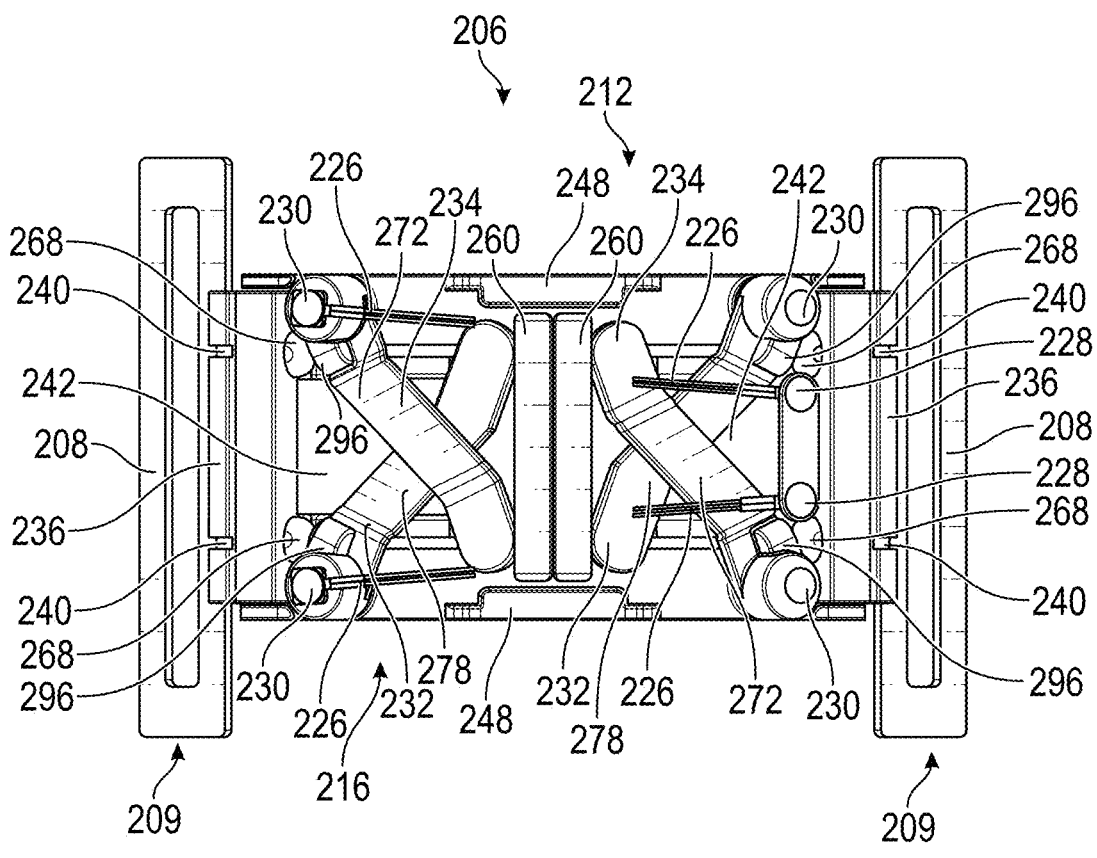

FIGS. 11D and 11E illustrate the compression actuator unit 206 in an actuated configuration corresponding to a full stroke length of the compression actuator unit 206. As shown, the slides 236, via the contraction of the wire(s), have been pulled inward to push the against the first levers 232 and second levers 234 to cause the rotation thereof to an expanded configuration until the sleds 209 have been translated within the slots 258 of the base 216 such that the engagement portions 260 are contacting each other. In some variants, the protrusions 268 of the slides 236 can push against the protrusions 296 of the first levers 232 and second levers 234 to rotate the first levers 232 and second levers 234. As illustrated, the D rings 208 are positioned proximate the housing 212 applying, in some variants, a maximum pulling force on the straps and/or other features of the compression garment to apply compression to the user. In some variants, only one side of the compression actuator unit 206 includes a sled 209 to apply a pulling force.

Figure 12A:
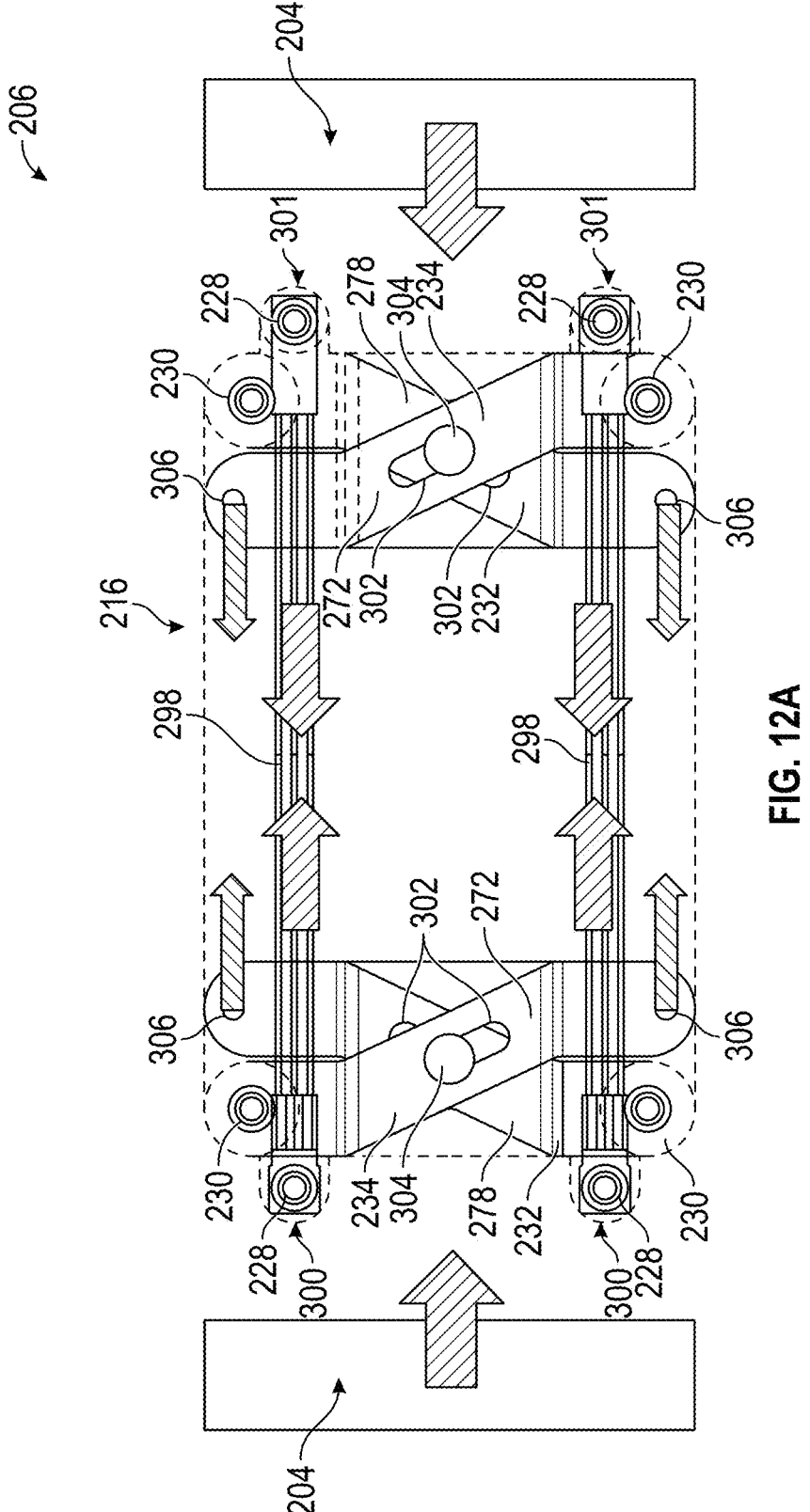
FIGS. 12A and 12B illustrate a variation of the actuation mechanism of the compression actuator unit.
Figure 12B:
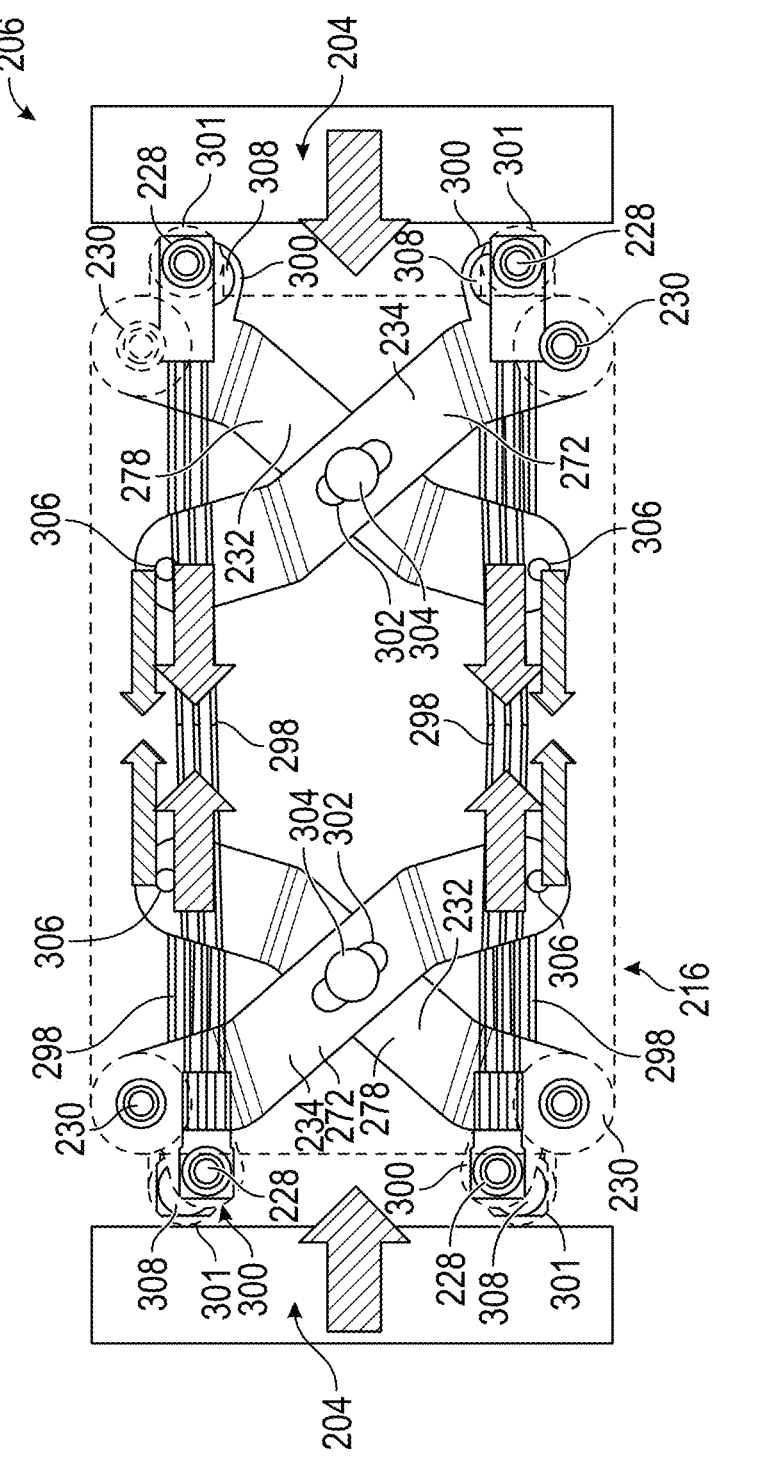

FIGS. 12A and 12B illustrate a variation of the actuation mechanism of the compression actuator unit 206. FIG. 12A illustrates the actuation mechanism in a collapsed unactuated configuration, and FIG. 12B illustrates the actuation mechanism in an expanded actuated configuration. As shown, the first levers 232 and second levers 234 can include slots 302 therein. A fastener 304, which can slide within the slots 302, can be inserted through the slots 302 to couple the first levers 232 and second levers 234 in pairs disposed on opposing sides of the base 216. The fastener 304 can help facilitate equal rotation of the first levers 232 and second levers 234 via coupling.

As shown in FIG. 12B, the first levers 232 and second levers 234 can include tabs 300 disposed thereon. One or more wires 298 (e.g., three) can extend from the tabs 300 to a fixed tab 301 disposed on the base 216. As the wires contract in the direction of arrow C using any of the methods described herein, the first levers 232 and second levers 234 can be pulled at the tabs 300, rotating the first levers 232 and second levers 234 about the fasteners 230 to an expanded configuration such that the ends of the first levers 232 and second levers 234 move in the direction of arrow B. The movement of the ends of the first levers 232 and second levers 234 can amplify the contraction of the wires such that the straps 204 and/or other feature of the compression garment is pulled in the direction of arrow A to provide an increased range of compression.

Figure 13:
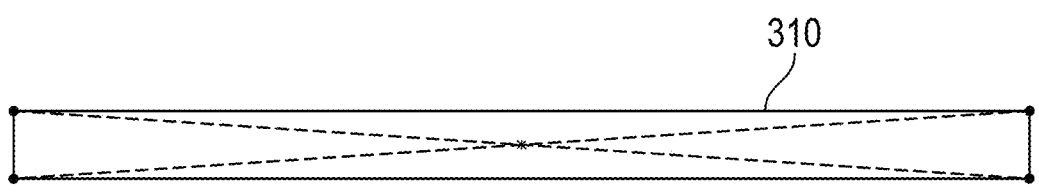
FIG. 13 illustrates a strip of material.

FIGS. 13-16K illustrates steps of assembly and various components of a compression actuator unit 206 which can include any of the features of other compression actuator units 206 described herein. FIG. 13 illustrates a strip 310 of material with example dimensions thereon. The strip 310 can be cut from a sheet of material, which can include polycarbonate.

Figure 14A:
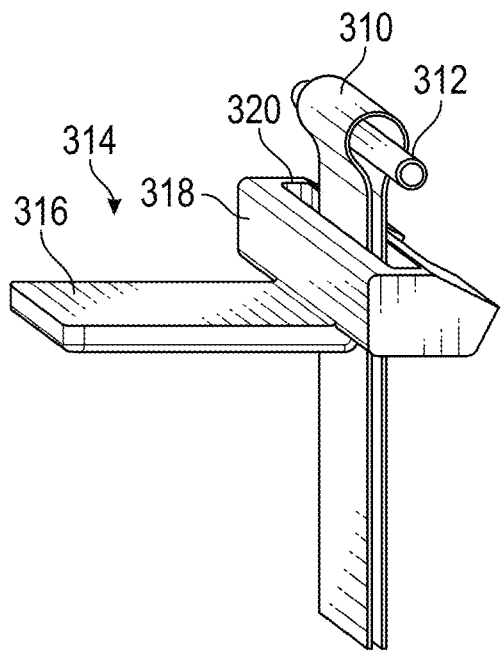
FIG. 14A illustrates the strip folded over to form a loop that is disposed through an opening of the sled with a pin in the loop.
Figure 14B:
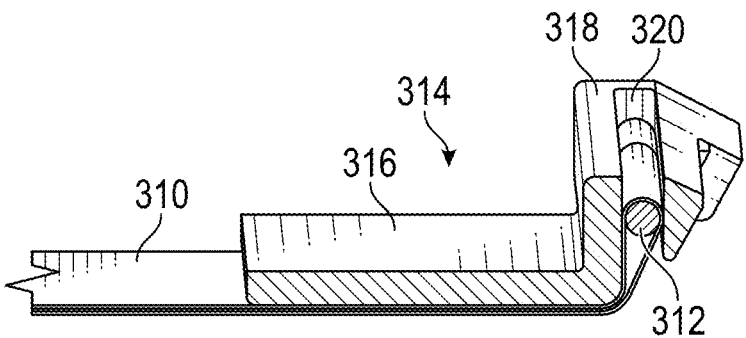
FIG. 14B illustrates the pin and loop secured within the opening of the sled.

As illustrated in FIG. 14A, the strip 310 can be folded in half to form a loop without forming a crease therein. The loop can be inserted through an opening or cavity 320 of a sled 314 and a rod or pin 312 inserted through the loop, which can help to secure the strip 310 to the sled 314. The sled 314 can include a tongue 316, which can be slid within a slot of a base 216 of the compression actuator unit 206 during actuation. The sled 314 can include a head or engagement portion 318 wherein the opening 320 is disposed. As illustrated in FIG. 14B, the strip 310 can be pulled and the rod or pin 312 pushed down, which can include using non-marrying tools, to seat the rod 312 in the cavity 320. The strip 310 can be pulled to remove slack therein as needed.

Figure 15A:
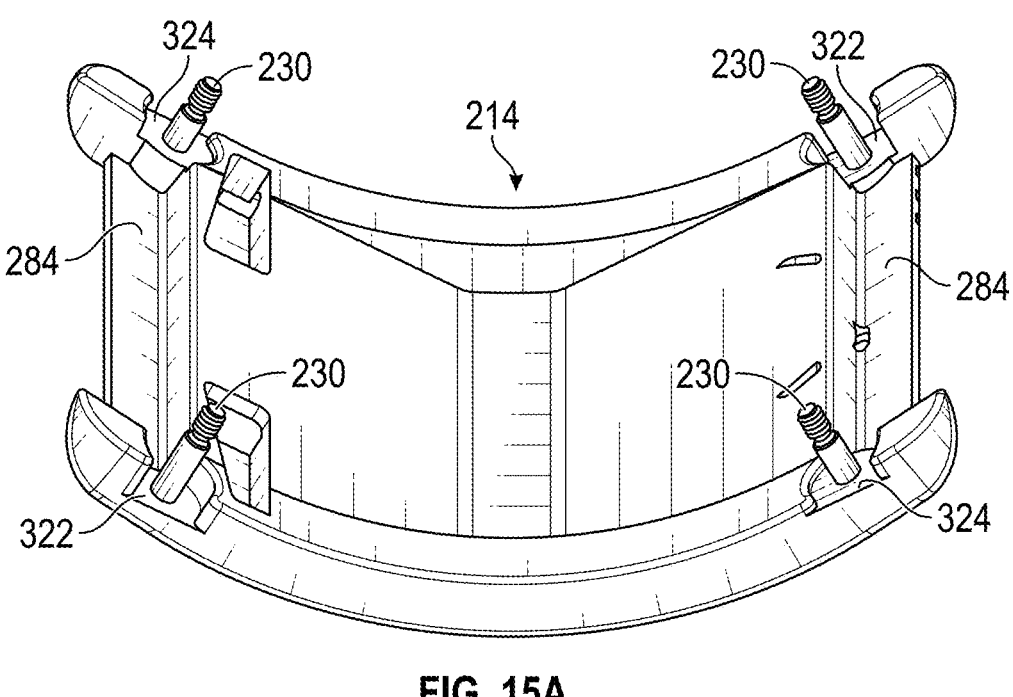
FIG. 15A illustrates fasteners disposed through the cover.
Figure 15B:
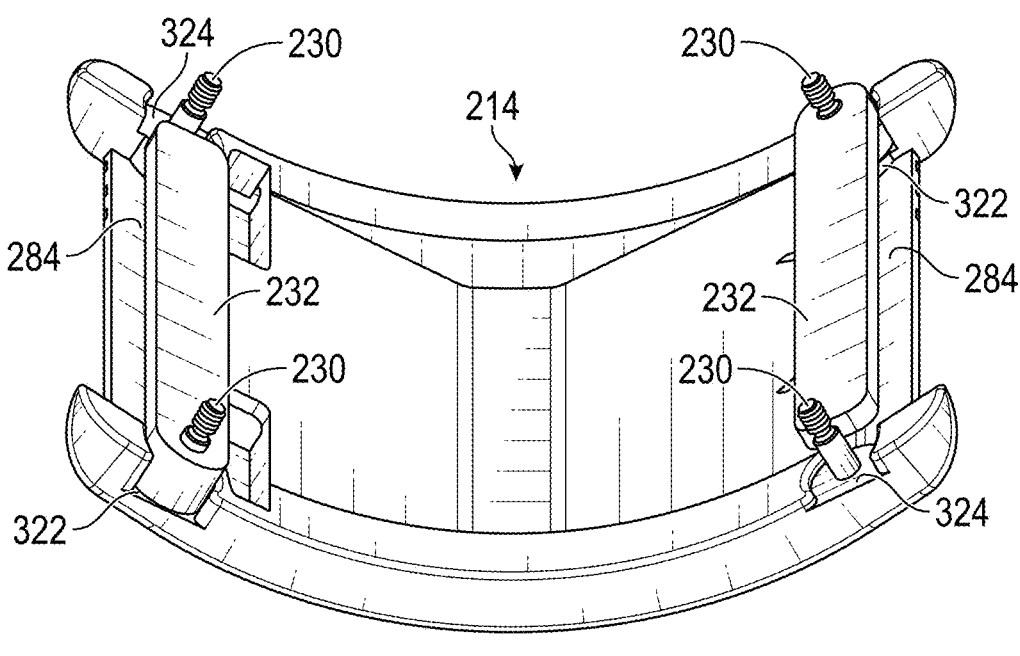
FIG. 15B illustrates levers coupled to fasteners positioned in the deep pockets of the cover.
Figure 15C:
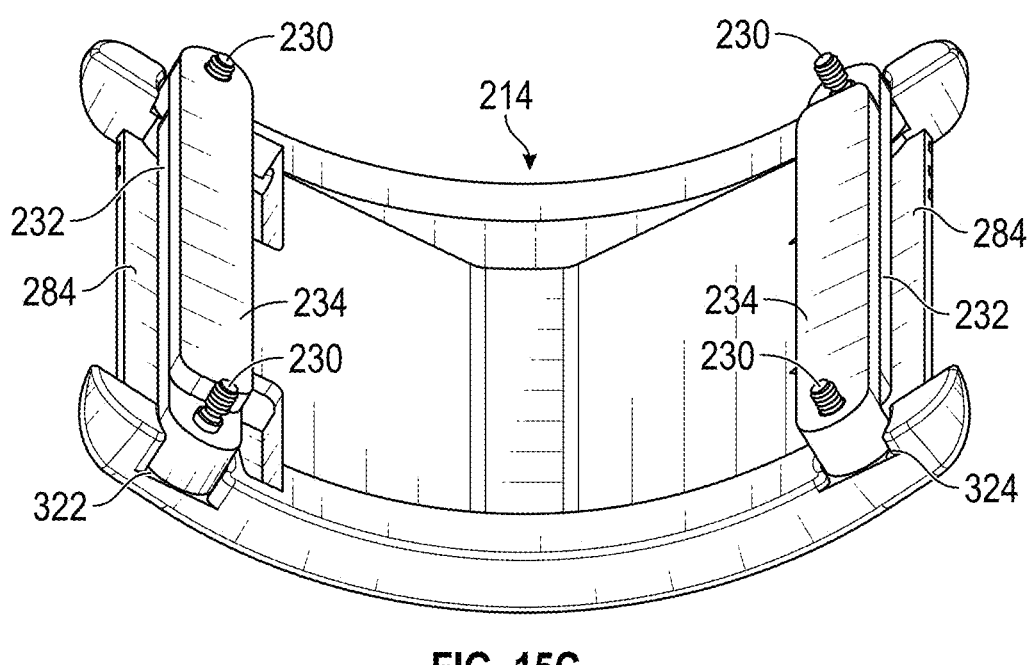
FIG. 15C illustrates levers coupled to fasteners positioned in the shallow pockets of the cover.

As illustrated in FIG. 15A, fasteners 230 (e.g., shoulder screws) can be inserted through holes in the pockets 322, 324. With the fasteners 230 in place, the first levers 232 can be disposed on the fasteners 230 positioned at the deep pockets 322, as illustrated in FIG. 15B. The second levers 234 can then be disposed on the fasteners 230 positioned at the shallow pocket 324 such that the second levers 234 are positioned over the first levers 232 as shown in FIG. 15C. The deep pockets 322 and shallow pockets 324 can enable the first levers 232 and second levers 234 to be the same while allowing the second levers 234 to rotate over the first levers 232 without interference, which can decrease manufacturing cost and complexity.

Figure 16A:
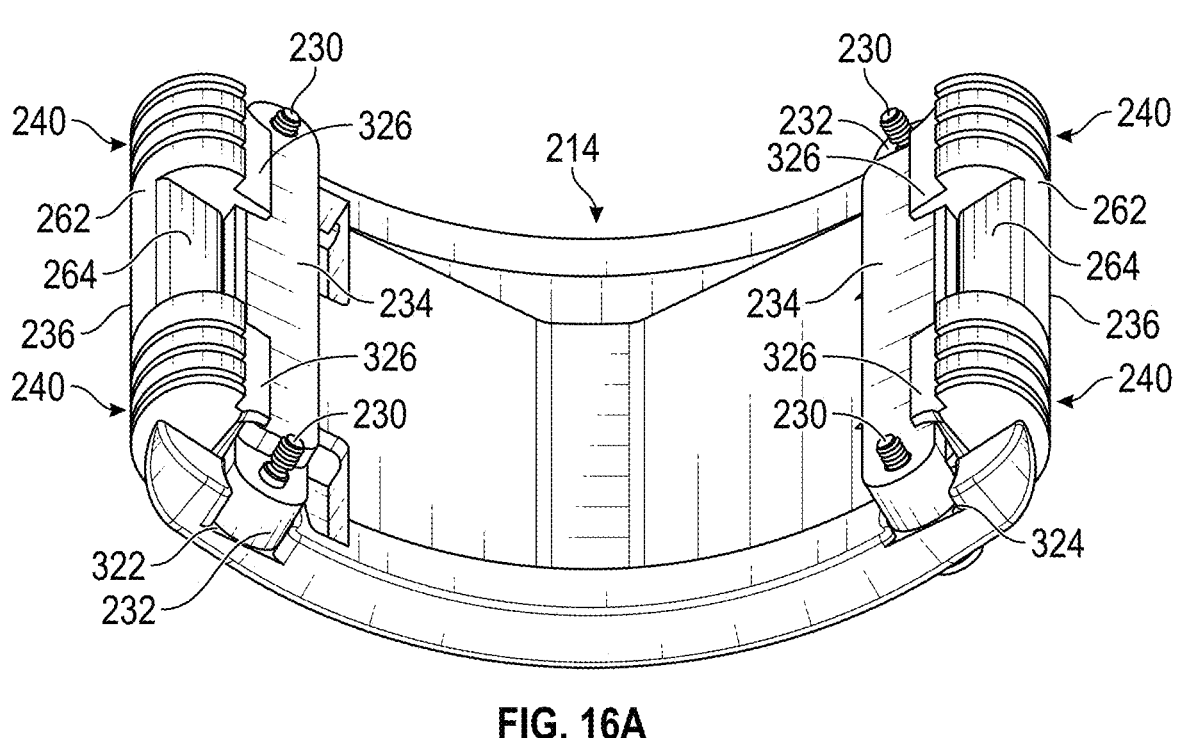
FIG. 16A illustrates slides disposed on opposing ends of the cover.
Figure 16B:
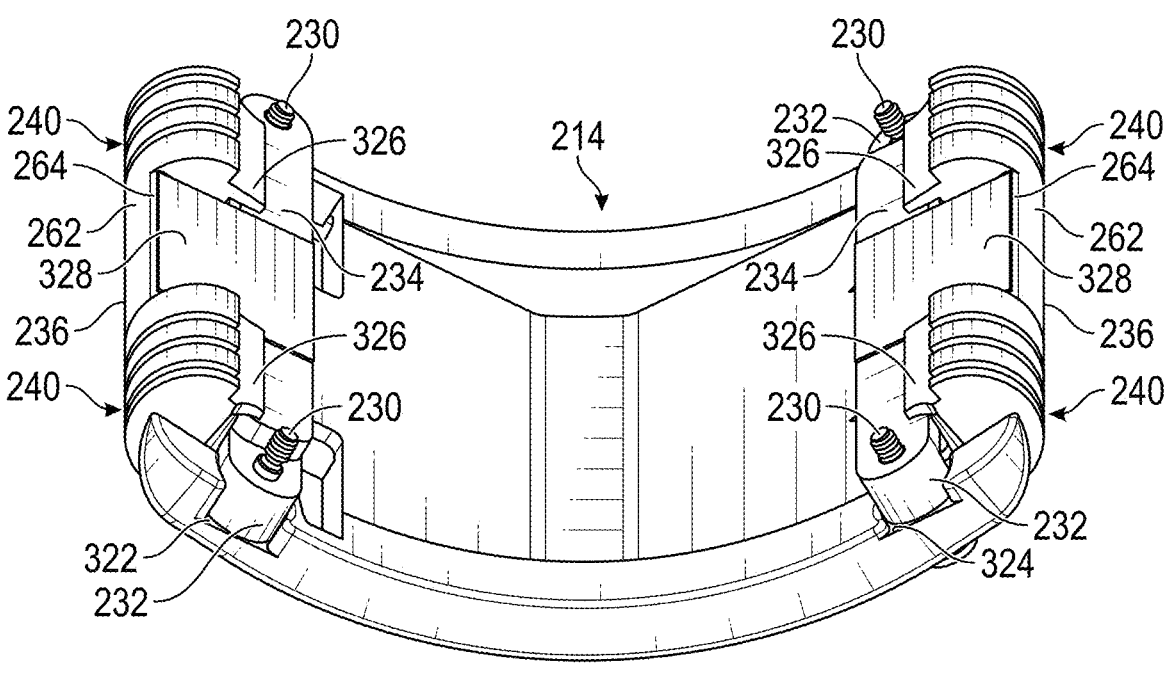
FIG. 16B illustrates the slides and levers temporarily taped in place.

As shown in FIG. 16A, the slides 236 can be positioned in the recesses 284 disposed on opposing sides of the cover 214. The slides 236 can include tabs 326 that can be disposed over the second levers 234. The tabs 326 can be disposed on opposite sides of the slot 264 of the slide 236 as shown. With the slides 236 in place, a piece of tape 328 or fixture can temporarily adhere the slides 236 to the second levers 234, securing the assembled components together during assembly as shown in FIG. 16B.

Figure 16C:
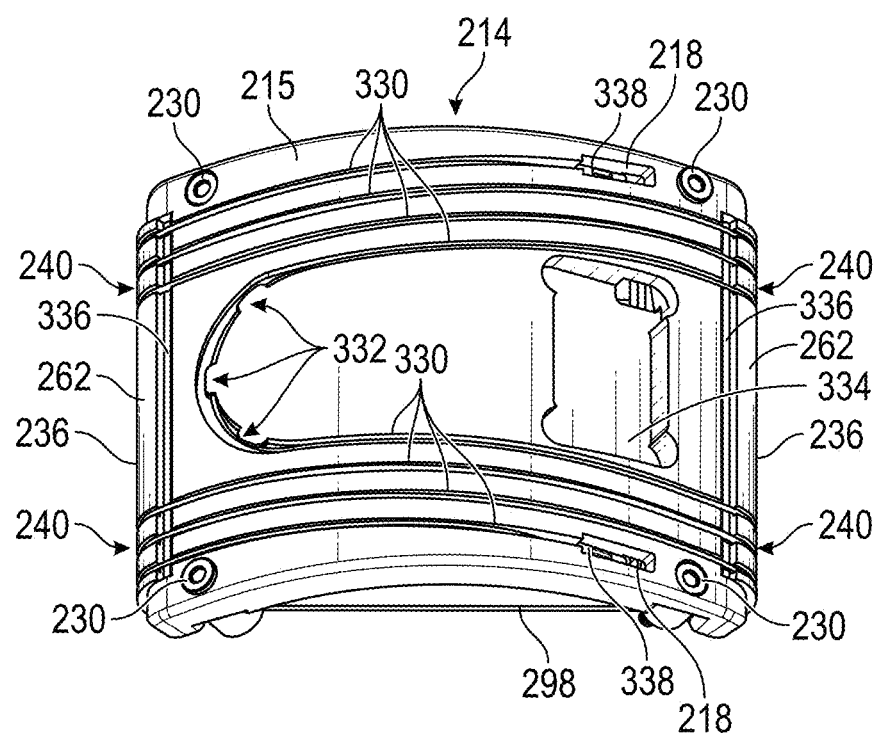
FIG. 16C illustrates a view of the cover with a wire routed through channels therein.
Figure 16D:
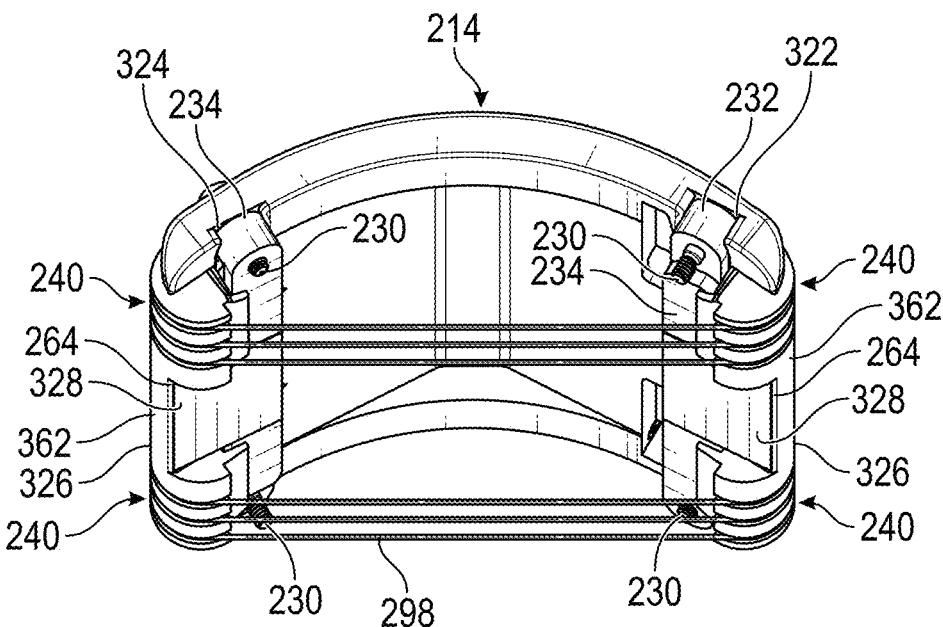
FIG. 16D illustrates another view of the cover with the wire routed through the channels therein.

As illustrated in FIG. 16C, the ends (e.g., barrels) 338 of a wire 298, which can be made of a smart memory material such as Nitinol, can be placed in the recesses or pockets 218 disposed in the exterior surface 215 of the cover 214. The wire 298 can be routed through the channels 330 disposed in the exterior surface 215 of the cover 214 and through the channels 240 of the slides 236. The channels 330 can include one or more retention features 332, such as tabs, to help retain the wire 298 in the channels 330. As the wire 298 is routed, the wire 298 can be temporarily secured in the channels 330 with tape and/or a fixture. As shown in FIG. 16D, there may be slack in the wire 298 after routing is complete. The tape 328 can be removed with the wire 298 in place.

Figure 16E:
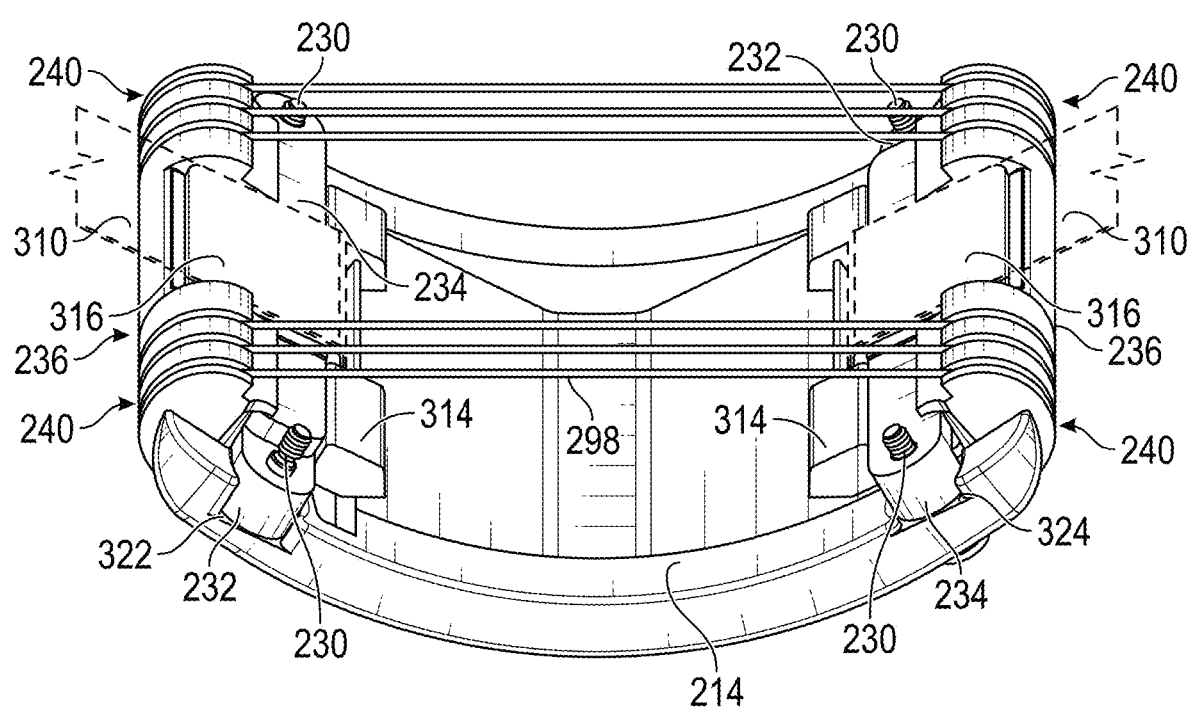
FIG. 16E illustrates a view of the cover with the sleds installed.
Figure 16F:
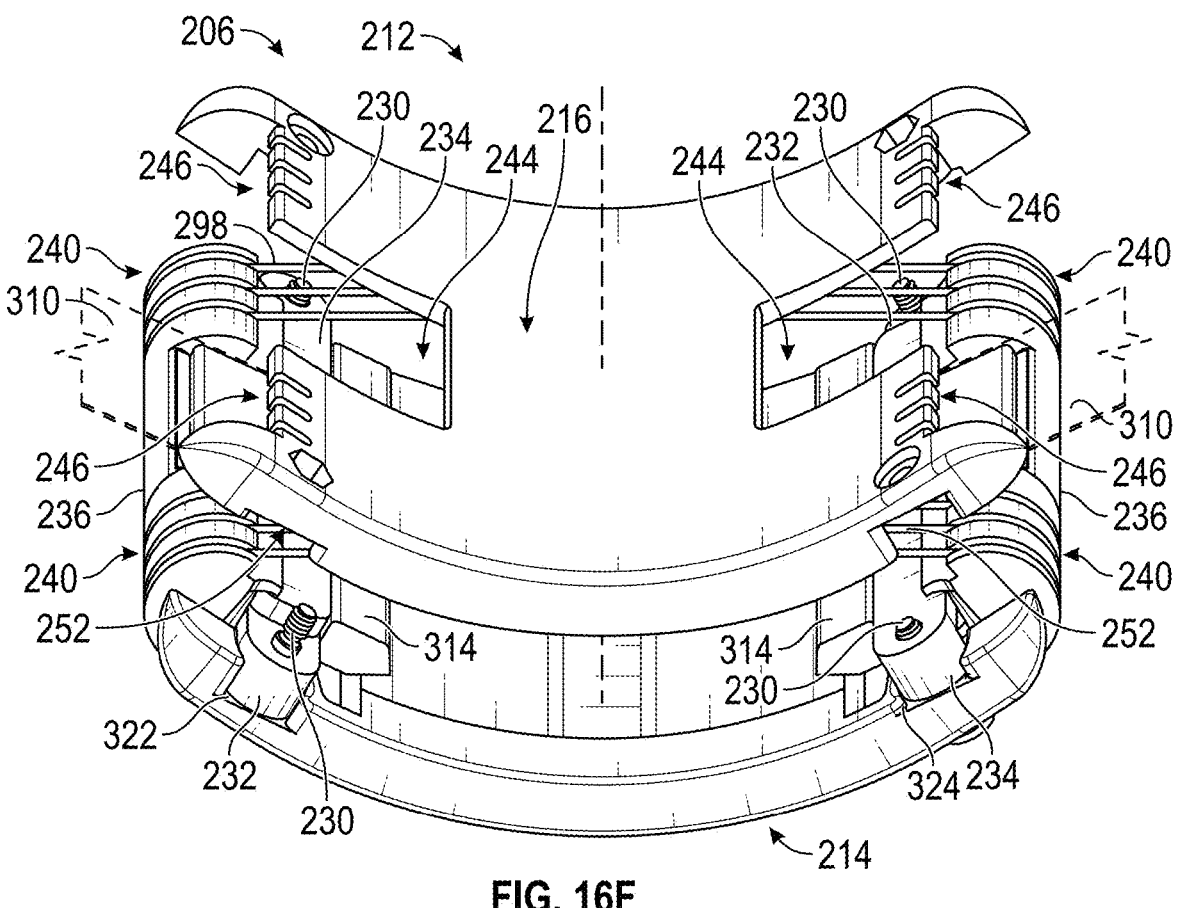
FIGS. 16F and 16G illustrate views of the base aligned with the cover for coupling.
Figure 16G:
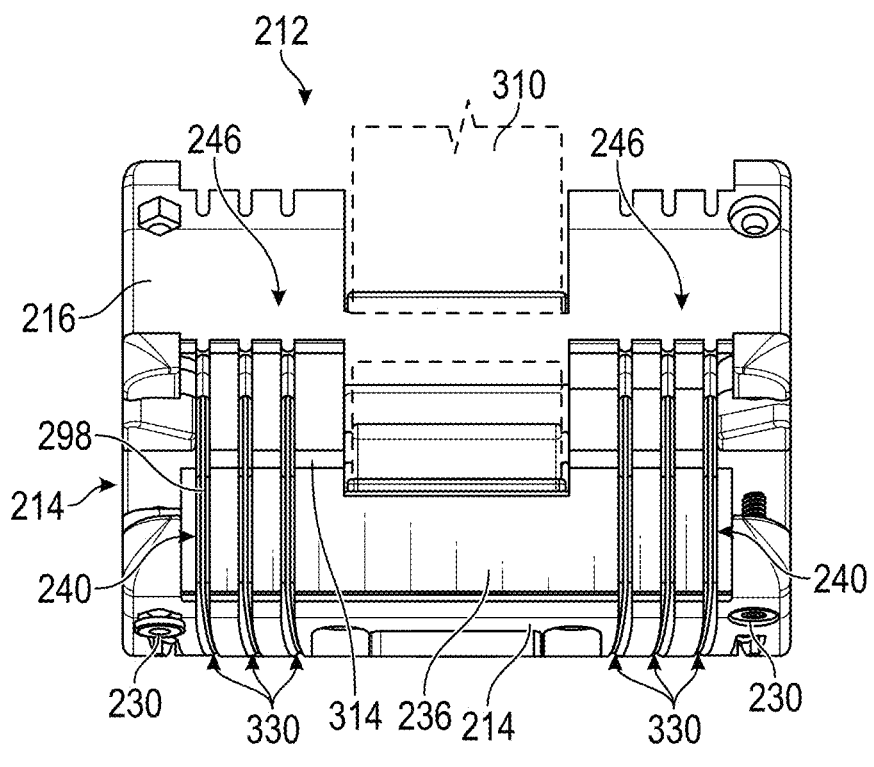
Figure 16H:
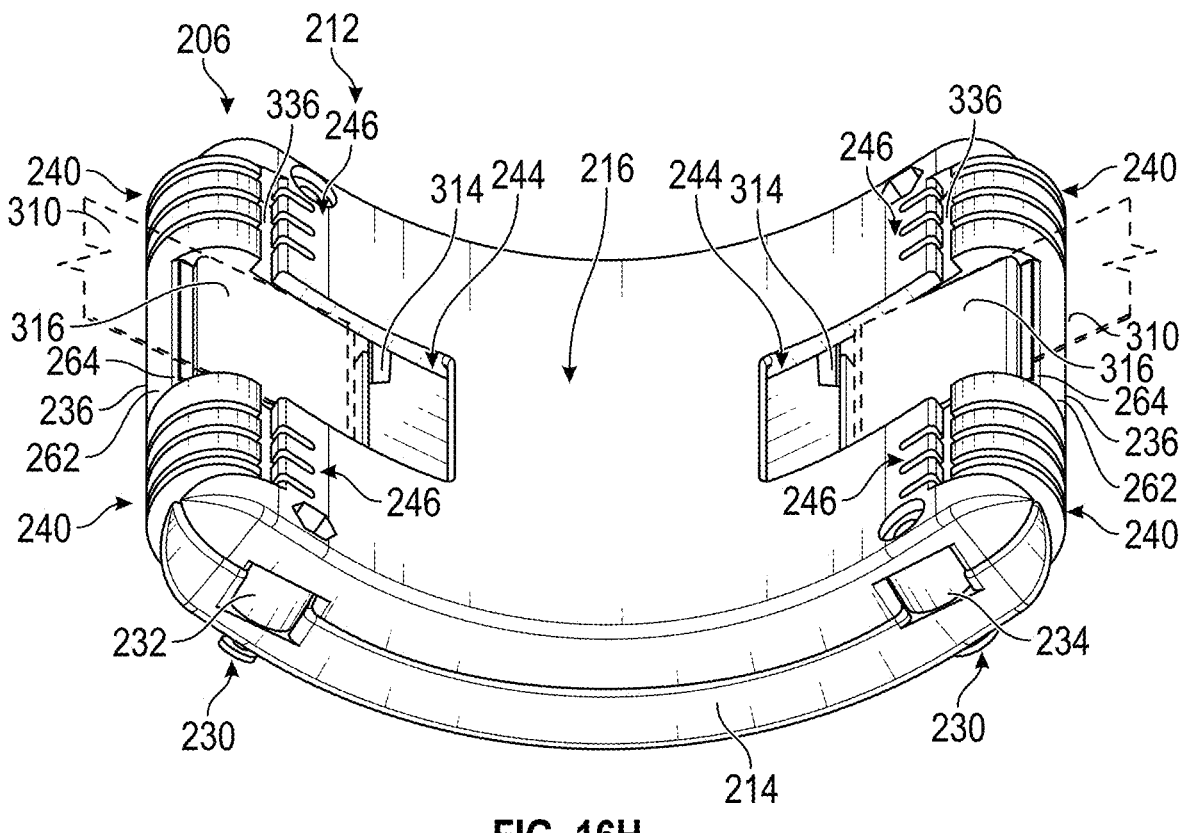
FIG. 16H illustrates the base positioned on the cover.
Figure 16J:
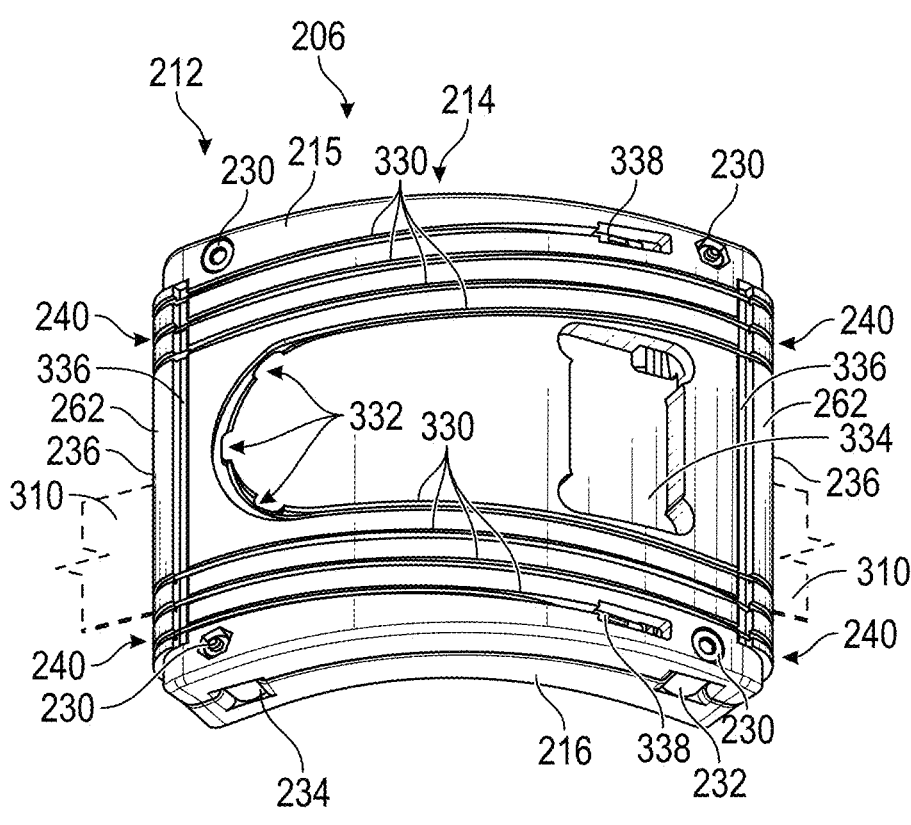
FIGS. 16J and 16K illustrate various views of the assembled compression actuator unit.
Figure 16K:
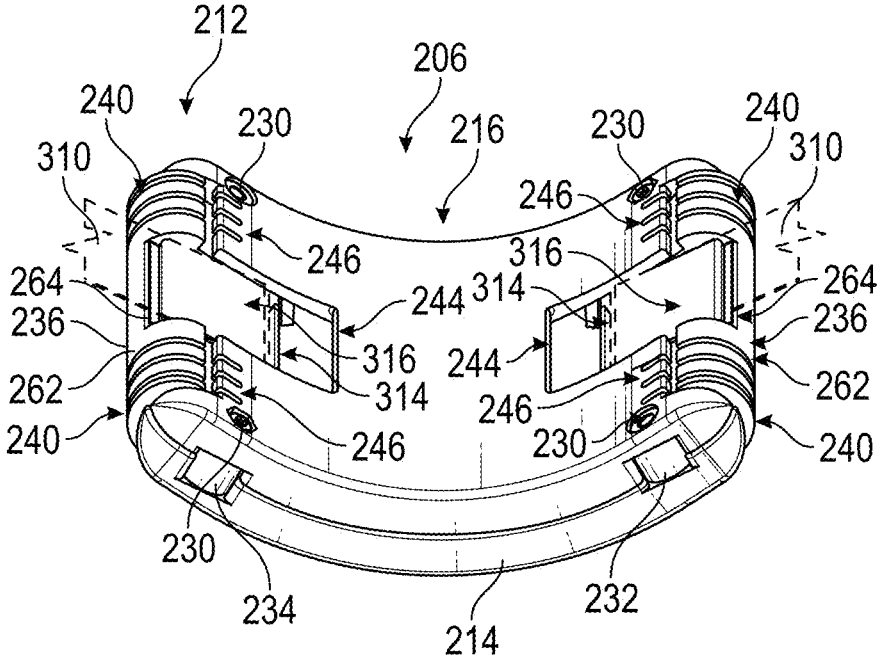

As illustrated in FIG. 16E, the sleds 314 can be disposed over the second levers 234 such that the heads or engagement portions 318 thereof are hooked over the second levers 234 and/or first levers 232 and the tongues 316 and strips 310 are disposed in the slots 264 of the slides 236. As illustrated in FIGS. 16F and 16G, the base 216 can then be aligned and positioned onto the cover 214 such that the wires 298 are routed through channels disposed on an interior surface of the base 216 as described herein. The base 216 can be advanced until contacting the cover 214, as shown in FIG. 16H. The slack in the wire 298 can be removed due to the curvature of the base 216. The fasteners 230 can be secured into place, in some variants, using nuts, such that the compression actuator unit 206 is assembled as shown in FIGS. 16J and 16K.

As described herein, a controller can apply an electrical input to the wire 298 causing the contraction thereof such that the slide 236 is pulled toward and/or into the housing 212 to push the first levers 232 and second levers 234. The rotation of the first levers 232 and the second levers 234 can, in turn, push against the heads or engagement portions 318 of the sleds 314 such that the sled 314 move towards each other, pulling the strips 310. The strips 310 can be coupled to straps and/or other features of the compression garment to pull them into tension, resulting in the compression garment applying compression to the anatomical feature of the user. In some variants, a controller that can apply an electrical input to the wire 298 can be disposed in the recess 334 in the exterior surface 215 of the cover 214.

Figure 17:
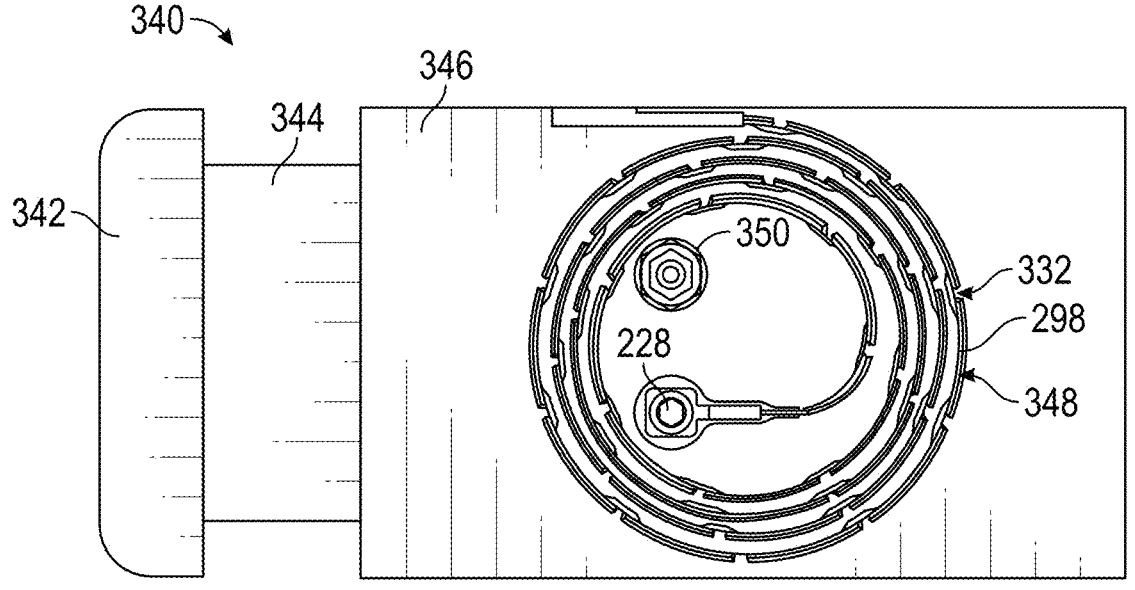
FIG. 17 illustrates a compression actuator unit with a spiral channel in a surface of the housing.

FIG. 17 illustrates a compression actuator unit 340. The compression actuator unit 340 can include a housing 346. A D ring 342 disposed on the end of a tongue 344 can be translated in and out of the housing 346. The D ring 342 can be secured to a strap and/or other feature of the compression garment, such that translating the D ring 342 towards the housing 346 tensions the strap and/or other feature of the compression garment to apply compression to the user. The housing 346 can include a spiral channel 348 disposed thereon in which a wire 298, as described herein, can be disposed. The channel 348 can include one or more retention features 332, which can also be referred to as tabs, to hold the wire 298 therein. The spiral shape can enable a large quantity of wire 298 to be routed through the channel 348. The wire 298 can extend from a fastener 228 mounted on the face of the housing 346, through the spiral channel 348, and engage, directly or indirectly, with a feature of the tongue 344 and/or associated component such that contraction of the wire 298 can pull the D ring 342 towards the housing 346.

Figures 18A, 18B:
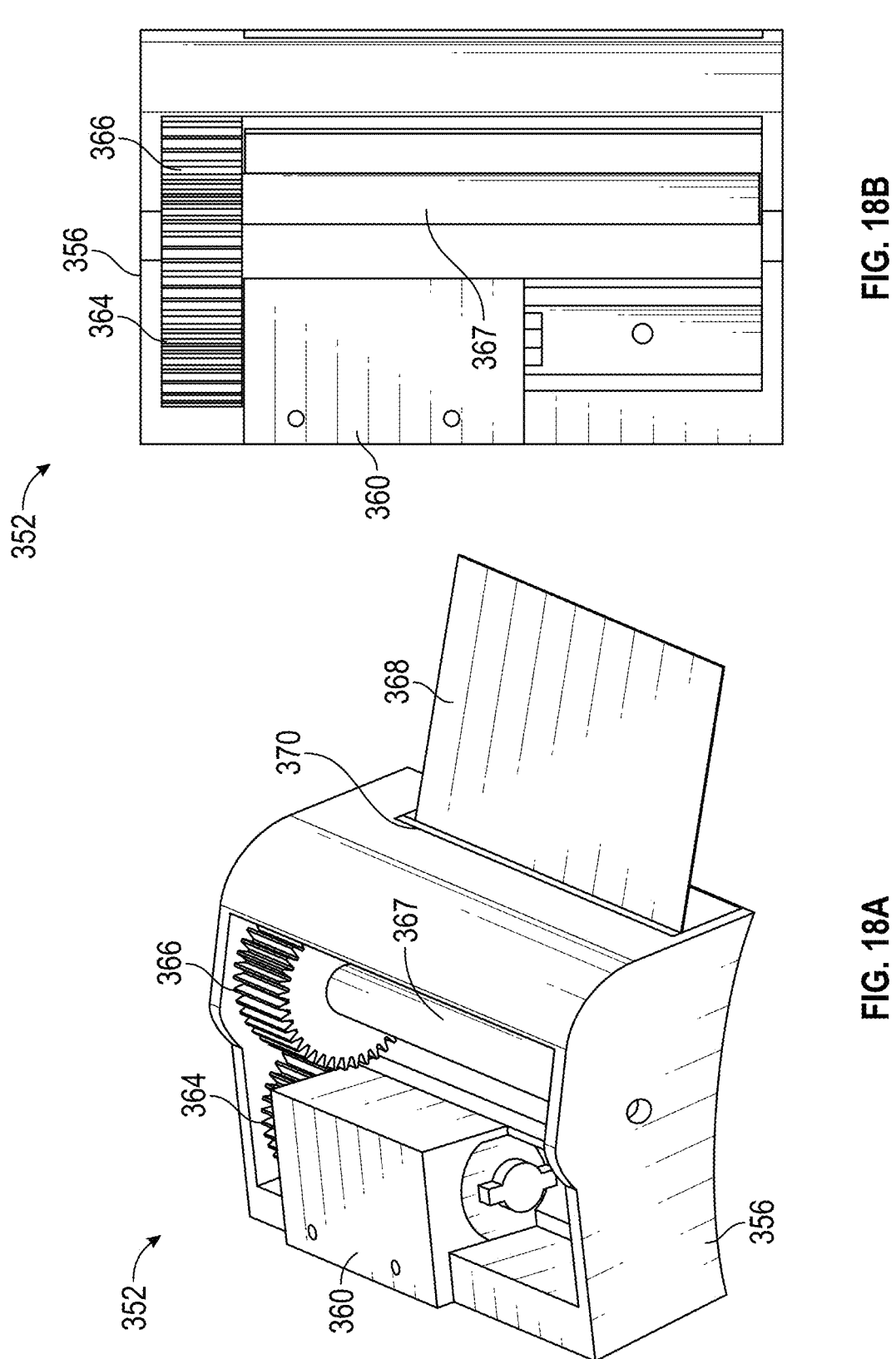
FIGS. 18A and 18B illustrate various views of a compression actuator unit with a motor.

FIGS. 18A and 18B illustrate a compression actuator unit 352 with a motor 360. The motor 360 can rotate a motor gear 364 which can, in turn, rotate a gear 366 connected to a spool 367 disposed on a fixed axle or shaft. A film 368, which can be a flexible material film, fabric, or strip, can be wrapped around the spool 367 and, via actuation by the motor 360, reeled up or reeled out. The film 368 can be incorporated into the strap and/or other feature of the compression garment such that reeling up the film 368 can tension the strap and/or other feature of the compression garment to apply compression to the user. Conversely, unreeling the film 368 can release the strap and/or other feature to reduce compression applied to the user. The film 368 can extend out of an opening 370 in a base 356 housing the motor 360, motor gear 364, gear 366, and spool 367. In some variants, the spool 367 can reel up and unreel wire, which can enable any of the embodiments herein to employ a compression actuator unit 352 with a motor 360.

Figures 19A, 19B, 19C:
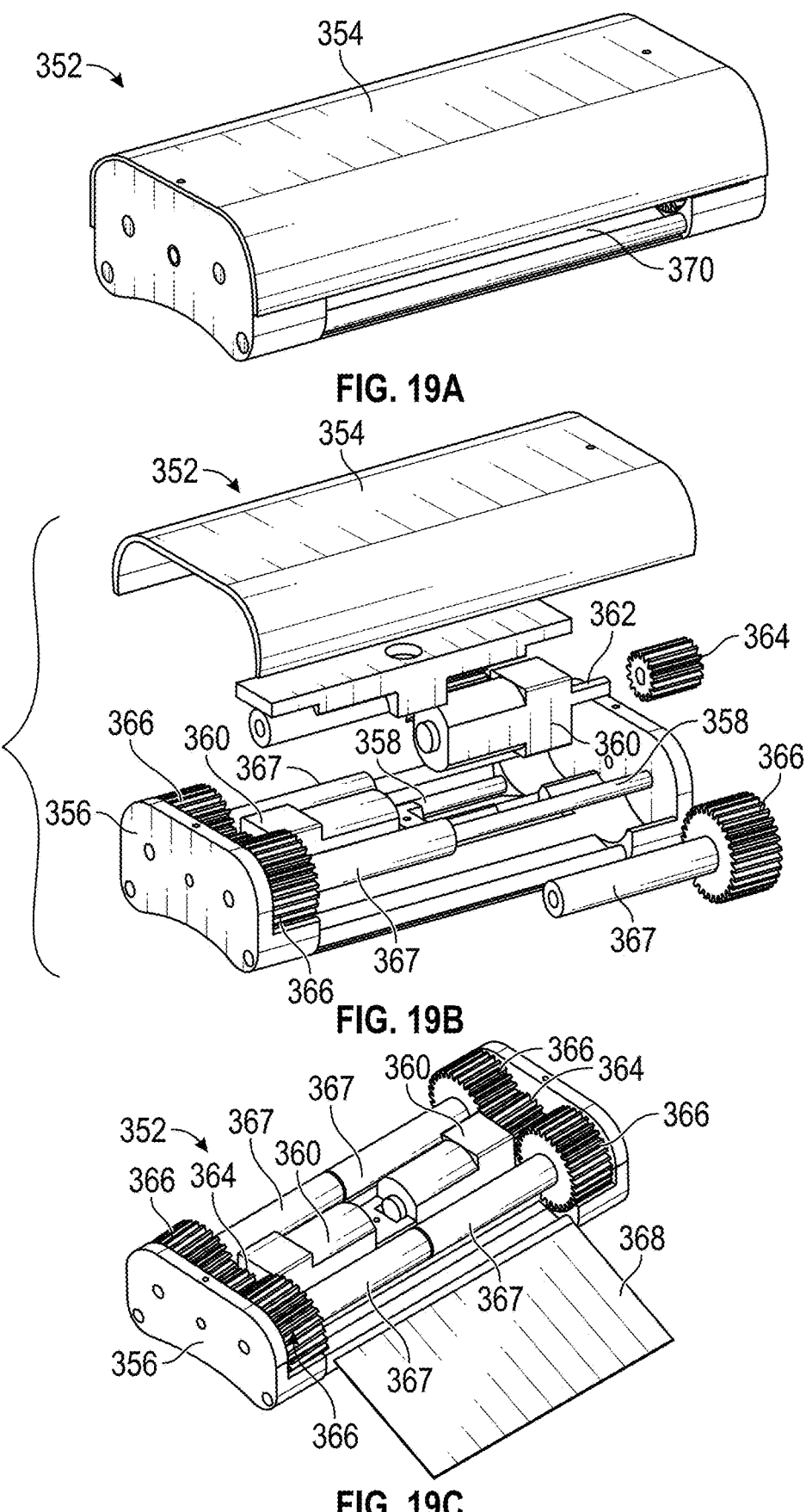
FIGS. 19A, 19B, and 19C illustrate various views of a compression actuator unit with two motors.

FIGS. 19A, 19B, and 19C illustrate a compression actuator unit 352 with a plurality (e.g., two) of motors 360. The motors 360 can include an axle 362 on which a motor gear 364 can be disposed. The motors 360 can be actuated to rotate the motor gear 364 which can, in turn, rotate two gears 366 attached to spools 367 disposed on fixed axles 358. A film 368, which can be a flexible material film, fabric, or strip, can be wrapped around the spools 367 and, via actuation by the motor 360, reeled up or reeled out. The films 368 can be incorporated into the strap and/or other feature of the compression garment such that reeling up the films 368 can tension the strap and/or other feature to apply compression to the user. Conversely, unreeling the film 368 can release the strap and/or other feature to reduce compression applied to the user. The film 368 can extend out of an opening 370 in a base 356 housing the motors 360, motor gears 364, gears 366, and spools 367. In some variants, the use of two motors 360 can enable a wider film 368 to be reeled up and unreeled. In some variants, the spools 367 can reel up and unreel wire, which can enable any of the embodiments here to employ a compression actuator unit 352 with motors 360. In some variants, different films of material can be wrapped around the spools 367. In some variants, the same film of material can be wrapped around the spools 367.

Figure 20:
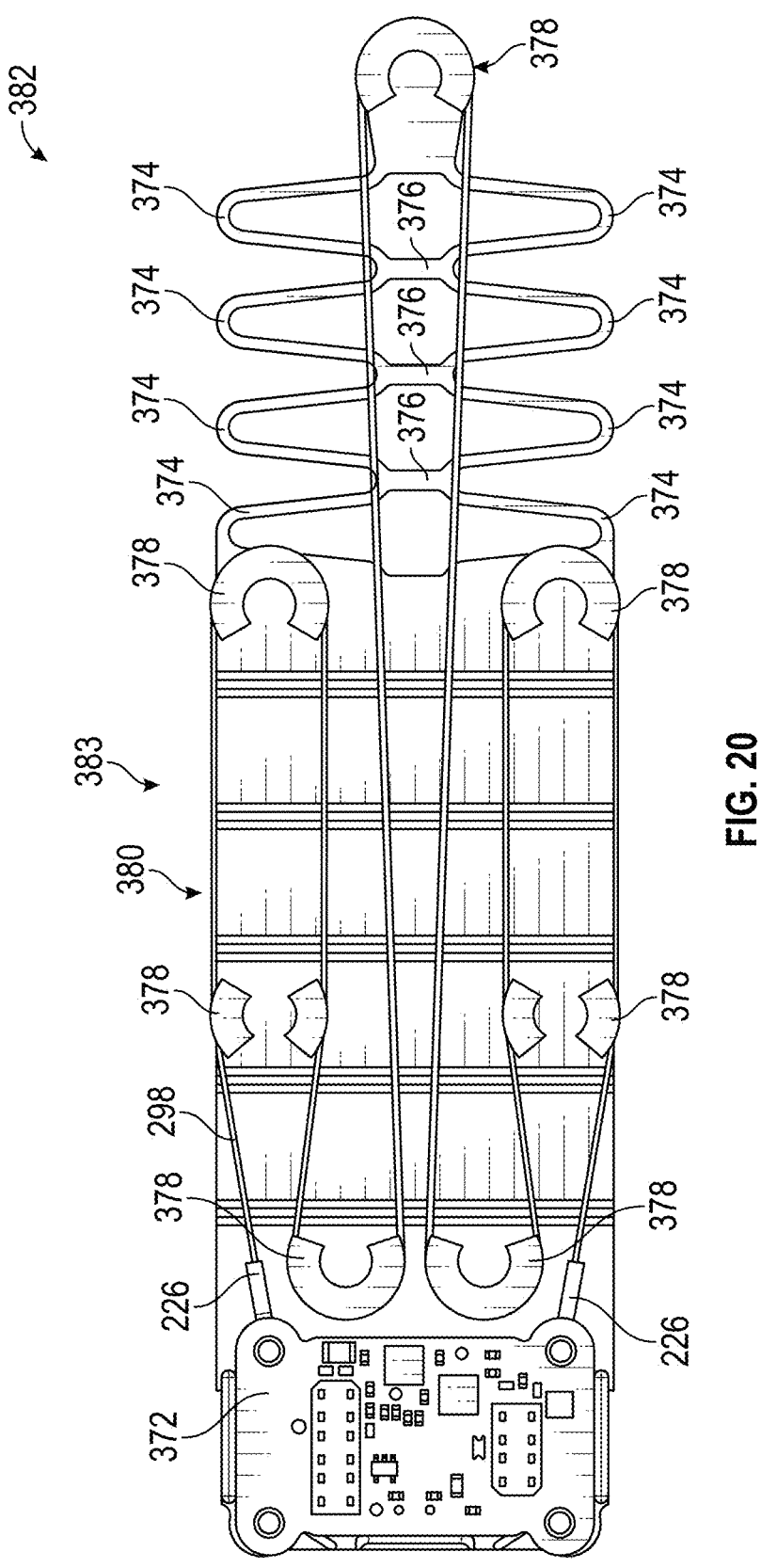
FIG. 20 illustrates a flex frame assembly.

FIG. 20 illustrates a flex frame assembly 382. The flex frame assembly 382 can include a flex frame 383, which can be made of a variety of materials. The flex frame 383 can include one or more portions that can flex under compression. The flex frame 383 can include a base 380. The base 380, in some variants, can flex under compression. In some variants, the base 380 does not flex under compressive forces during use on a patient. The flex frame assembly 382 can include a micro-electronic controller 372, which can also be referred to as a printed circuit board assembly or controller. The micro-electronic controller 372 can be used in any configuration described herein and apply an electrical input to a wire 298, which can be made of a shape memory material, and/or control the motor(s) 360 described herein. SMA leads 226 can be coupled to the micro-electronic controller 372 and a wire 298 can extend therefrom and be wrapped around one or more features of the flex frame 383. For example, the flex frame assembly 382 can include guides 378 which can include C-shaped structures around which the wire 298 can be wrapped such that, when the wire 298 contracts, the flex frame 383 shortens in length to tension a strap and/or other feature of a compression garment attached to the flex frame 383. The flex frame 383 can include a plurality of spring arms 374 (e.g., springs) that extend outward toward lateral sides of the flex frame 383 and back in toward bridges 376 disposed between adjacent spring arms 374. The spring arms 374 can be configured to deflect under compression. In some variants, the wire 298 can extend away from the SMA leads 226 to wrap around two guides 378, extend back toward the micro-electronic controller 372 and wrap around two guides 378 positioned proximate the micro-electronic controller 372, and extend away from the micro-electronic controller 372 to a guide 378 disposed on an end of the flex frame 383, which can include an end of a plurality of spring arms 374 and bridges 376, as shown in FIG. 20. Guides 378 can be disposed between the wire 298 as the wire 298 doubles back on itself.

Figure 21A:
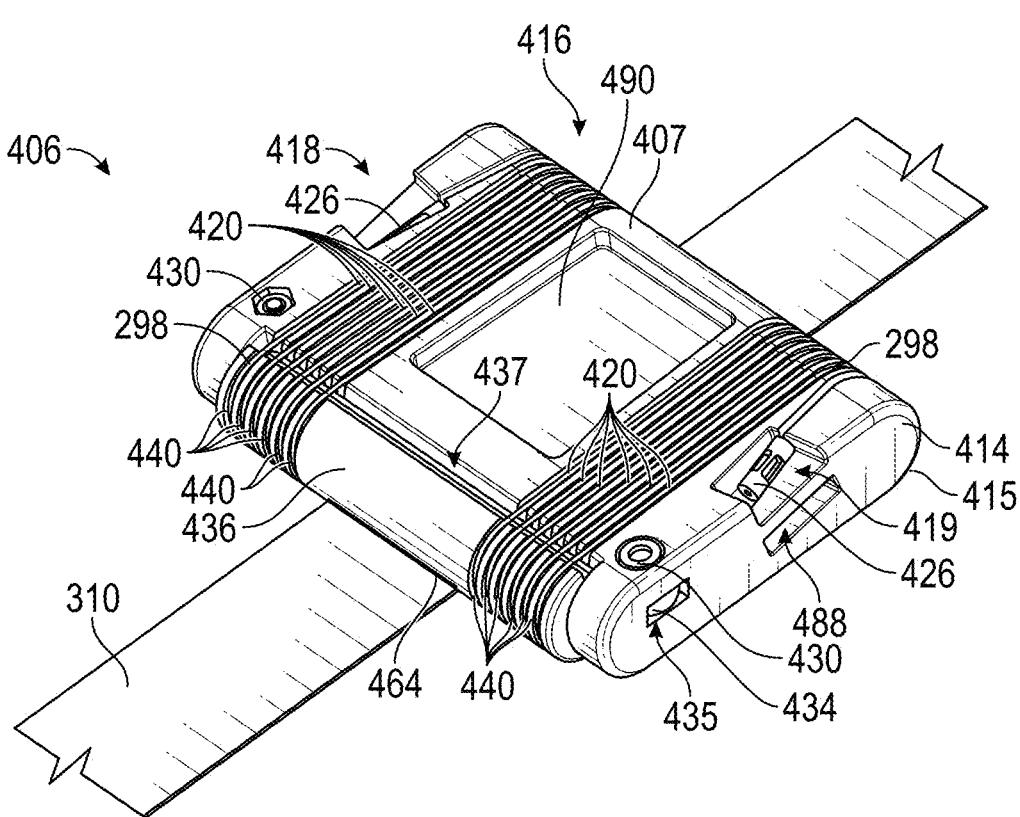
Figure 21B:
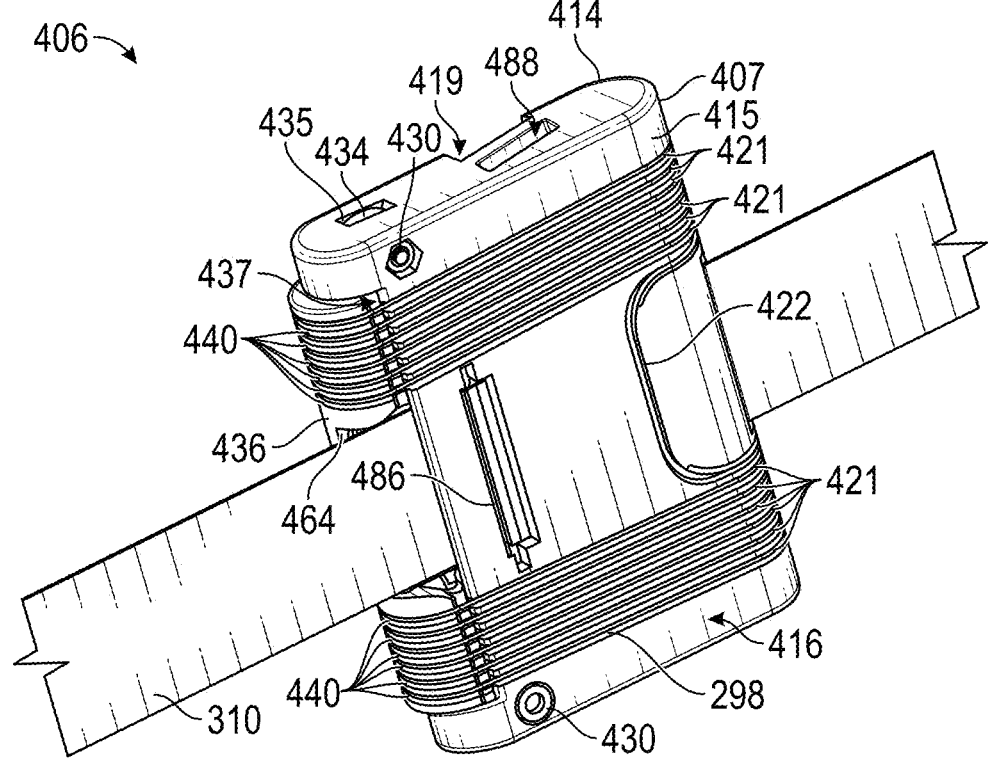

FIGS. 21A and 21B illustrate various views of a compression actuator unit 406, which can also be referred to as an actuator unit, actuator, constrictor, tensioning unit, etc. The compression actuator unit 406 can include a curved periphery and/or profile, which can correspond to the curved surface of a user's limb and/or other anatomical feature. The compression actuator unit 406 can include a periphery having flat surfaces. The compression actuator unit 406 can include a housing 416. The housing 416 can include a cover 414 and a base 216, which can be coupled together via a one or more fasteners 430 (e.g., rivets, bolts, screws, or the like). One or more compression actuator units 406 can be incorporated into a compression garment, such as the compression garment 200, to apply compression to an anatomical feature of a user as described herein. The compression actuator unit 406 can include any of the features and/or characteristics described in reference to compression actuator unit 206.

The housing 416 (e.g., the cover 414 and/or base 415) can include one or more features (e.g., channels, grooves, etc.) to house or retain a wire 298 or the like. The wire 298 can be wrapped around features of the housing 416 and a slide 436 extending out of an opening in the housing 416. For example, the wire 298 can be wrapped around the exterior of the housing 416 and slide 436 such that, upon contraction of the wire 298, the slide 436 moves into the housing 416, which can include remaining partially outside the housing 416. For example, the housing 416 (e.g., the cover 414 and/or base 415) can include a recess 418 and/or recess 419. The recess 418 and/or recess 419 can house or retain leads 426 therein. The leads 426 can be shape memory alloy (SMA), shape memory polymer (SMP), and/or another shape memory material leads. The leads 426 can be the beginning and/or ending portion of the wire 298 or coupled to the wire 298 or the like. The wire 298 can be made of a SMA, SMP, and/or another shape memory material. The leads 426 can be connected to a controller, e.g., microcontroller, that can apply an electrical input and/or heat thereto, resulting in the heating of the wire 298 or the like. The heating of the wire 298 can contract the wire 298 as described herein.

The housing 416 (e.g., the exterior surfaces thereof) can include one or more channels or grooves 420, as shown in FIG. 21A. The channels 420 can be disposed on the cover 414 and/or upper surface of the housing 416 (e.g., more distal relative to the anatomical feature of the user when incorporated into a compression garment worn by the user). The channels 420 can extend from the recess 419 and/or recess 418 where the leads 426 can be stowed. The housing 416 (e.g., the exterior surface thereof) can include one or more channels or grooves 421, as shown in FIG. 21B. The channels 421 can be disposed on the base 415 and/or lower surface of the housing 416 (e.g., more proximal relative to the anatomical feature of the user when incorporated into a compression garment worn by the user).

The wire 298 can be routed from the lead 426 disposed in the recess 419 to one channel 420 of the multiple channels 420 to wrap around a curved surface 407 of the housing 416 to one channel 421 of the multiple channels 421 in the lower surface or base 415. The wire 298 can be routed through the channel 421 to a slide 436 (e.g., slide) disposed in an opening of the housing 416 (e.g., between the cover 414 and base 415). The slide 436 can extend out from inside the housing 416. The wire 298 can be routed around the slide 436 via a channel 440 of multiple channels 440 disposed in the exposed curved surface of the slide 436 back to another channel 420 of the multiple channels 420 disposed on the upper surface of the housing 416 (e.g., cover 414). The wire 298 can be routed through the channel 420, around the curved surface 407, another channel 421, another channel 440 of the slide 436, and back to another channel 420 for one or more iterations (e.g., 2, 3, 4, 5, 6, 7, or more). The wire 298 can be routed through the one or more iterations until being routed through a curved channel 422 in the lower surface (e.g., base 415), as shown in FIG. 21B, and back to another channel 420 without being routed around the slide 436. The wire 298 can then be routed through another channel 420, channel 440 of the slide 436, another channel 421, around the curved surface 407, and back to another channel 420 for one or more iterations (e.g., 2, 3, 4, 5, 6, 7, or more) until terminating at the lead 426 disposed in the recess 418, as shown in FIG. 21A. In some variants, the wire 298 can be coated, which can include being coated in a polymer such as a SNIP.

When electrical input is applied to the wire 298, the wire 298 can contract, moving the slide 436 farther into and/or toward the housing 416. In the unactuated configuration, gaps 437 can be disposed between at least a portion of the slide 436 and the housing 416 (e.g., cover 414 and base 415), and as the wire 298 contracts, the gap 437 can be decreased. The slide 436 can move further into and/or toward the housing 416 as the wire 298 contracts. The movement of the slide 436 can cause corresponding movement of the strap 310 (e.g., strip, belt, band, cable, etc.) inward toward the housing 416, which can tension the strap 310 and/or other features of a compression garment attached to the strap 310 to apply a compressive force to the limb or other anatomical feature of the user. In some variants, both portions of the strap 310 extending away from the housing 416 can be pulled inward with contraction of the wire. In some variants, one side of the strap 310 extending from the housing 416 can be pulled inward toward the housing 416.

The housing 416 can include a recess 490. The recess 490 can be disposed in the upper surface (e.g., exterior surface of the cover 414). The recess 490 can receive a controller, such as a microcontroller therein, that can apply an electric current to the leads 426 of the wire 298 to cause the wire 298 to contract.

The compression actuator unit 406 can include a plurality of levers, which can be disposed in the housing 416. The slide 436 can contact, directly or indirectly, and rotate the plurality of levers. The rotated levers can pivot to translate a sled coupled to the strap 310 to tension of the strap 310. The sled can be disposed in the housing 416. The levers can be pivotably secured to the housing 416 by fasteners 430. A portion of the levers can be exposed via one or more openings 435. The levers can amplify the impact of the movement of the slide 436, causing the strap 310 to move a greater distance than the slide 436. The levers can amplify the movement of the strap 310 compared to the slide 236 by up to at least one thousand percent (e.g., 100, 200, 300, 400, 500, 600, 700, 800, 900, 1000, or more percent).

The housing 416 can include one or more openings 488 (e.g., recesses). The openings 488 can be used for a variety of purposes. For example, the openings 488 can be used to secure the compression actuator unit 406 to the compression garment, link one or more compression actuator units 406 together, and/or other purposes.

The housing 416 (e.g., base 415) can include an opening 486, as shown in FIG. 21B, into an internal cavity of the housing 416. The opening 486 can be used to position one or more components within the housing 416.

Figure 22A:
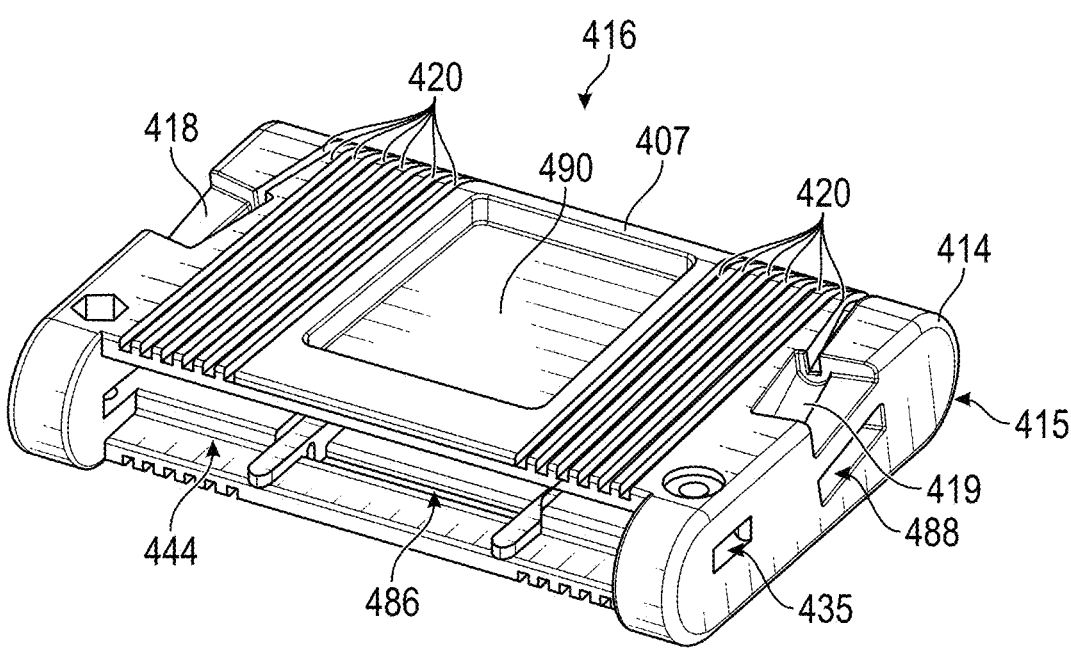
FIGS. 22A and 22B illustrate various views of a housing.
Figure 22B:
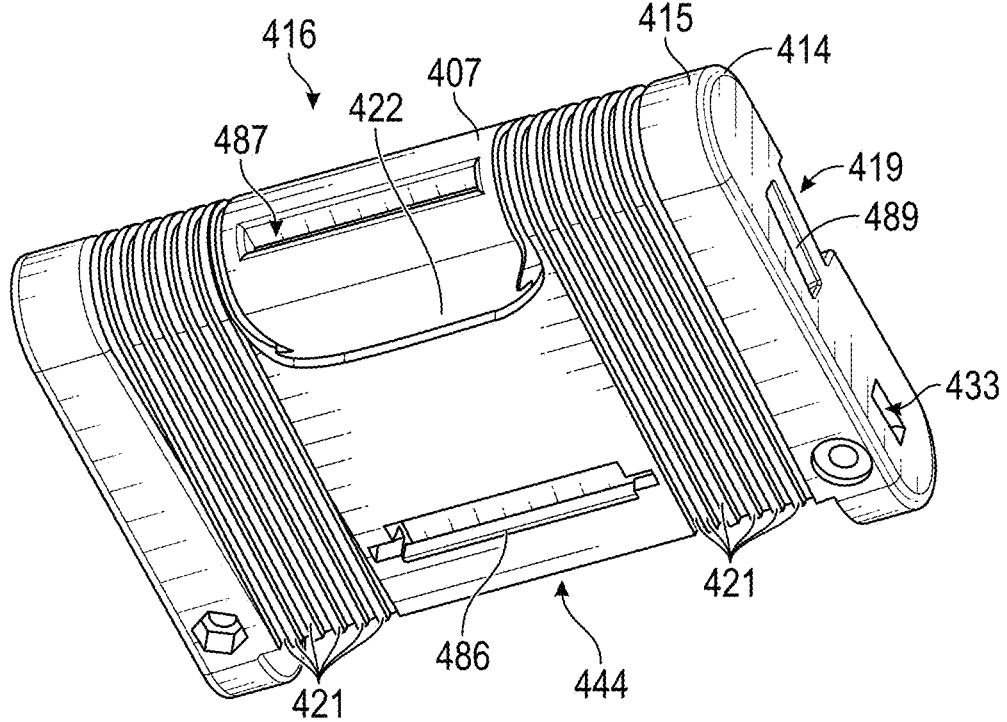

FIGS. 22A and 22B illustrate various views of the housing 416. The housing 416 can include an opening 444 to receive the slide 436. The opening 444 can receive the slide 436, which can include at least a portion of the slide 436, therein. The opening 44 can be defined by the cover 414 and the base 415.

Figure 23A:
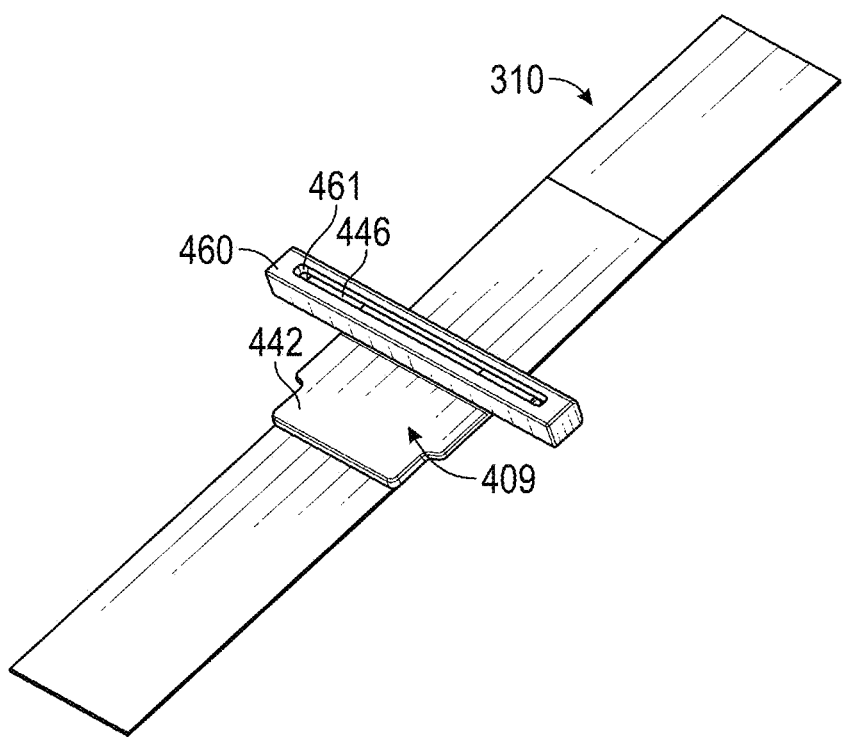
FIGS. 23A and 23B illustrate various views of a sled and strap assembled together.
Figure 23B:
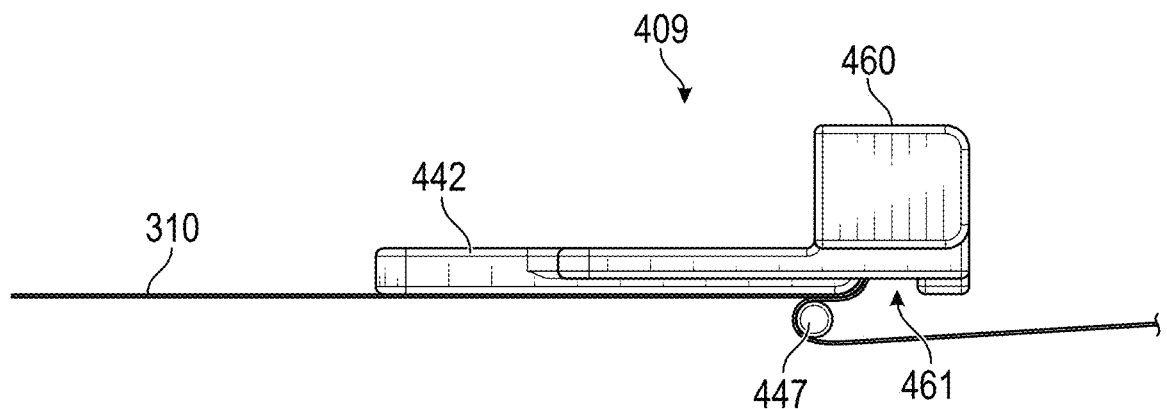

FIGS. 23A and 23B illustrate various views of a sled 409 coupled to the strap 310. The sled 409 can include an engagement portion 460, which can also be referred to as a head or enlarged portion. The engagement portion 460 can be translated (e.g., pushed) by the plurality of levers to tension the strap 310.

The engagement portion 460 can include a slot 461. The slot 461 can receive a doubled-over portion of the strap 310 therein. The doubled-over portion of the strap 310 can be retained within the slot 461 by a first rod 446. For example, the strap 310 can be looped around the first rod 446. The end portions of the first rod 446 can rest upon and/or be retained by ledges and/or contours defining a periphery of the slot 461, holding the first rod 446 in place and preventing the strap 310 from inadvertently decoupling from the sled 409. In some variants, a fastener, clip, or the like can couple the first rod 446 to the engagement portion 460.

The sled 409 can include a tongue 442. The tongue 442 can extend away from the engagement portion 460. The width of the tongue 442 can be greatest adjacent the engagement portion 460 and narrower spaced away from the engagement portion 460. The tongue 442 can be generally flat.

The strap 310 can be looped around a second rod 447, as shown in FIG. 23B. As described herein, the second rod 447 can be biased by a spring to pretension the strap 310 before applying an electrical current to the wire 298 to move the slide 436 as described herein. Alternatively, the second rod 447 can be biased by a spring to limit the force applied by the compression actuator unit 406. In some variants, the second rod 447 is fixedly coupled to the housing 416.

Figure 24A:
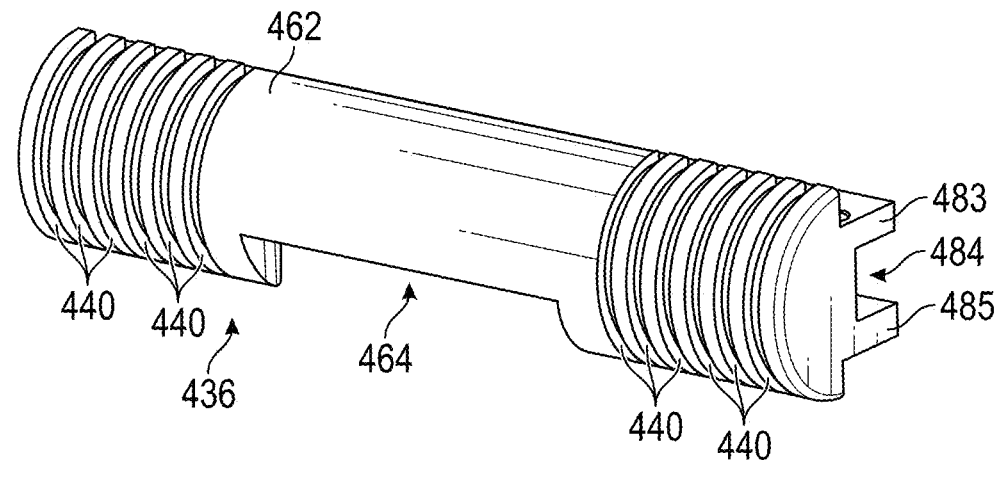
FIGS. 24A and 24B illustrate various views of a slide.
Figure 24B:
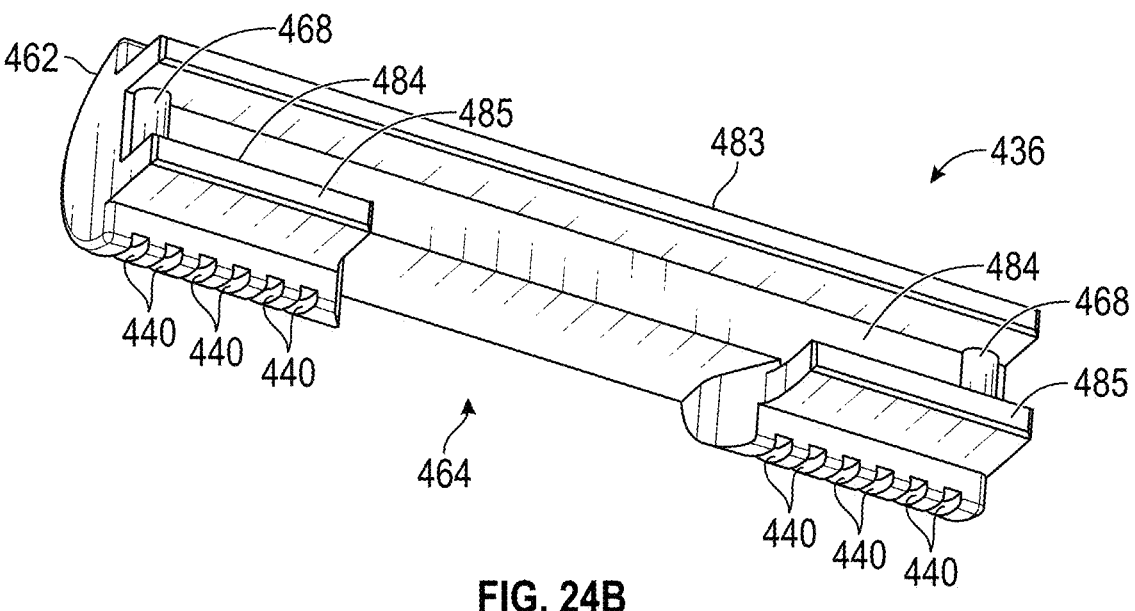

FIGS. 24A and 24B illustrate various views of the slide 436. The slide 436 can include a curved surface 462 that can be positioned outside of the housing 416 when assembled with the housing 416. The channels 440 through which the wire 298 or the like can be routed can be disposed in the curved surface 462. The slide 436 can include a slot 464, which can be sized to allow the tongue 442 of the sled 409 and/or strap 310 therethrough. The slide 436 can include gaps 484 (e.g., slots, recesses, etc.) that can receive the levers therein. The slide 436 can include a first flange 483 (e.g., top flange) and/or second flange 485 (e.g., bottom flange). The first flange 483 and second flange 485 can be disposed on opposing sides of the gaps 484. In some variants, the first flange 483 can extend the entirety of the length of the slide 436. The second flange 485 can be disrupted by the slot 464. The slide 436 can include protrusions 468 (e.g., bumps, raised surfaces, rods, pins, etc.) that can contact and push against a portion of the levers when the slide 436 is moved inward toward the housing 416 via contraction of the wire 298 (e.g., during actuation). During actuation, the wires or the like can contract, pulling the slide 436 inward toward the housing 416 such that the protrusions 468 contact and push the levers. The levers can rotate to push against the engagement portion 460 of the sled 409, translating the sled 409 within the housing 416 and tensioning the strap 310 and/or other features of the compression garments attached thereto. The protrusions 468 can be disposed in the gap 484. In some variants, the protrusions 468 can be rods or pins that are disposed through a portion of the slide 436, such as the first flange 483 and/or second flange 485.

Figures 25A, 25B:
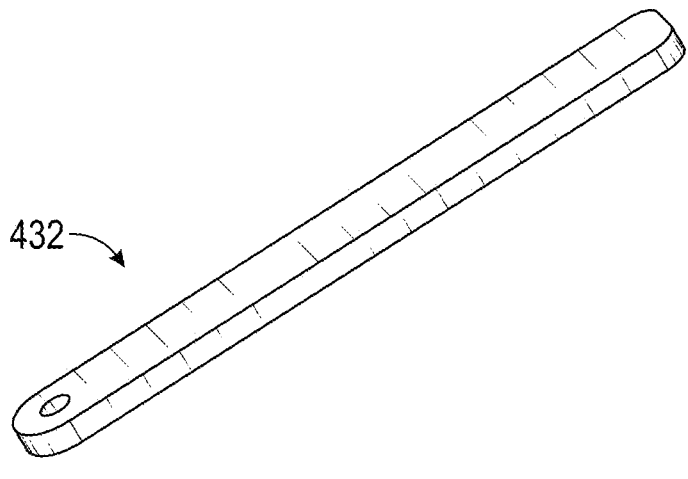
FIGS. 25A and 25B illustrate various views of a lever.

FIGS. 25A and 25B illustrate various views of the first lever 432, which can also be referred to as an arm, limb, member, etc. The first lever 432, as described herein, can be secured to the housing 416. For example, the fastener 430 can couple one end of the first lever 432 to the housing 416 such that the first lever 432 rotates a free end about the fastener 430. The first lever 432 can include rounded ends. The first lever 432 can have various shaped cross-sections, including rectangle, square, circular, oval, irregular, etc. The first lever 432 and a second lever 434 can be the same or different from each other (e.g., size, shape, material, profile, etc.).

Figures 26A, 26B:
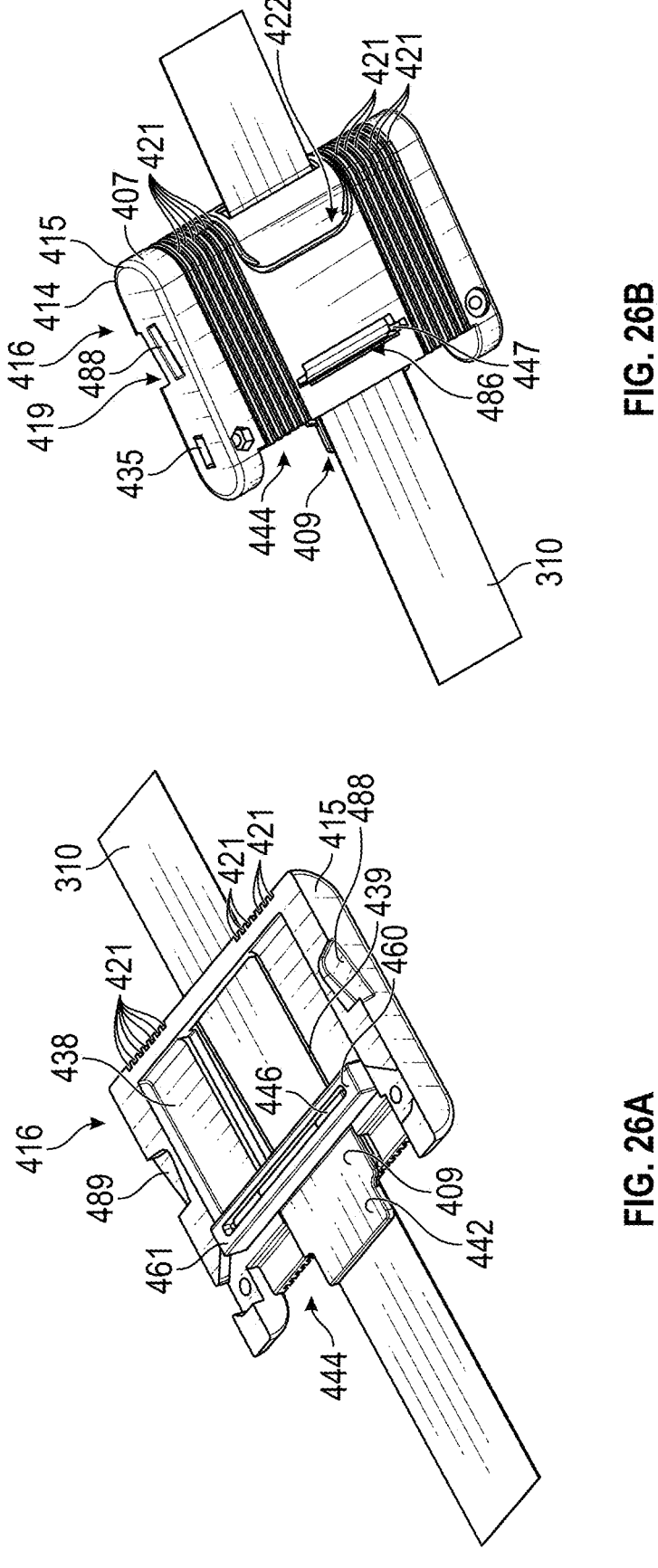
FIGS. 26A and 26B illustrate various views of the sled and strap assembled together and disposed in the housing.

FIGS. 26A-26D illustrate various views of a portion of the housing 416 (e.g., base 415) with the sled 409 and strap 310 assembled therein. As shown in FIG. 26A, the tongue 442 of the sled 409 can be disposed within a slot 439, also referred to as a track, of the housing 416 (e.g., base 415). The tongue 442 can translate (e.g., move, slide) within the slot 439 during actuation of the compression actuator unit 406. The engagement portion 460 of the sled 409 can be disposed within a cavity 438, also referred to as a slot or track, of the housing 416 (e.g., base 415). The engagement portion 460 can translate (e.g., move, slide) within the cavity 438. The walls of the housing 416 (e.g., base 415) can ensure that movement of the engagement portion 460 within the cavity 438 is linear translation. The strap 310 can be disposed in the slot 439 and translate therein during actuation of the compression actuator unit 406.

Figure 26C:
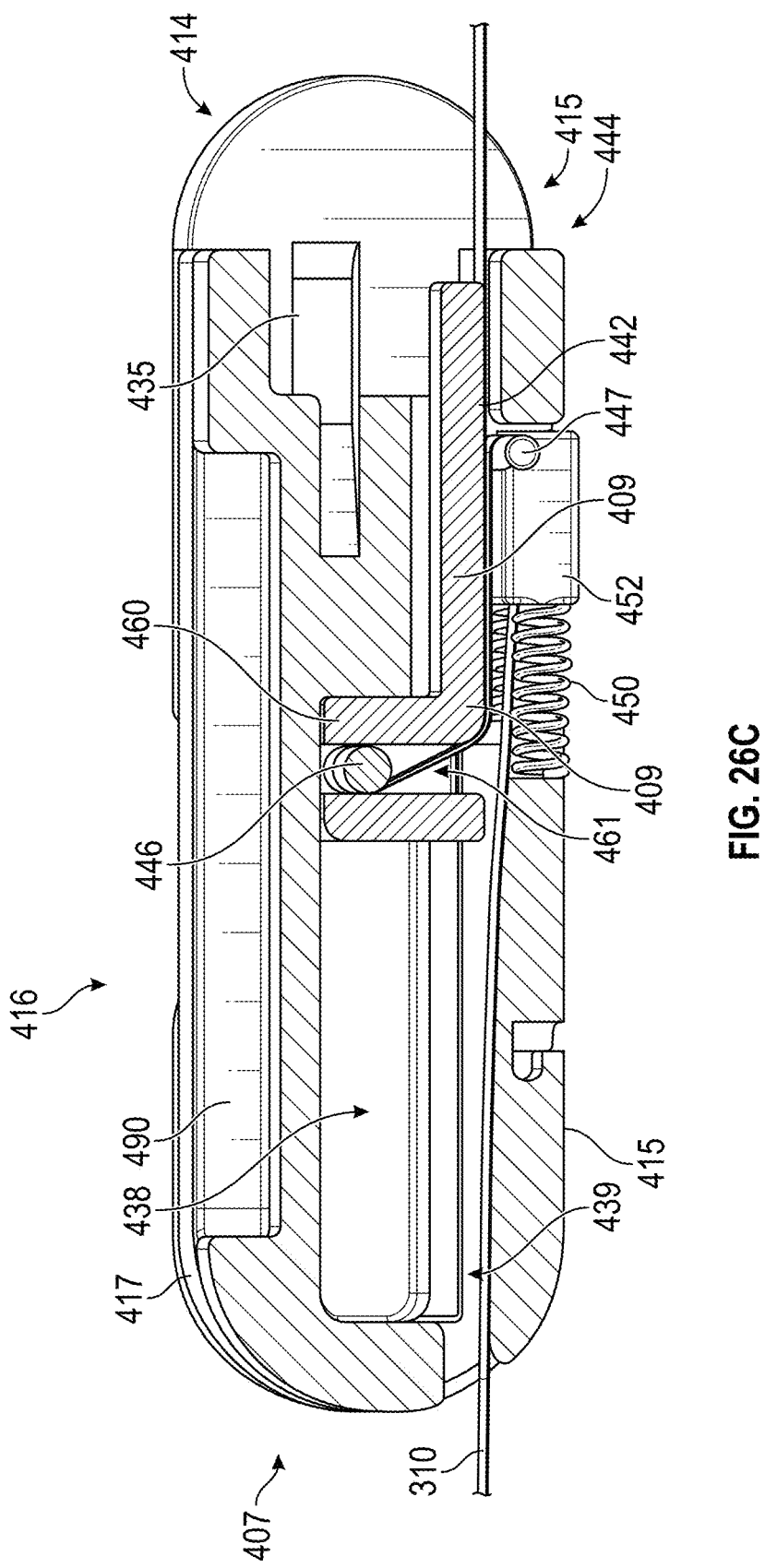
FIG. 26C illustrates a section view of the housing with the assembled sled and strap therein, along with a receiver biased by a spring.

FIG. 26C illustrates a section view of the housing 416 (e.g., cover 414 and base 415) with the sled 409 and strap 310 disposed therein. As described herein, the strap 310 can be looped around (e.g., doubled-over around) a first rod 446 retained in the slot 461 of the engagement portion 460. The first rod 446 can be retained within the slot 461 by one or more ledges and/or contours of the engagement portion 460.

The strap 310 can enter the housing 416 via the opening 444 to be positioned in the slot 439. The strap 310 can be disposed under the tongue 442 of the sled 409, routed up into the slot 461 of the engagement portion 460, around the first rod 446, down out of the slot 461, around the second rod 447 (e.g., doubled-over), and through the slot 439 to exit the housing 416 on an opposite side as the opening 444 of the housing 416. The looping of the strap 310 around the first rod 446 and second rod 447 can be referred to as a pulley system and/or arrangement.

The second rod 447 can be retained (e.g., housed) by a receiver 452 (e.g., retainer). In some variants, the receiver 452 holding the second rod 447 can be biased in a direction with one or more springs 450. For example, the receiver 452 can be biased in a direction opposite the direction of movement of the sled 409 during compression. The biasing of the receiver 452 with the second rod 447 can apply a pretension to the strap 310 before actuation by the compression actuator unit 406, which can provide a baseline pressure to the user or limit the outgoing force of the compression actuator unit 406. The biasing of the receiver 452 can provide some give in the compression actuator unit 406 for user comfort. The receiver 452 can be housed within a slot and/or cavity of the housing 416. In some variants, the second rod 447 can be fixed in place. In some variants, the second rod 447 itself can be biased in a direction without the receiver 452.

During actuation, the slide 436 can move inward to rotate one or more levers to displace the sled 409. The displacement of the sled 409 can pull the strap 310 looped around the first rod 446, causing more of the strap 310 to be pulled into the housing 416 to apply compression to the wearer. For example, the portion of the strap 310 extending out of the housing 416 in the unactuated configuration can be pulled into the housing 416 in an actuated configuration.

Figure 26D:
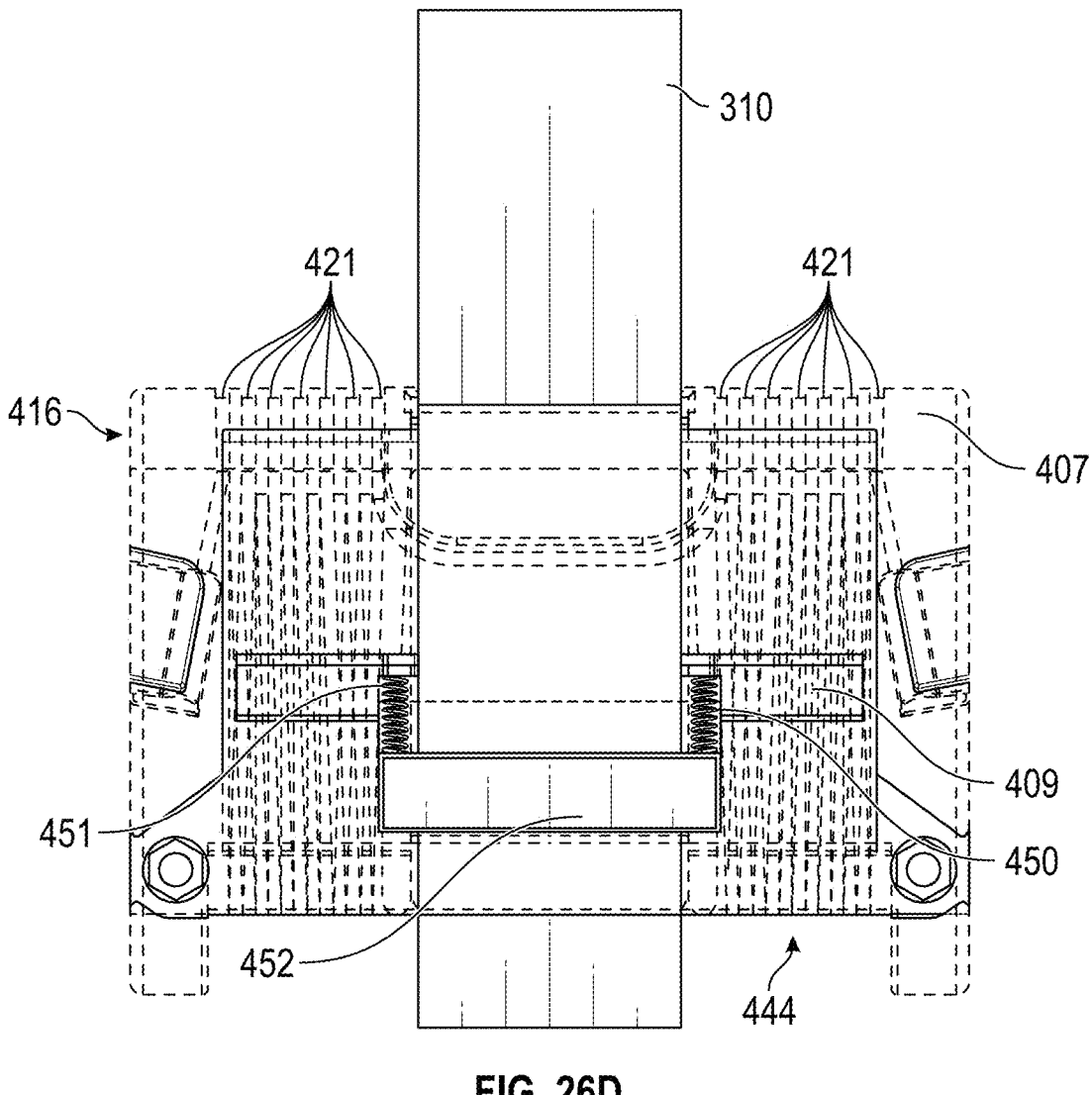
FIG. 26D illustrates the housing transparently to show the sled, strap, retainer, and springs.

FIG. 26D illustrates a view of the housing 416 (e.g., cover 414 and base 415) with the sled 409 and strap 310 disposed therein with the housing 416 transparent. As illustrated, a second spring 451 can bias the receiver 452 in a direction.

Figure 27:
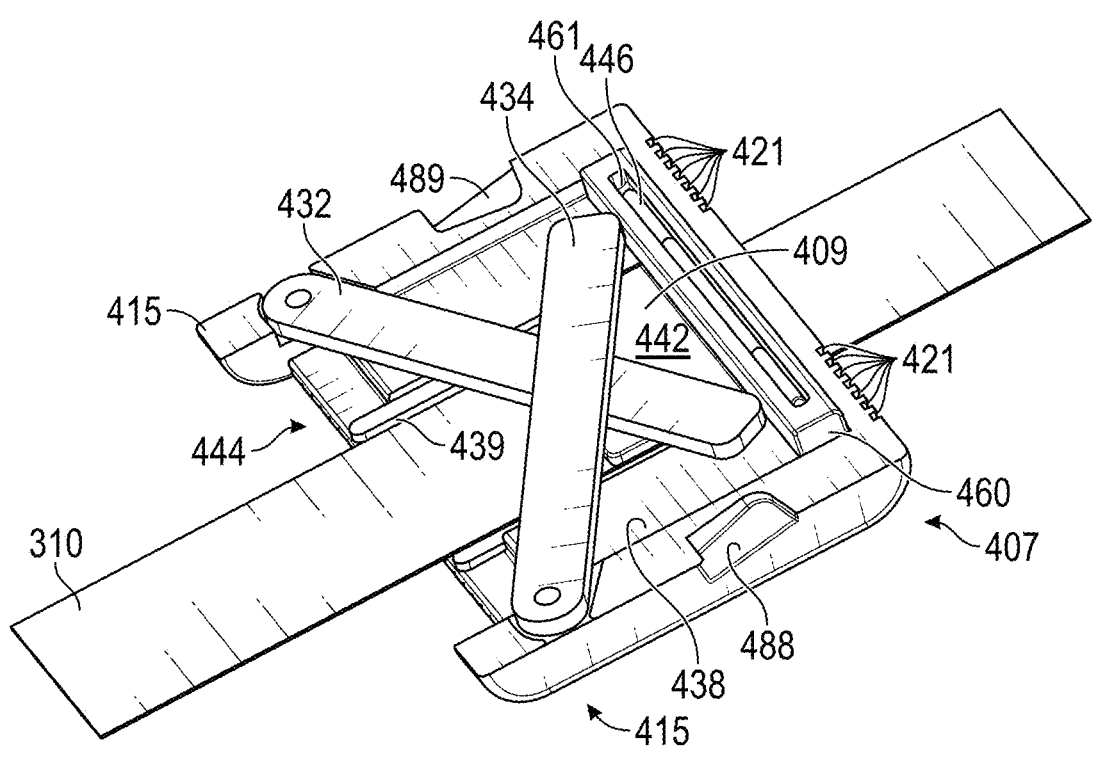
FIG. 27 illustrates the housing with levers positioned in an actuated expanded configuration to translate the sled and tension the strap.
Figure 28A:
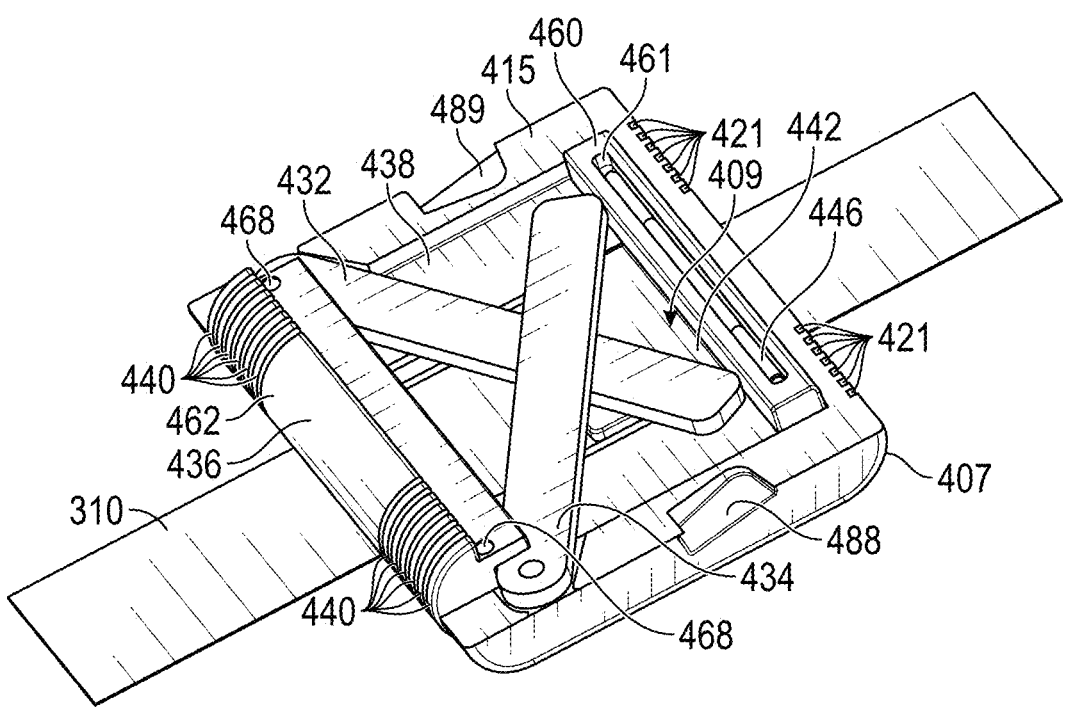
FIGS. 28A and 28B illustrates the compression actuator unit with a top portion (e.g., cover) removed to show the slide pushed against the levers to rotate them to an expanded (e.g., deployed) configuration.
Figure 28B:
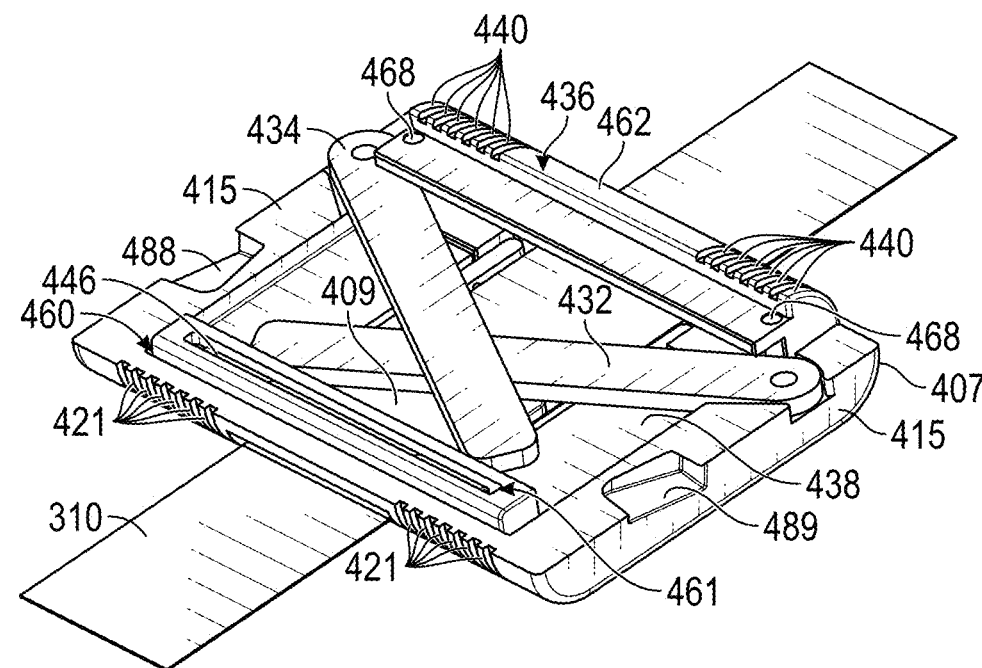

FIG. 27 illustrates a portion of the housing 416 (e.g., base 415) with the sled 409, strap 310, and a first lever 432 and second lever 434 in an actuated configuration. As described herein, the first lever 432 and second lever 434 can be rotatably fixed to the housing 416 at one end. As shown, free ends of the first lever 432 and second lever 434 are rotated inward to push against and translate the sled 409, causing the strap 310 to be tensioned. The second lever 434 can be positioned over the first lever 432 or vice versa. The first lever 432 and second lever 434 can be rotated into an "X" arrangement with the first lever 432 and second lever 434 crossing over each other. The free ends of the first lever 432 and second lever 434 can include curves to reduce binding or friction as the free ends rub and push against the engagement portion 460 of the sled 409 as the first lever 432 and second lever 434 are rotated into the expanded configuration to translate the sled 409 away from the opening 444 of the housing 416. As illustrated in FIGS. 28A and 28B, the slide 436 can push against and rotate the first lever 432 and second lever 434 that can, in turn, push against and translate the sled 409. Specifically, the protrusions 468 of the slide 436 can push against and cause the rotation of the first lever 432 and second lever 434.

Figures 29A, 29B:
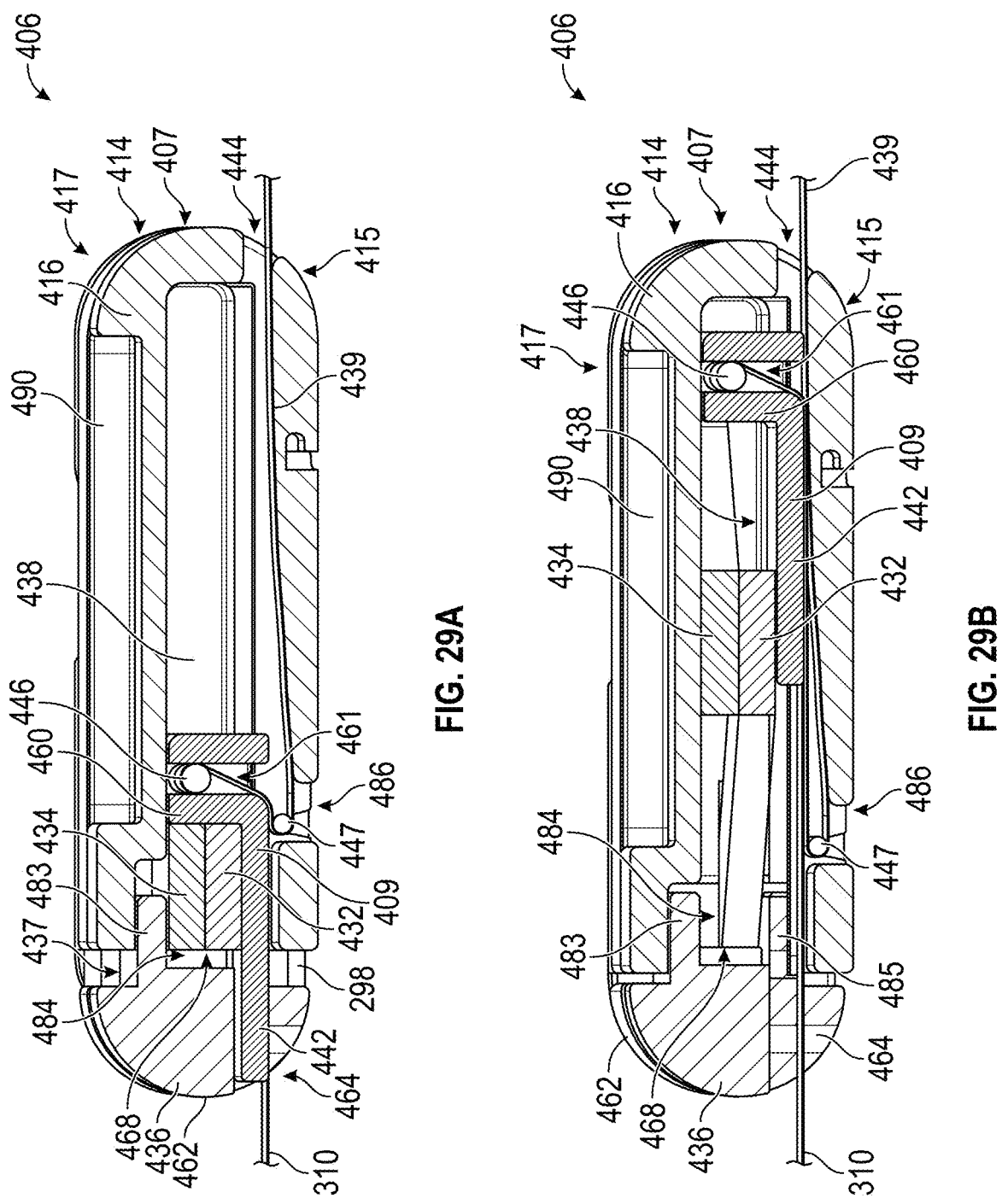
FIG. 29A illustrates a section view of the compression actuator unit in the unactuated collapsed configuration.
FIG. 29B illustrates a section view of the compression actuator unit in the actuated expanded configuration.

FIGS. 29A and 29B illustrate sectioned views of the compression actuator unit 406 with the housing 416 (e.g., cover 414 and base 415), slide 436, first lever 432, second lever 434, sled 409, and strap 310. FIG. 29A illustrates the compression actuator unit 406 in a collapsed unactuated configuration. In the collapsed unactuated configuration, the first lever 432 and second lever 434 can be disposed at least partially in the gap 484 of the slide 436. The first lever 432 and second lever 434 can be positioned in an overlapping arrangement such that the free ends of the first lever 432 and second lever 434 are positioned in an overlapping arrangement. The free ends of the first lever 432 and the second lever 434 can be positioned proximate the slide 436. The tongue 442 of the sled 409 can be disposed in the slot 464 of the slide 436. A gap 437 can extend between a portion of the slide 436 (e.g., portion of the slide 436 with the curved surface 462) and the housing 416. The first flange 483 and second flange 485 can extend into the opening 444 of the housing 416. The first flange 483 and second flange 485 can contact internal portions of the housing 416, which can direct movement of the slide 436 into linear translation.

FIG. 29B illustrates the compression actuator unit 406 in an expanded actuated configuration. In the expanded actuated configuration, the free ends of the first lever 432 and second lever 434 can be rotated away from the slide 436 to translate the sled 409 within the cavity 438 of the housing

416, pulling the strap 310 into the housing 416 to apply compression. As described herein, the wire 298 wrapped around the housing 416 and slide 436 can contract via the application of an electrical current, moving the slide 436 inward toward the housing 416 and decreasing the size of the gap 437. The slide 436 (e.g., protrusions 468) can push against the first lever 432 and second lever 434 to cause the first lever 432 and second lever 434 to rotate. The free ends of the first lever 432 and second lever 434 can push against the sled 409 (e.g., engagement portion 460) to translate the sled 409 within the cavity 438 of the housing 416 to tension the strap 310 (e.g., pull more of the strap 310 into the housing 416). The tongue 442 of the sled 409 can be moved out of the slot 464 of the slide 436, which can include the tongue 442 being positioned entirely within the housing 416.

Figure 30A:
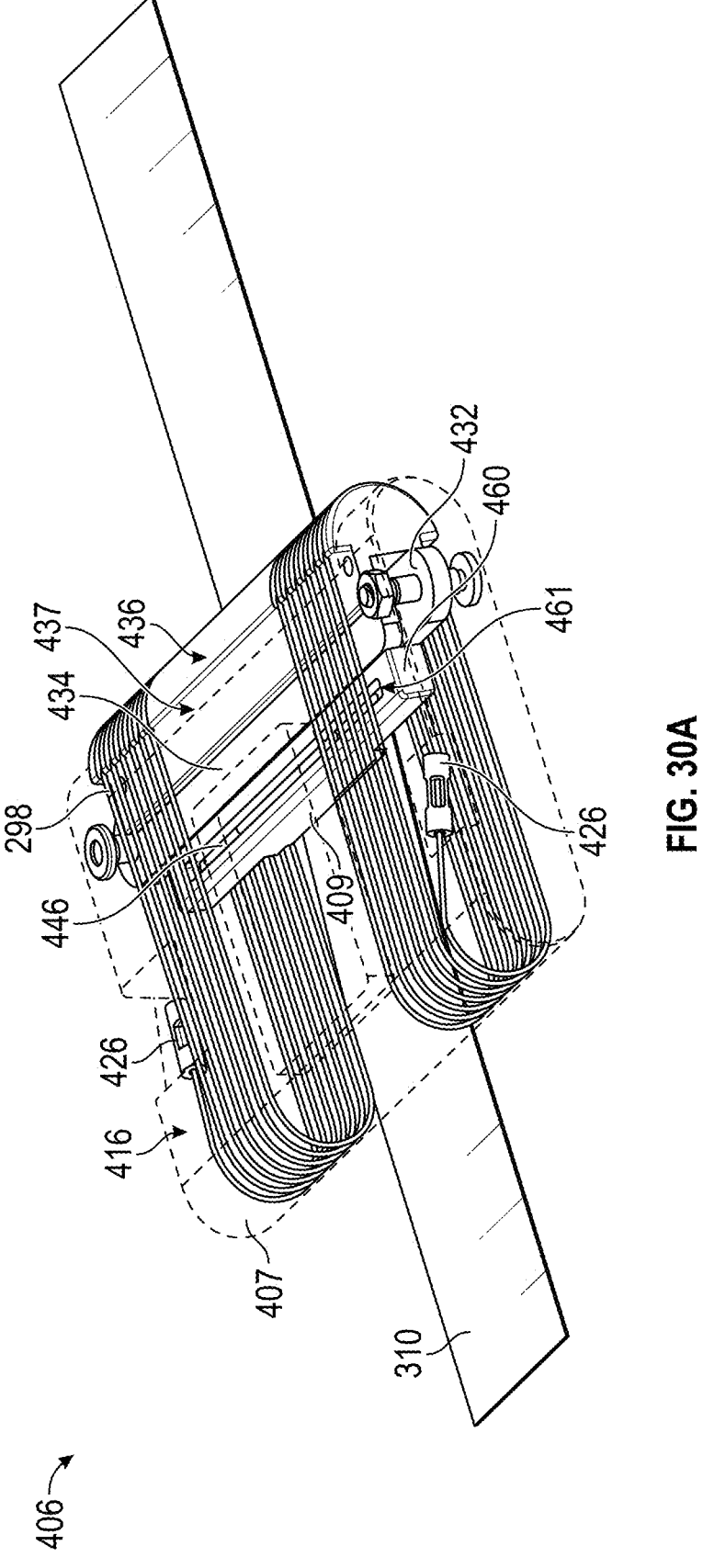
FIG. 30A illustrates a view of the compression actuator unit in the unactuated collapsed configuration with the wire wrapped around the housing, shown transparently, and slide.
Figure 30B:
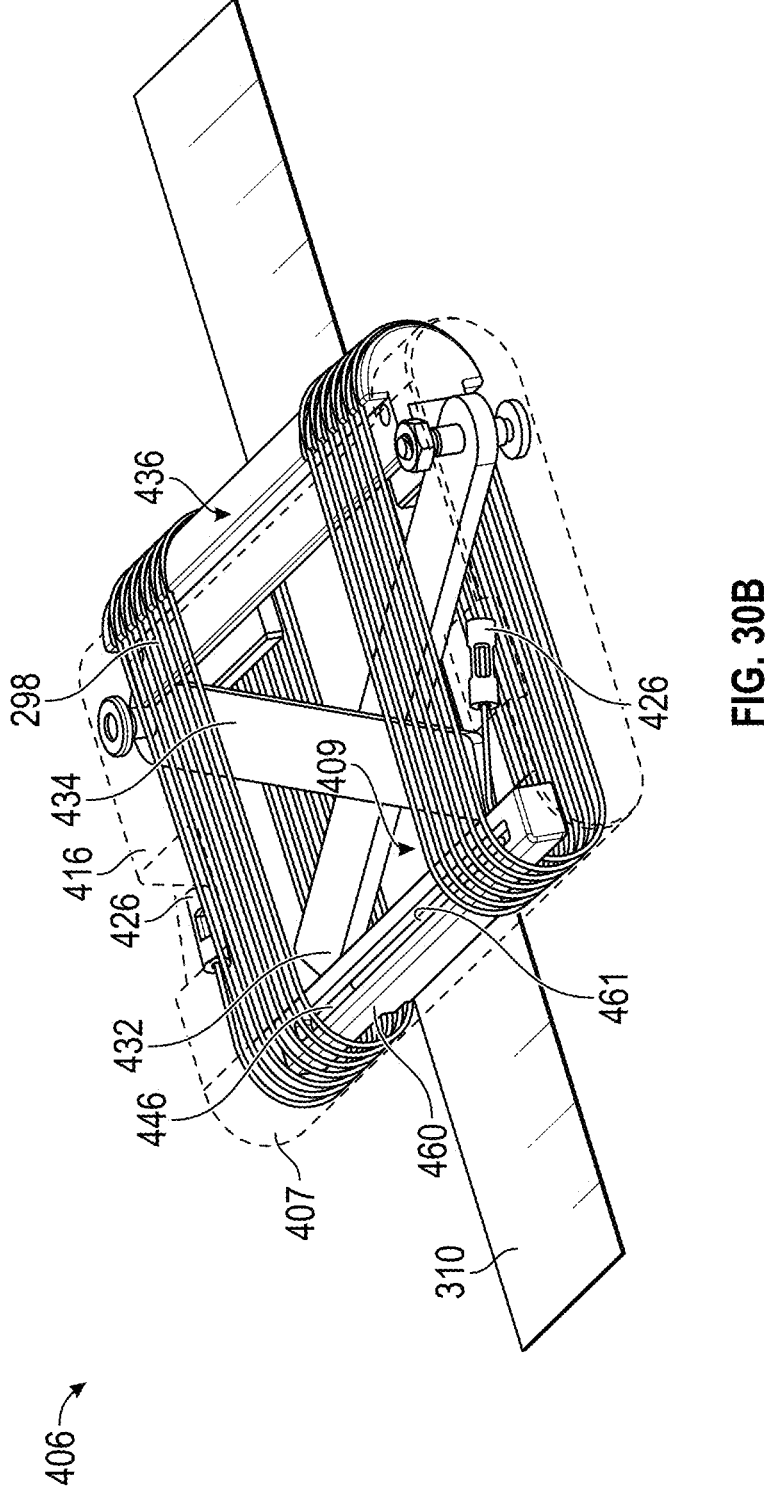
FIG. 30B illustrates a view of the compression actuator unit in the actuated expanded configuration with the wire wrapped around the housing, shown transparently, and slide.
Figure 30C:
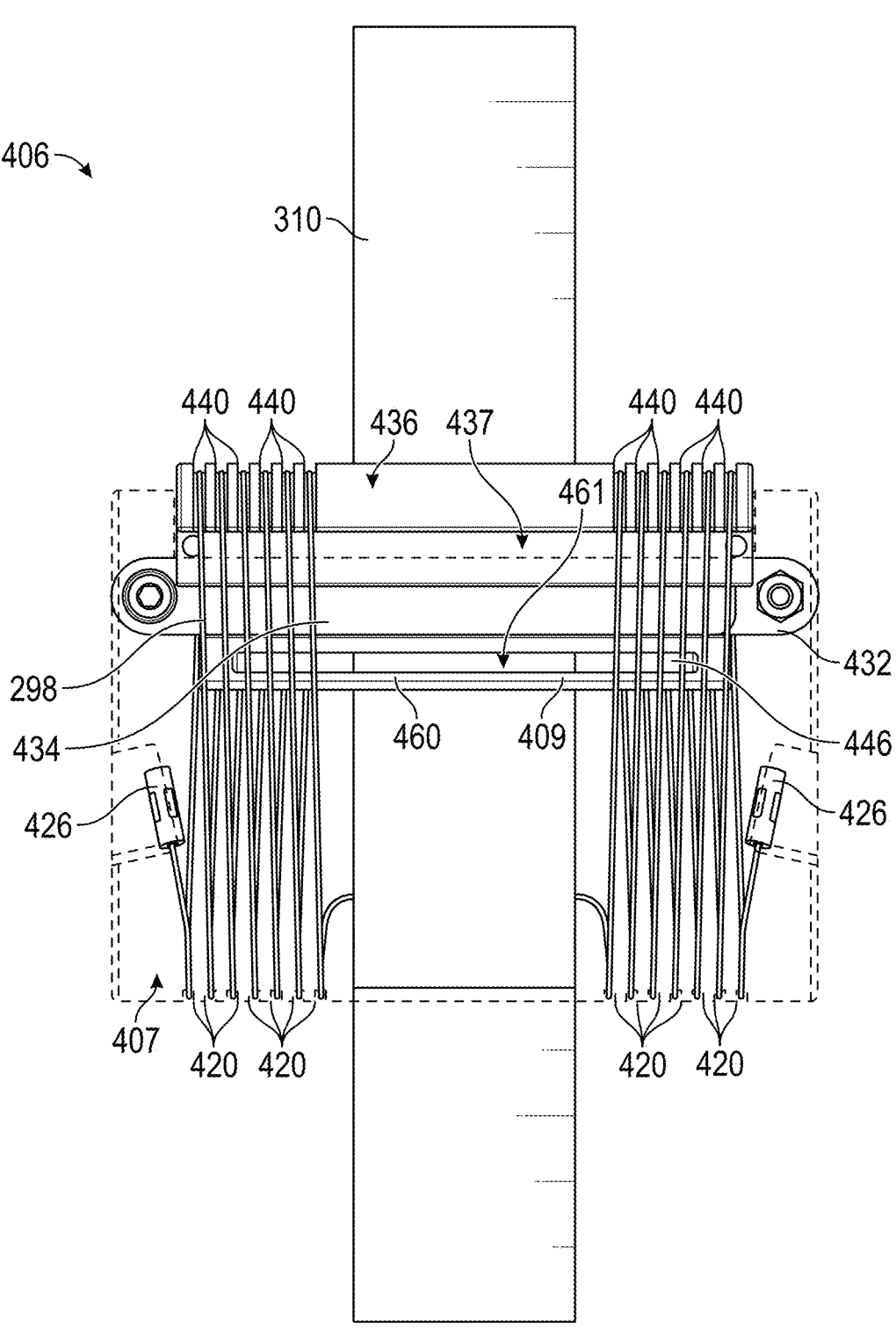
FIG. 30C illustrates a view of the compression actuator unit in the unactuated collapsed configuration with the wire wrapped around the housing, shown transparently, and slide.

FIGS. 30A-30D illustrate the compression actuator unit 406 with the housing 416 transparent. FIGS. 30A and 30C illustrate the compression actuator unit 406 in the unactuated collapsed configuration with the sled 409 and free ends of the first lever 432 and second lever 434 proximate the slide 436. As shown, a majority of an elongate side of the first lever 432 and second lever 434 can contact the engagement portion 460 in the collapsed configuration.

Figure 30D:
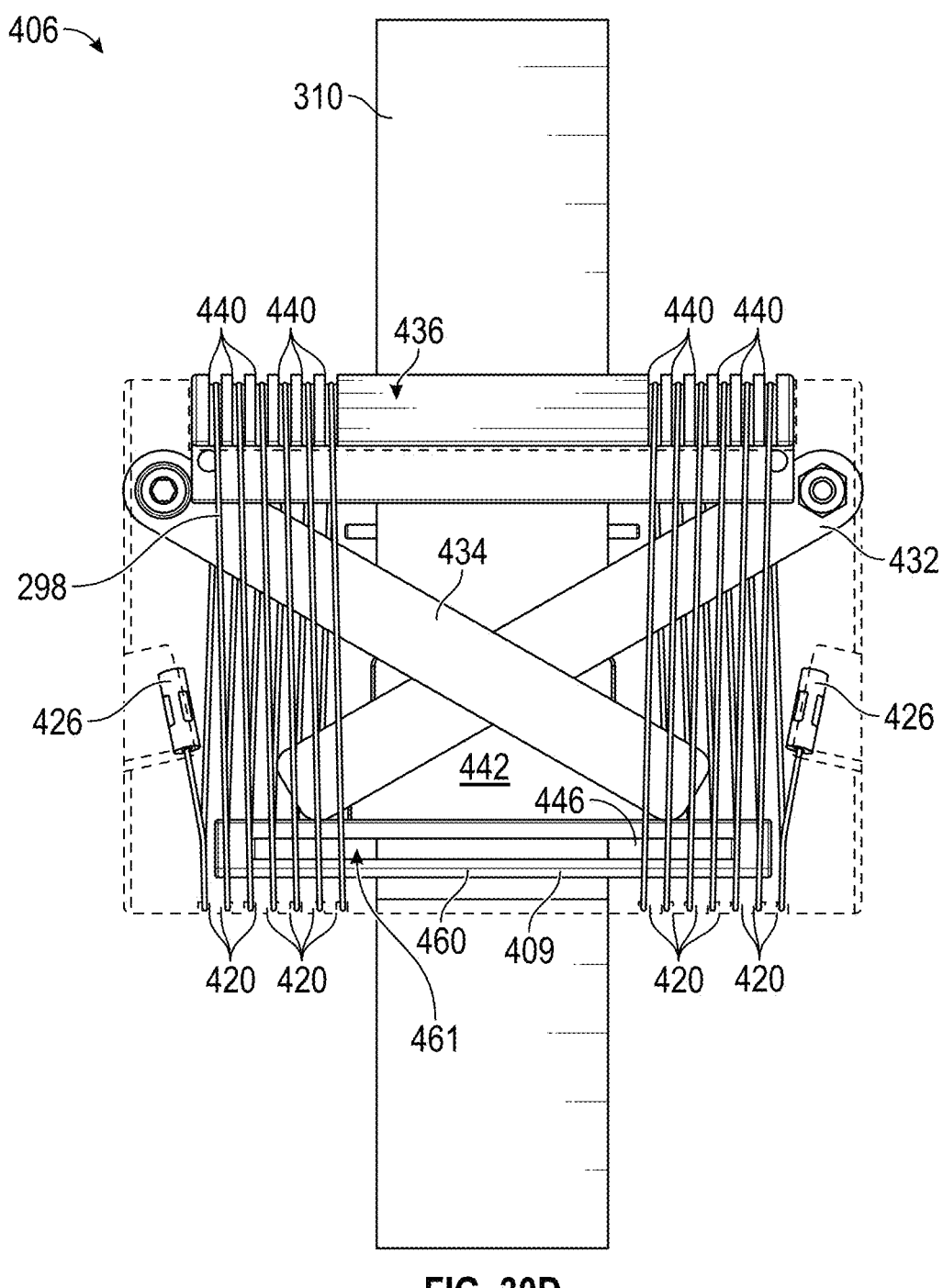
FIG. 30D illustrates a view of the compression actuator unit in the actuated expanded configuration with the wire wrapped around the housing, shown transparently, and slide.

FIGS. 30B and 30D illustrate the compression actuator unit 406 in the actuated expanded configuration with the sled 409 translated away from the slide 436 by the rotation of the first lever 432 and second lever 434 to tension the strap 310. The free ends of the first lever 432 and second lever 434 can push against the engagement portion 460 to translate the sled 409 within the housing 416. As illustrated, the second lever 434 can be moved above the first lever 432 to avoid collision. In some variants, the sled 409 can be translated to any position between the unactuated collapsed configuration and the actuated expanded configuration illustrated in FIGS. 30B and 30D.

Figure 31A:
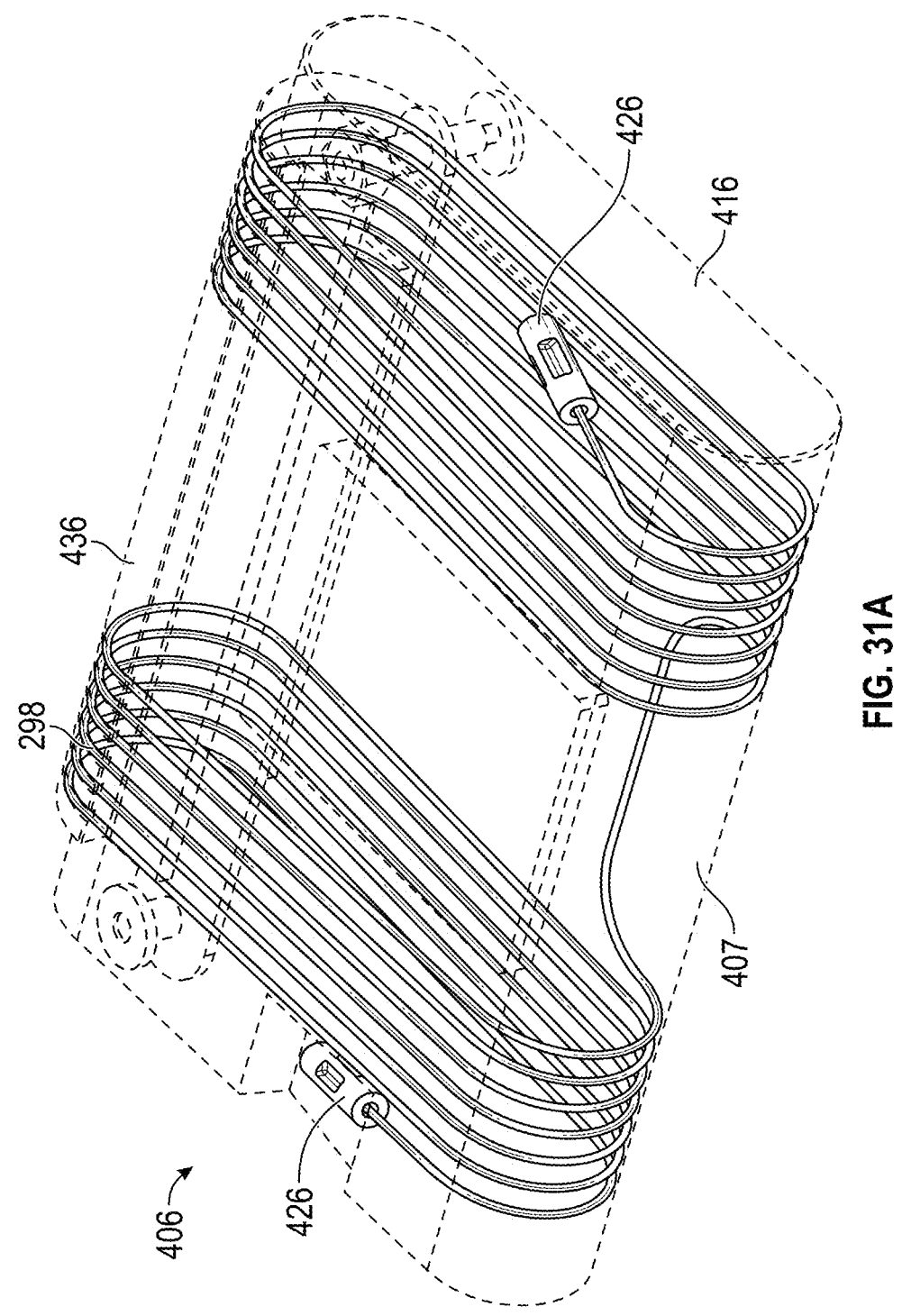
FIG. 31A illustrates the compression actuator unit transparently with the wire wrapped around the housing and slide.
Figure 31B:
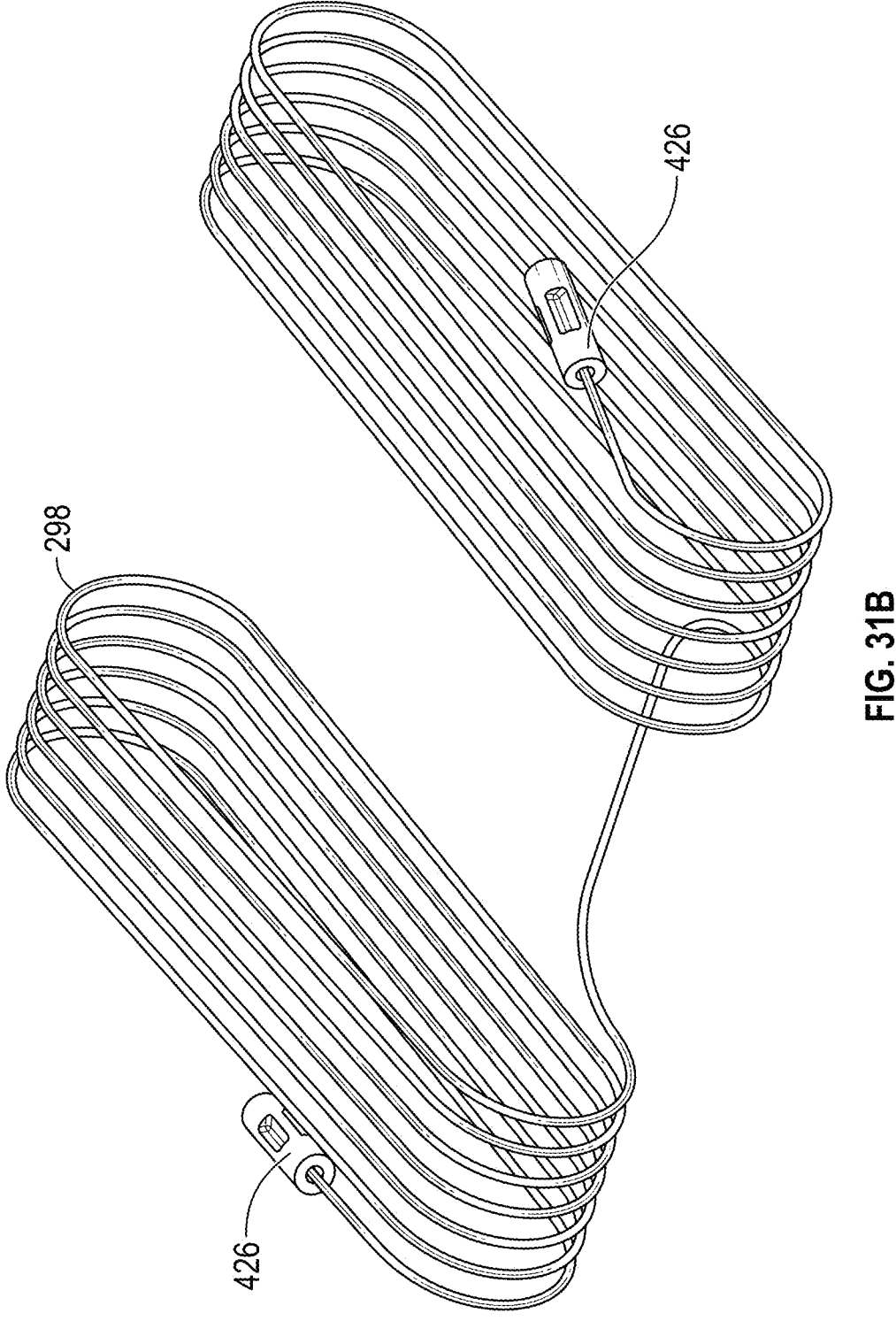
FIG. 31B illustrates the wire in the wrapped configuration but without the remainder of the compression actuator unit.

FIG. 31A illustrates the compression actuator unit 406 transparently with the wire 298 wrapped around the housing 416 and slide 436. FIG. 31B illustrates the wire 298 in the wrapped configuration but without the remainder of the compression actuator unit 406.

In some variants, multiple compression actuator units 406 and/or compression actuator units 206 can be incorporated into a compression garment. In some variants, multiple compression actuator units 406 and/or compression actuator units 206 can be coupled to a single strap 310 to apply compression. The compression actuator unit 406 and/or compression actuator unit 206 can be made of a variety of materials, which can at least include one or more polymers (e.g., plastic), metals, metal alloys, shape memory materials, etc. As described herein, a compression garment can incorporate one or more of the compression actuator unit 406 and/or compression actuator unit 206 described herein to provide compression to an anatomical feature of the user. In some variants, a controller can be connected to a plurality of microcontrollers that, respectively, control actuation of compression actuator units 406 and/or compression actuator units 206. The compression actuator units 406 and/or compression actuator units 206 can be activated simultaneously and/or in other patterns to apply compression, which can at least include applying compression from a distal portion of an anatomical feature of the user inward to a more proximal portion to move fluid within the anatomical feature of the user away from the distal portions of the anatomical feature.

Terminology

Although the systems and methods have been disclosed in the context of certain embodiments and examples, it will be understood by those skilled in the art that the systems and methods extend beyond the specifically disclosed embodiments to other alternative embodiments and/or uses of the embodiments and certain modifications and equivalents thereof. Various features and aspects of the disclosed embodiments can be combined with or substituted for one another in order to form varying modes of the conveyor. The scope of this disclosure should not be limited by the particular disclosed embodiments described herein.

Methods of using the foregoing system(s) (including device(s), apparatus(es), assembly(ies), structure(s) or the like) are included; the methods of use can include using or assembling any one or more of the features disclosed herein to achieve functions and/or features of the system(s) as discussed in this disclosure. Methods of manufacturing the foregoing system(s) are included; the methods of manufacture can include providing, making, connecting, assembling, and/or installing any one or more of the features of the system(s) disclosed herein to achieve functions and/or features of the system(s) as discussed in this disclosure.

Certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as any subcombination or variation of any subcombination.

Moreover, while operations may be depicted in the drawings or described in the specification in a particular order, such operations need not be performed in the particular order shown or in sequential order, and all operations need not be performed, to achieve the desirable results. Other operations that are not depicted or described can be incorporated in the example methods and processes. For example, one or more additional operations can be performed before, after, simultaneously, or between any of the described operations. Further, the operations may be rearranged or reordered in other implementations. Also, the separation of various system components in the implementations described above should not be understood as requiring such separation in all implementations, and it should be understood that the described components and systems can generally be integrated together in a single product or packaged into multiple products. Additionally, other implementations are within the scope of this disclosure.

Conditional language, such as "can," "could," "might," or "may," unless specifically stated otherwise, or otherwise understood within the context as used, is generally intended to convey that certain embodiments include or do not include, certain features, elements, and/or steps. Thus, such conditional language is not generally intended to imply that features, elements, and/or steps are in any way required for one or more embodiments.

Conjunctive language, such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Some embodiments have been described in connection with the accompanying drawings. Components can be added, removed, and/or rearranged. Orientation references such as, for example, "top" and "bottom" are for ease of ease of discussion and may be rearranged such that top features are proximate the bottom and bottom features are proximate the top. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

In summary, various embodiments and examples of juicing devices and methods have been disclosed. Although the systems and methods have been disclosed in the context of those embodiments and examples, it will be understood by those skilled in the art that this disclosure extends beyond the specifically disclosed embodiments to other alternative embodiments and/or other uses of the embodiments, as well as to certain modifications and equivalents thereof. This disclosure expressly contemplates that various features and aspects of the disclosed embodiments can be combined with, or substituted for, one another. Accordingly, the scope of this disclosure should not be limited by the particular disclosed embodiments described above, but should be determined only by a fair reading of the claims that follow.

What is claimed is:

1. A garment configured to be worn by a user to promote fluid flow within an anatomical feature of the user, the garment comprising:
   a plurality of straps configured to secure the garment to an anatomical feature of the user; and
   a plurality of compression actuator units, each of the compression actuator units comprising:
      a housing having an interior space;
      one or more levers mounted within the interior space, the one or more levers configured to rotate;
      a slide configured to be pulled against the one or more levers to cause the rotation thereof;
      a sled configured to be moved by rotation of the one or more levers, the sled coupled to a strap of the plurality of straps of the compression garments; and
      a wire wrapped around portions of the housing and the slide, wherein the wire is configured to be contracted such that the slide is pulled against the one or more levers, causing the one or more levers to rotate to move the sled and pull the strap of the plurality of straps to apply compression to the anatomical feature of the user.

2. The garment of claim 1, wherein the sled comprises a D ring configured to couple with a strap of the plurality of straps.

3. The garment of claim 1, wherein the housing comprises a plurality of channels configured to receive the wire therein.

4. The garment of claim 1, wherein the housing comprises a cover and a base, wherein an exterior surface of the cover comprises a channel configured to receive the wire therein and an interior surface of the base comprises a channel configured to receive the wire therein.

5. The garment of claim 1, wherein each of the plurality of compression actuator units is configured to amplify a stroke length from the contraction of the wire by up to one thousand percent.

6. The garment of claim 1, wherein the slide comprises one or more protrusion configured to contact the one or more levers to cause rotation.

7. The garment of claim 1, wherein the slide comprises channels configured to receive the wire therein.

8. The garment of claim 1, wherein the one or more levers comprises a first lever with a lowered portion and a second lever with a raised portion, wherein the raised portion of the second lever is configured to pass over the lowered portion of the first lever to avoid interference between the first lever and second lever during rotation.

9. The garment of claim 1, wherein the housing comprises a base and a cover, wherein the base comprises two inclined surfaces angled about an inflection point, and wherein the sled is configured to slide on at least one of the two inclined surfaces.

10. The garment of claim 1, further comprising a controller configured to apply an electrical input to the wire, raising an internal temperature of the wire such that the wire contracts.

11. The garment of claim 1, wherein the plurality of actuator units are configured to compress an anatomical feature of the user simultaneously or in sequence.

12. A garment configured to be worn by a user to promote fluid flow within a body of the user via compressive force, the garment comprising:

a strap configured to be disposed around an anatomical feature of the user; and an actuator unit comprising:

a housing having an interior space and a plurality of channels configured to receive a wire therein such that the wire wraps around features of the housing;

a first lever disposed within the interior space, the first lever configured to rotate;

a slide configured to be pulled against the first lever by a contraction of the wire to cause the rotation of the first lever; and a sled disposed at least partially within the interior space of the housing and coupled to the strap of the compression garment, the sled configured to be moved by rotation of the first lever to pull the strap to apply compression to the anatomical feature of the user.

13. The garment of claim 12, wherein the housing comprises a cover and a base, wherein plurality of channels are disposed in an exterior surface of the cover and an interior surface of the base.

14. The garment of claim 12, wherein the compression actuator unit is configured to amplify a stroke length from the contraction of the wire by up to one thousand percent.

15. The garment of claim 12, wherein the housing comprises a slot disposed in the housing, the slot configured to receive the sled therein.

16. The garment of claim 12, wherein the slide comprises one or more protrusions configured to contact the first lever to cause rotation.

17. The garment of claim 12, further comprising a second lever disposed within the interior space, wherein the slide is configured to be pulled against the second lever by the contraction of the wire to cause the rotation of the second lever, and wherein the first lever comprises a lowered portion and the second lever comprises a raised portion, wherein the raised portion of the second lever is configured to pass over the lowered portion of the first lever to avoid interference between the first lever and second lever during rotation.

18. The garment of claim 12, wherein the housing comprises a base and a cover, wherein the base comprises two inclined surfaces angled about an inflection point, and wherein the sled is configured to slide on at least one of the two inclined surfaces.

19. The garment of claim 12, further comprising a controller configured to apply an electrical input to the wire, raising an internal temperature of the wire such that the wire contracts.

20. An actuator unit comprising:

a housing having an interior space and a plurality of channels configured to receive a wire therein such that the wire wraps around features of the housing;

one or more levers disposed within the interior space, the one or more levers configured to rotate;

a slide configured to be pulled against the one or more levers by a contraction of the wire to cause the rotation of the one or more levers; and a sled disposed at least partially within the interior space of the housing, the sled configured to be moved by rotation of the one or more levers, and wherein the one or more levers are configured to amplify a pull force generated by the contraction of the wire.

* * * * *